(12) United States Patent
Cuero Rengifo et al.

(10) Patent No.: US 12,410,434 B2
(45) Date of Patent: Sep. 9, 2025

(54) GENELIGHT CULTURES AND EXTRACTS AND APPLICATIONS THEREOF

(71) Applicant: Bio Capital Holdings, LLC, Houston, TX (US)

(72) Inventors: Raul Cuero Rengifo, Cypress, TX (US); Tatiana Varela Toro, Manizales (CO); Isabella Giraldo Badillo, Aranzazu (CO); María Díaz Sánchez, Bogotá (CO); Johny Mateo Sanchez Giraldo, Manizales (CO); Juliana Londoño Murillo, Manizales (CO)

(73) Assignee: Bio Capital Holdings, LLC, Houston, TX (US)

( * ) Notice: Subject to any disclaimer, the term of this patent is extended or adjusted under 35 U.S.C. 154(b) by 861 days.

(21) Appl. No.: 17/653,395

(22) Filed: Mar. 3, 2022

(65) Prior Publication Data

US 2022/0183301 A1    Jun. 16, 2022

Related U.S. Application Data

(63) Continuation-in-part of application No. PCT/US2020/049425, filed on Sep. 4, 2020.

(60) Provisional application No. 62/896,832, filed on Sep. 6, 2019.

(51) Int. Cl.

| | | |
|---|---|---|
| *C12N 15/52* | (2006.01) | |
| *A01N 63/20* | (2020.01) | |
| *A01N 63/32* | (2020.01) | |
| *A01P 21/00* | (2006.01) | |
| *A61K 8/60* | (2006.01) | |
| *A61K 8/99* | (2017.01) | |
| *A61Q 17/04* | (2006.01) | |
| *C07K 14/245* | (2006.01) | |
| *C07K 14/395* | (2006.01) | |
| *C12N 1/14* | (2006.01) | |
| *C12N 1/20* | (2006.01) | |
| *C12N 9/00* | (2006.01) | |
| *C12N 9/02* | (2006.01) | |
| *C12N 9/88* | (2006.01) | |
| *C12N 15/87* | (2006.01) | |

(52) U.S. Cl.
CPC .............. *C12N 15/52* (2013.01); *A01N 63/20* (2020.01); *A61K 8/606* (2013.01); *C12N 1/20* (2013.01); *C12N 9/00* (2013.01); *C12N 9/0004* (2013.01); *C12N 9/88* (2013.01); *C12N 15/87* (2013.01); *C12Y 401/01039* (2013.01); *A01P 21/00* (2021.08); *A61K 8/99* (2013.01); *C12N 1/14* (2013.01)

(58) Field of Classification Search
None
See application file for complete search history.

(56) References Cited

U.S. PATENT DOCUMENTS

| | | |
|---|---|---|
| 2006/0130173 A1 | 6/2006 | Lee et al. |
| 2007/0042047 A1 | 2/2007 | Hamblin et al. |
| 2010/0129408 A1 | 5/2010 | Wang et al. |
| 2015/0140592 A1 | 5/2015 | Oard |
| 2017/0360695 A1 | 12/2017 | Cuero et al. |

FOREIGN PATENT DOCUMENTS

| | | |
|---|---|---|
| WO | 2020257524 A1 | 12/2020 |

OTHER PUBLICATIONS

International Search Report for PCT/US2020/049425 mailed Feb. 9, 2021.

*Primary Examiner* — Manjunath N Rao
*Assistant Examiner* — Jae W Lee
(74) *Attorney, Agent, or Firm* — Thomas | Horstemeyer, LLP

(57) ABSTRACT

Described herein are genelight cultures, extracts and related methods. In one aspect, the method of making a genelight culture or extract includes the steps of (a) making a DNA construct containing genes for producing a heat shock protein, RuBisCO large subunit 1, tonB, hydrogenase, and a P-type ATPase, (b) introducing the DNA construct into host microbial cells via transformation or transfection, and (c) culturing the microbial cells to produce the genelight cultures and extracts. The compositions of these cultures and extracts can be tailored to have specific properties such as the ability to provide power to a light emitting diode. The cultures and extracts have further uses including enhancing the growth of plants and as supplemental nutrients of cultures of industrially important microorganisms. The cultures and extracts further have UV-protective properties. Also described herein are microbial electric circuits containing the cultures and extracts described herein.

19 Claims, 13 Drawing Sheets
Specification includes a Sequence Listing.

GENELIGHT CULTURES AND EXTRACTS AND APPLICATIONS THEREOF

CROSS REFERENCE TO RELATED APPLICATIONS

This application is a continuation-in-part of International Patent Application No. PCT/US2020/049425, filed Sep. 4, 2020, which claims the benefit of U.S. Provisional Application No. 62/896,832, filed on Sep. 6, 2019, which is incorporated herein by reference in its entirety.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CRF), is incorporated by reference in its entirety.

BACKGROUND

Battery-powered devices are useful in applications ranging from telecommunications to medical devices to providing light during power outages. Current battery technology has several drawbacks, however. Although alkaline batteries can be recycled, few facilities exist for doing so and many end up in landfills each year. Alkaline batteries are also prone to leakage as they age and are used, which can ruin electronic devices. Lead-acid batteries are bulky, contain toxic metals, and may overheat during charging; they may also leak electrolytes (including corrosive acids) under improper storage conditions. Lithium-ion batteries are typically small and rechargeable but charge cycles are limited and transportation restrictions exist due to the possibility of short circuits leading to fires.

It would be advantageous to develop a new, inexpensive, portable power source that is effective and poses no environmental hazards during the disposal process. It would further be advantageous if this power source could make use of water-based electrolyte solutions and did not present a fire hazard during transportation or storage. It would further be advantageous if the raw materials used to generate the electrolyte solutions, or the electrolyte solutions themselves had other applications in agriculture, including plant tissue culture applications; commercial microorganism culture, including growth of organisms that produce industrially important compounds such as ethanol, acetic acid, rennet, insulin, and related compounds; and the like, either as a separate use or as a use for electrolyte solutions that have aged out of useful life. The present invention addresses these needs.

SUMMARY

Described herein are genelight cultures and extracts and methods of making and using thereof. In one aspect, the method of making a genelight culture or extract includes the steps of (a) making a DNA construct containing genes for producing a heat shock protein, RuBisCO large subunit 1, tonB, hydrogenase, and a P-type ATPase, (b) introducing the DNA construct into host microbial cells via transformation or transfection, and (c) culturing the microbial cells to produce the genelight cultures and extracts. The compositions of these cultures and extracts can be tailored to have specific properties such as the ability to provide power to a light emitting diode. The cultures and extracts have further uses including enhancing the growth of plants and as supplemental nutrients of cultures of industrially important microorganisms. The cultures and extracts further have UV-protective properties. Also described herein are microbial electric circuits containing the cultures and extracts described herein.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
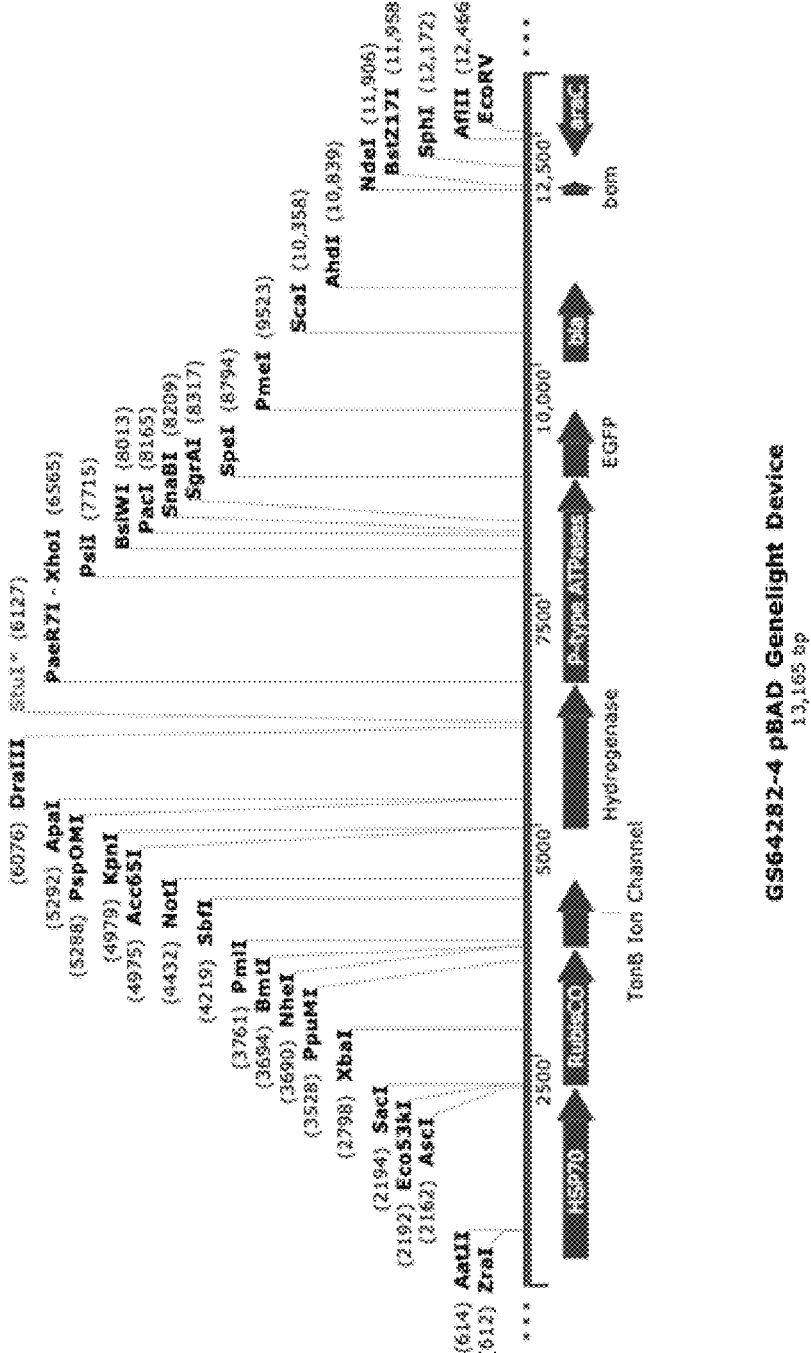
FIG. 1 shows a linear schematic of a constructed pBAD plasmid showing the direction, placement, and size of genetic parts used for an exemplary DNA device described herein.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a restriction enzyme" includes mixtures of two or more such restriction enzymes, and the like.

"Optional" or "optionally" means that the subsequently described event or circumstance can or cannot occur, and that the description includes instances where the event or circumstance occurs and instances where it does not. For example, the phrase "optionally includes a gene for a reporter protein" means that the gene for the reporter protein may or may not be present.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, the term "about" is used to provide flexibility to a numerical range endpoint by providing that a given numerical value may be "a little above" or "a little below" the endpoint without affecting the desired result. For purposes of the present disclosure, "about" refers to a range extending from 10% below the numerical value to 10% above the numerical value. For example, if the numerical value is 10, "about 10" means between 9 and 11 inclusive of the endpoints 9 and 11.

"Admixing" or "admixture" refers to a combination of two or more components together wherein there is no chemical reaction or physical interaction. The terms "admixing" and "admixture" can also include the chemical reaction or physical interaction between any of the components described herein upon mixing to produce the composition. The components can be admixed alone, in water, in another solvent, or in a combination of solvents.

"Root tension" as used herein refers to the resistance of a plant or a patch of sod from being uprooted or removed from the ground when pulled. In some aspects, the compositions and extracts disclosed herein, when applied to plants such as, for example, grass, can increase the root tension of the plants. Root tension can be measured using a tension meter and can be given in units of force such as, for example, Newtons (kg·m/s$^2$).

As used herein, the term "reduce" is defined as the ability to reduce the likelihood of an event (e.g., exposure to UV radiation) from occurring up to about 50%, up to about 60%, up to about 70%, up to about 80%, up to about 90%, up to about 95%, or up to about 99% when compared to not using the methods as described herein. As used herein, the term "reduce" is also defined as the ability to completely eliminate the likelihood of the event from occurring when compared to not using the methods as described herein.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed that while specific reference to each various individual and collective combination and permutation of these compounds may not be explicitly disclosed, each is specifically contemplated and described herein. For example, if a pharmaceutical composition is disclosed and discussed and a number of pharmaceutically-acceptable carriers are discussed, each and every combination and permutation of pharmaceutical composition and pharmaceutically-acceptable carrier that is possible is specifically contemplated unless specifically indicated to the contrary. For example, if a class of molecules A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the subgroup of A-E, B-F, and C-E is specifically contemplated and should be considered disclosed from disclosure of A, B, and C; D, E, and, F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, a "genelight extract" is an extract produced by the biological devices disclosed herein. In one aspect, the genelight extract contains the biological devices in either a lysed or a whole cell state. In another aspect, the genelight extract contains proteins encoded by the genes in the DNA constructs disclosed herein, or contains the catalytic products of these proteins, or a combination thereof. In one aspect, the genelight extract is capable of providing power to a light source. In a further aspect, the genelight extract can be used to enhance the growth of plants, including plants grown from tissue culture, or can be used to provide supplemental nutrients for cultures of industrially, commercially, and/or scientifically important microorganisms.

Described herein are genelight cultures and extracts and methods of making and using thereof. In one aspect, the method of making a genelight culture or extract includes the steps of (a) making a DNA construct containing genes for producing a heat shock protein, RuBisCO large subunit 1, tonB, hydrogenase, and a P-type ATPase, (b) introducing the DNA construct into host microbial cells via transformation or transfection, and (c) culturing the microbial cells to produce the genelight cultures and extracts. The cultures are grown in standard media for host cells such as, for example, *E. coli* or *S. cerevisiae*. The compositions of these cultures and extracts can be tailored to have specific properties such as, for example, the ability to provide power to a light emitting diode (LED) with a specific voltage. The cultures and extracts have further uses including enhancing the growth of plants, including plants grown from tissue culture, and as supplemental nutrients of cultures of industrially, commercially, and/or scientifically important microorganisms. The cultures and extracts further have UV-protective and/or UV-blocking properties and can be incorporated into or applied on various materials, surfaces, and human or animal subjects for the purpose of protecting those materials, surfaces, and human or animal subjects from the harmful effects of radiation. Also described herein are microbial electric circuits containing the microbial cultures and extracts described herein as well as applications of those circuits.

DNA Constructs and Biological Devices

DNA constructs are provided herein for the production of genelight extracts. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning two sequences so that the homology is at its highest level. Another way of calculating homology can be performed according to published algorithms (see Zuker, M., *Science*, 244:48-52, 1989; Jaeger et al, *Proc. Natl. Acad. Sci. USA*, 86:7706-7710, 1989; Jaeger et al, *Methods Enzymol.*, 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least about 70%, about 75%, about 80%, about 85%, about 90%, about 95%, or about 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, provided herein are DNA constructs having at least the following genetic components:
 a) a gene that expresses a heat shock protein;
 b) a gene that expresses RuBisCO large subunit 1;
 c) a gene that expresses tonB;
 d) a gene that expresses hydrogenase; and
 e) a gene that expresses P-type ATPase.

Each component of the DNA constructs are described in detail below.

In one aspect, the nucleic acids (e.g., genes that express a heat shock protein, RuBisCO large subunit 1, tonB, hydrogenase, and P-type ATPase) used in the DNA constructs described herein can be amplified using polymerase chain reaction (PCR) prior to being ligated into a plasmid or other vector. Typically, PCR-amplification techniques make use of primers, or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the anti sense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or genes. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

In one aspect, the DNA constructs disclosed herein include a gene for a heat shock protein. Heat shock proteins are a group of proteins that is produced by cells in response to exposure to stressful conditions. In a further aspect, heat shock proteins can be expressed in response to heat shock but also to cold, UV light, wound healing, exposure to toxic chemicals such as, for example heavy metals, including but not limited to arsenic, cadmium, copper, mercury, and the like, as well as during tissue remodeling. In a further aspect, a heat shock protein may function as a chaperone protein by assisting in the refolding process of proteins damaged by cell stress. In a further aspect, the heat shock protein can be HSP60, HSP70, or HSP90, where the number refers to the size in kilodaltons of the protein. In one aspect, the heat shock protein is HSP70 and has a weight of about 70 kDa.

In a further aspect, the gene that expresses a heat shock protein expresses HSP70. In another aspect, the gene that expresses a heat shock protein is isolated from a fungus. In a still further aspect, the fungus is a yeast such as, for example, Saccharomyces cerevisiae. Further in this aspect, the S. cerevisiae strain can be strain ySR128, Y169, SY14, BY4742, CEN.PK113-7D, S288c, YJM1326, ySR127, S288C, EC1118, Makgeolli, UWOPS03-461.4, DBVPG6765, YJM1447, YJM981, YJM627, YJM1401, YJM1356, YJM978, YJM320, YJM1527, YJM1355, YJM554, HB_S_GIMBLETTROAD_16, WI_S_OAKURA_4, HB_S_BILANCHER_6, HB_S_GIMBLETTROAD_14, T52, T52_5E HB_S_GIMBLETTROAD_22, HB_C_OMARUNUI_7, HB_C_TUKITUKI1_16, HB_C_TUKITUKI2_10, WI_S_JASA_13, WI_S_JASA_5, HB_C_OMARUNUI_14, WA_C_MATES_13, WI_C_MBSP_4, WA_C_CODDINGTON_2, T8, Soil7-1, WA_C_MATES_10, HB_S_GIMBLETTROAD_5, HCNKIsf_G7, HPRMIsf_H7, T16, MARARsf_A10, MTKSKsf_E2, WSETAwf_B1, HB_S_GIMBLETTROAD_9, TNPLST-4-S-2, CDRDR_sf_H, CRIRIwf_A11, T78, NSERVsf_F8, HB_C_TUKITUKI2_4, T.52_3A, YJM1526, YJM969, YJM1478, YJM1338, YJM993, YJM1477, YJM1387, YJM453, YJM1242, YJM683, YJM987, YJM450, UOA_M2, YJM1415, KSD-Yc, YPS128, YJM1573, YJM1190, YJM555, YJM1400, YJM1273, T63, HB_S_BILANCHER_12, HB_C_KOROKIPO_12, Sol7-2, HCNTHsf_F8, HB_C_KOROKIPO_3, HB_C_OMARUNUI_6, WA_C_WAITAKERSROAD_7, HCNTHsf_C5, T.52_5A, WA_C_KINGSMILL_10, NSEBRsf_A9, HPRMAwf_D10, T.52_2H, T.52_3C, YJM1129, WSERCsf_G4, or another S. cerevisiae strain. In a further aspect, the gene that expresses a heat shock protein has SEQ ID NO. 1 or at least 70% homology thereto, at least 75% homology thereto, at least 80% homology thereto, at least 90% homology thereto, at least 95% homology thereto, or at least 99% homology thereto.

Other sequences expressing a heat shock protein or related or homologous genes can be identified in a database such as, for example, GenBank. In one aspect, the gene that expresses a heat shock protein is isolated from S. cerevisiae strain ySR128 having GI number CP036483.1 in the GenBank database. In one aspect, sequences useful herein include those with GI numbers listed in Table 1:

TABLE 1

Heat Shock Protein Genes

| Source Organism | Sequence Description | GI Number |
| --- | --- | --- |
| Saccharomyces cerevisiae | chromosome IV sequence | CP036483.1 |
| Saccharomyces cerevisiae | chromosome IV sequence | CP033473.1 |
| Saccharomyces cerevisiae | chromosome I sequence | CP029160.1 |
| Saccharomyces cerevisiae | chromosome IV sequence | CP029160.1 |
| Saccharomyces cerevisiae | chromosome IV sequence | CP029160.1 |
| Saccharomyces cerevisiae | chromosome IV sequence | CP029160.1 |
| Saccharomyces cerevisiae | chromosome IV sequence | CP029160.1 |
| Saccharomyces cerevisiae | chromosome IV sequence | CP026298.1 |
| Saccharomyces cerevisiae | chromosome IV sequence | CP022969.1 |
| Saccharomyces cerevisiae | HSP70 family | CP020126.1 |
| Saccharomyces cerevisiae | chromosome IV sequence | CP004710.2 |
| Saccharomyces cerevisiae | chromosome IV sequence | CP011550.1 |
| Saccharomyces cerevisiae | heat shock cognate gene | BK006938.2 |
| Saccharomyces cerevisiae | genomic DNA | NM_001180289.1 |
| Saccharomyces cerevisiae | chromosome IV sequence | FN393064.1 |
| Saccharomyces cerevisiae | chromosome IV sequence | Z74277.1 |
| Saccharomyces cerevisiae | chromosome I sequence | X13713.1 |
| Saccharomyces cerevisiae | chromosome IV sequence | EF058944.1 |
| Saccharomyces cerevisiae | chromosome IV sequence | CP025100.1 |
| Saccharomyces cerevisiae | chromosome IV sequence | CP020228.1 |

TABLE 1-continued

Heat Shock Protein Genes

| Source Organism | Sequence Description | GI Number |
|---|---|---|
| Saccharomyces cerevisiae | chromosome IV sequence | CP020160.1 |
| Saccharomyces cerevisiae | chromosome IV sequence | CP004738.2 |
| Saccharomyces cerevisiae | chromosome IV sequence | CP004688.2 |
| Saccharomyces cerevisiae | chromosome IV sequence | CP004678.2 |
| Saccharomyces cerevisiae | chromosome IV sequence | CP004727.2 |
| Saccharomyces cerevisiae | chromosome I sequence | CP004717.2 |
| Saccharomyces cerevisiae | chromosome IV sequence | CP004687.2 |
| Saccharomyces cerevisiae | chromosome IV sequence | CP004667.2 |
| Saccharomyces cerevisiae | chromosome IV sequence | CP004746.2 |
| Saccharomyces cerevisiae | chromosome IV sequence | CP004716.2 |
| Saccharomyces cerevisiae | chromosome IV sequence | CP004676.2 |
| Saccharomyces cerevisiae | chromosome IV sequence | CP008239.1 |
| Saccharomyces cerevisiae | chromosome IV sequence | CP008324.1 |
| Saccharomyces cerevisiae | chromosome IV sequence | CP008273.1 |
| Saccharomyces cerevisiae | chromosome I sequence | CP008256.1 |
| Saccharomyces cerevisiae | chromosome IV sequence | CP008222.1 |
| Saccharomyces cerevisiae | chromosome IV sequence | CP008409.1 |
| Saccharomyces cerevisiae | chromosome IV sequence | CP008392.1 |
| Saccharomyces cerevisiae | chromosome IV sequence | CP008375.1 |
| Saccharomyces cerevisiae | chromosome IV sequence | CP008358.1 |
| Saccharomyces cerevisiae | chromosome IV sequence | CP008341.1 |
| Saccharomyces cerevisiae | chromosome IV sequence | CP008494.1 |
| Saccharomyces cerevisiae | chromosome IV sequence | CP008443.1 |
| Saccharomyces cerevisiae | chromosome I sequence | CP008579.1 |
| Saccharomyces cerevisiae | chromosome IV sequence | CP008511.1 |
| Saccharomyces cerevisiae | chromosome IV sequence | CP008647.1 |
| Saccharomyces cerevisiae | chromosome IV sequence | CP008630.1 |
| Saccharomyces cerevisiae | chromosome IV sequence | CP008596.1 |
| Saccharomyces cerevisiae | chromosome IV sequence | CP008188.1 |
| Saccharomyces cerevisiae | chromosome IV sequence | CP008171.1 |
| Saccharomyces cerevisiae | chromosome IV sequence | CP008154.1 |
| Saccharomyces cerevisiae | chromosome IV sequence | CP008681.1 |
| Saccharomyces cerevisiae | chromosome I sequence | CP008137.1 |
| Saccharomyces cerevisiae | chromosome IV sequence | CP008120.1 |
| Saccharomyces cerevisiae | chromosome IV sequence | CP008086.1 |
| Saccharomyces cerevisiae | chromosome IV sequence | CP008052.1 |
| Saccharomyces cerevisiae | chromosome IV sequence | CP008035.1 |
| Saccharomyces cerevisiae | chromosome IV sequence | CP008001.1 |
| Saccharomyces cerevisiae | chromosome IV sequence | CP007984.1 |
| Saccharomyces cerevisiae | chromosome IV sequence | CP007950.1 |
| Saccharomyces cerevisiae | chromosome IV sequence | CP007899.1 |
| Saccharomyces cerevisiae | chromosome I sequence | CP007882.1 |
| Saccharomyces cerevisiae | chromosome IV sequence | CP007831.1 |
| Saccharomyces cerevisiae | chromosome IV sequence | CP004745.2 |
| Saccharomyces cerevisiae | chromosome IV sequence | CP004684.2 |
| Saccharomyces cerevisiae | chromosome IV sequence | CP004743.2 |
| Saccharomyces cerevisiae | chromosome IV sequence | CP004713.2 |
| Saccharomyces cerevisiae | chromosome IV sequence | CP004692.2 |
| Saccharomyces cerevisiae | chromosome IV sequence | CP004742.2 |
| Saccharomyces cerevisiae | chromosome IV sequence | CP004722.2 |
| Saccharomyces cerevisiae | chromosome I sequence | CP004672.2 |
| Saccharomyces cerevisiae | chromosome IV sequence | CP004701.2 |
| Saccharomyces cerevisiae | chromosome IV sequence | CP004681.2 |
| Saccharomyces cerevisiae | chromosome IV sequence | CP004690.2 |
| Saccharomyces cerevisiae | chromosome IV sequence | CP004670.2 |
| Saccharomyces cerevisiae | chromosome IV sequence | CP011082.1 |
| Saccharomyces cerevisiae | chromosome IV sequence | CP004729.1 |
| Saccharomyces cerevisiae | chromosome IV sequence | M25395.1 |
| Saccharomyces cerevisiae | chromosome IV sequence | CP023998.1 |
| Saccharomyces cerevisiae | chromosome I sequence | CP020211.1 |
| Saccharomyces cerevisiae | chromosome IV sequence | CP004748.2 |
| Saccharomyces cerevisiae | chromosome IV sequence | CP004697.2 |
| Saccharomyces cerevisiae | chromosome IV sequence | CP004677.2 |
| Saccharomyces cerevisiae | chromosome IV sequence | CP004726.2 |
| Saccharomyces cerevisiae | chromosome IV sequence | CP004706.2 |
| Saccharomyces cerevisiae | chromosome IV sequence | CP008307.1 |
| Saccharomyces cerevisiae | chromosome IV sequence | CP008290.1 |
| Saccharomyces cerevisiae | chromosome IV sequence | CP008477.1 |
| Saccharomyces cerevisiae | chromosome I sequence | CP008460.1 |
| Saccharomyces cerevisiae | chromosome IV sequence | CP008426.1 |
| Saccharomyces cerevisiae | chromosome IV sequence | CP008562.1 |
| Saccharomyces cerevisiae | chromosome IV sequence | CP008664.1 |
| Saccharomyces cerevisiae | chromosome IV sequence | CP008613.1 |
| Saccharomyces cerevisiae | chromosome IV sequence | CP008103.1 |
| Saccharomyces cerevisiae | chromosome IV sequence | CP008069.1 |
| Saccharomyces cerevisiae | chromosome IV sequence | CP008018.1 |

TABLE 1-continued

Heat Shock Protein Genes

| Source Organism | Sequence Description | GI Number |
|---|---|---|
| Saccharomyces cerevisiae | chromosome IV sequence | CP007967.1 |
| Saccharomyces cerevisiae | chromosome IV sequence | CP007933.1 |
| Saccharomyces cerevisiae | chromosome IV sequence | CP007916.1 |
| Saccharomyces cerevisiae | chromosome IV sequence | CP007865.1 |
| Saccharomyces cerevisiae | chromosome IV sequence | CP007848.1 |
| Saccharomyces cerevisiae | chromosome IV sequence | CP007814.1 |
| Saccharomyces cerevisiae | chromosome IV sequence | CP004695.2 |
| Saccharomyces cerevisiae | chromosome IV sequence | CP008205.1 |

In one aspect, the DNA constructs disclosed herein include a gene that expresses ribulose-1,5-bisphosphate carboxylase/oxygenase (RuBisCO) large subunit 1. RuBisCO is an enzyme involved in carbon fixation and can be isolated from plants, algae, cyanobacteria, and phototrophic and/or chemoautotrophic proteobacteria. In a further aspect, the RuBisCO large subunit is typically encoded by chloroplast DNA. In a still further aspect, RuBisCO typically catalyzes the formation of two molecules of glycerate-3-phosphate from ribulose-1,5-bisphosphate and carbon dioxide. In an alternative aspect, RuBisCO is capable of catalyzing the formation of phosphoglycolate and 3-phosphoglycerate from ribulose-1,5-bisphosphate and molecular oxygen.

In one aspect, the gene that expresses RuBisCO large subunit 1 is isolated from an alga. In another aspect, the alga can be selected from *Guillardia theta, Storeatula* sp. CCMP1668, Hanusia phi, a *Rhodomonas* species, *Teleaulax amphioxeia*, a *Cryptomonas* species, *Pyrenomonas helgolandii*, a *Botrydium* species, a *Xanthonema* species, *Chrysoparadoxa australica, Ophiocytium majus, Chroomonas* sp. SAG 980-1, *Porphyridium aerugineum*, a *Bumilleria* species, a *Hemiselmis* species, a *Bumilleriopsis* species, *Ophiocytium capitatum, Erythrotrichia carnea, Tribonema* sp. UTEX 639, *Heterothrix debilis, Mischococcus sphaerocephalus*, a *Tribonema* species, *Ophiocytium parvulum, Porphyridium sordidum, Nitzschia* sp. SZCZP 1124, or *Exanthemachrysis gayraliae*. In a further aspect, the gene that expresses RuBisCO large subunit 1 is isolated from a plastid or chloroplast present in these or other algae. In a still further aspect, the gene that expresses RuBisCO large subunit 1 has SEQ ID NO. 2 or at least 70% homology thereto, at least 75% homology thereto, at least 80% homology thereto, at least 85% homology thereto, at least 90% homology thereto, at least 95% homology thereto, or at least 99% homology thereto.

Other sequences expressing RuBisCO large subunit 1 or related or homologous genes can be identified in a database such as, for example, GenBank. In one aspect, the gene that expresses RuBisCO large subunit 1 is isolated from *Guillardia theta* and has GI number AF041468.1 in the GenBank database. In another aspect, sequences useful herein include those with the GI numbers listed in Table 2:

TABLE 2

RuBisCO Large Subunit 1 Genes

| Source Organism | Sequence Description | GI Number |
|---|---|---|
| Guillardia theta | plastid gene | AF041468.1 |
| Guillardia theta | RuBisCO large subunit | MK818447.1 |
| Guillardia theta | chloroplast gene | KT428890.1 |
| Storeatula sp. CCMP 1668 | plastid gene | KY856940.1 |
| Hanusia phi | RuBisCO large subunit | KX777654.1 |
| Rhodomonas salina | chloroplast gene | EF508371.1 |
| Teleaulax amphioxeia | plastid gene | KP899713.1 |
| Cyrptomonas curvata | plastid gene | KY856939.1 |
| Chroomonas placoidea | plastid gene | KY856941.1 |
| Chroomonas mesostigmatica | chloroplast gene | KY860574.1 |
| Cryptomonas pyrenoidifera | RuBisCO large subunit | AM051217.1 |
| Cryptomonas marssonii | RuBisCO large subunit | AM051209.1 |
| Cryptomonas tetrapyrenoidosa | RuBisCO large subunit | AM051219.1 |
| Cryptomonas sp. CCAP 979/46 | RuBisCO large subunit | AM051223.1 |
| Cryptomonas pyrenoidifera | RuBisCO large subunit | AM051216.1 |
| Cryptomonas sp. CCAC 0109 | RuBisCO large subunit | AM051222.1 |
| Cryptomonas curvata | RuBisCO large subunit | AM051204.1 |
| Cyrptomonas tetrapyrenoidosa | RuBisCO large subunit | AM051220.1 |
| Cryptomonas curvata | RuBisCO large subunit | AM051205.1 |
| Cryptomonas sp. CCAC 0031 | RuBisCO large subunit | AM051221.1 |
| Cryptomonas ovata | RuBisCO large subunit | AM051210.1 |
| Pyrenomonas helgolandii | RuBisCO large subunit | AY119782.1 |
| Botrydium stoloniferum | RuBisCO large subunit | AF465707.1 |
| Botrydium stoloniferum | RuBisCO large subunit | EF455981.1 |
| Xanthonema muciculum | RuBisCO large subunit | EF455957.1 |
| Hanusia phi | RuBisCO large subunit | MK818448.1 |
| Cryptomonas ovata | RuBisCO large subunit | AM051211.1 |
| Chrysoparadoxa australica | RuBisCO large subunit | MK189080.1 |
| Botrydium granulatum | RuBisCO large subunit | EF455980.1 |
| Cryptomonas sp. M0741 | RuBisCO large subunit | AM051224.1 |
| Rhodomonas sp. isolate CCMP 757 | RuBisCO large subunit | KX777650.1 |

TABLE 2-continued

RuBisCO Large Subunit 1 Genes

| Source Organism | Sequence Description | GI Number |
| --- | --- | --- |
| *Xanthonema* sp. SAG 60.94 | RuBisCO large subunit | EF455977.1 |
| *Porphyridium aerugineum* | RuBisCO large subunit | X17597.1 |
| *Xanthonema* sp. SAG 2192 | RuBisCO large subunit | EF426794.1 |
| *Xanthonema* cf. *hormidioides* strain SAG 2194 | RuBisCO large subunit | EF455953.1 |
| *Ophiocytium majus* | RuBisCO large subunit | EF455971.1 |
| *Chroomonas* sp. SAG 980-1 | RuBisCO large subunit | AY119781.1 |
| *Xanthonema* sp. CCAP 836/5 | RuBisCO large subunit | EF455940.1 |
| *Xanthonema exile* | RuBisCO large subunit | EF455929.1 |
| *Xanthonema bristolianum* | RuBisCO large subunit | EF455955.1 |
| *Xanthonema* sp. SAG 2189 | RuBisCO large subunit | EF455954.1 |
| *Xanthonema* sp. SAG 2179 | RuBisCO large subunit | EF426796.1 |
| *Xanthonema debile* | RuBisCO large subunit | EF455975.1 |
| *Xanthonema hormidioides* | RuBisCO large subunit | EF455939.1 |
| *Bumilleria exilis* | RuBisCO large subunit | EF455937.1 |
| *Xanthonema hormidioides* | RuBisCO large subunit | EF455922.1 |
| *Cryptomonas gyropyrenoidosa* | RuBisCO large subunit | AM051206.1 |
| *Hemiselmis* sp. isolate SUR21-C3 | RuBisCO large subunit | KX777660.1 |
| *Hemiselmis pacifica* | RuBisCO large subunit | KX777646.1 |
| *Hemiselmis rufescens* | RuBisCO large subunit | KX777647.1 |
| *Bumilleriopsis* sp. SAG 33.93 | RuBisCO large subunit | EF431849.1 |
| *Xanthonema solidum* | RuBisCO large subunit | EF455973.1 |
| *Xanthonema sessile* | RuBisCO large subunit | EF455935.1 |
| *Bumilleriopsis* sp. SAG 57.94 | RuBisCO large subunit | EF431850.1 |
| *Bumilleriopsis peterseniana* | RuBisCO large subunit | EF455942.1 |
| *Xanthonema mucicolum* | RuBisCO large subunit | AJ874332.1 |
| *Botrydium cystosum* | RuBisCO large subunit | AF465708.1 |
| *Botrydium stoloniferum* | RuBisCO large subunit | AF064743.1 |
| *Rhodomonas salina* | RuBisCO large subunit | MK818469.1 |
| *Botrydium becharianum* | RuBisCO large subunit | EF455979.1 |
| *Ophiocytium capitatum* | RuBisCO large subunit | EF455959.1 |
| *Xanthonema* sp. SAG 2184 | RuBisCO large subunit | EF455931.1 |
| *Xanthonema* sp. 907 | RuBisCO large subunit | AJ874714.1 |
| *Botrydium becharianum* | RuBisCO large subunit | AF465706.1 |
| *Erythrotrichia carnea* | plastid gene | NC_031176.2 |
| *Erythrotrichia carnea* | plastid gene | KX284721.2 |
| *Tribonema* sp. UTEX 639 | RuBisCO large subunit | EF455921.1 |
| *Bumilleria* sp. CCAP 806/3 | RuBisCO large subunit | EF455938.1 |
| *Heterothrix debilis* | RuBisCO large subunit | EF455920.1 |
| *Ophiocytium majus* | RuBisCO large subunit | AJ874699.1 |
| *Rhodomonas lens* | RuBisCO large subunit | MK818450.1 |
| *Hemiselmis andersenii* | RuBisCO large subunit | KX777655.1 |
| *Xanthonema* sp. SAG 2183 | RuBisCO large subunit | EF455930.1 |
| *Mischococcus sphaerocephalus* | RuBisCO large subunit | EF455972.1 |
| *Xanthonema bristolianum* | RuBisCO large subunit | AJ874331.1 |
| *Xanthonema* cf. *debile* | RuBisCO large subunit | EF455932.1 |
| *Bumilleria* sp. SAG2160 | RuBisCO large subunit | EF460494.1 |
| *Bumilleriopsis* sp. SAG 58.94 | RuBisCO large subunit | EF455963.1 |
| *Ophiocytium parvulum* | RuBisCO large subunit | EF455961.1 |
| *Xanthonema debile* | RuBisCO large subunit | EF455933.1 |
| *Porphyridium sordidum* | plastid gene | KX284720.1 |
| *Xanthonema debile* | RuBisCO large subunit | AF084612.1 |
| *Hemiselmis rufescens* | RuBisCO large subunit | MK818472.1 |
| *Tribonema viride* | RuBisCO large subunit | EF460493.1 |
| *Bumilleria klebsiana* | RuBisCO large subunit | EF460492.1 |
| *Bumilleria* sp. SAG 2157 | RuBisCO large subunit | EF426792.1 |
| *Tribonema regulare* | RuBisCO large subunit | EF455928.1 |
| *Xanthonema* sp. 773 | RuBisCO large subunit | AJ874713.1 |
| *Bumilleriopsis* sp. SAG 33.93 | RuBisCO large subunit | AJ874706.1 |
| *Botrydium granulatum* | RuBisCO large subunit | AJ874698.1 |
| *Xanthonema sessile* | RuBisCO large subunit | AJ874329.1 |
| *Tribonema intermixum* | RuBisCO large subunit | AF465709.1 |
| *Nitzschia* sp. SZCZP1124 | RuBisCO large subunit | LC385875.1 |
| *Cryptomonas pyrenoidifera* | RuBisCO large subunit | MK818480.1 |
| *Exanthemachrysis gayraliae* | RuBisCO large subunit | AB043701.1 |
| *Tribonema intermixum* | RuBisCO large subunit | EF460491.1 |
| *Tribonema* sp. SAG 2176 | RuBisCO large subunit | EF455950.1 |
| *Tribonema viride* | RuBisCO large subunit | EF455966.1 |
| *Cyrptomonas rostratiformis* | RuBisCO large subunit | MK818486.1 |
| *Rhodomonas abbreviata* | RuBisCO large subunit | MK818476.1 |

In one aspect, the DNA constructs disclosed herein incorporate a gene that expresses tonB. TonB is a beta barrel protein found in the outer membrane of gram-negative bacteria. In a still further aspect, tonB proteins are involved with the uptake and/or transport of large substrates including iron siderophore complexes, heme, and other chelated forms of iron.

In one aspect, the gene that expresses tonB is isolated from a bacterium such as, for example, *Enterococcus faecalis*, *Stenotrophomonas rhizophila*, or a *Pseudomonas* species. In another aspect, the *Pseudomonas* species is selected from *P. entomophila*, *P.* sp. CCOS191, *P. plecoglossicida*, *P. mosselii*, *P. putida*, *P.* sp. PONIH3, *P. soli*, *P.* sp. LTGT-11-2Z, *P. monteilii*, *P.* sp. DRA525, *P. syringae*, *P. avellanae*, *P. chloroaphis*, *P.* sp. GR 6-02, *P. frederiksbergensis*, *P.* sp. ATCC 43928, *P. chloroaphis*, *P. parafulva*, *P. fulva*, *P.* sp. BJP69, *P.* sp. Leaf58, *P.* sp. SW144, *P.* sp. VLB120, *P.* sp. SW16, *P.* sp. 02C 26, *P.* sp. URMO17WK12:I11, *P.* sp. SW17, *P.* sp. SGair0191, *P. cremoricolorata*, *P.* sp. SNU WTI, *P. aklylphenolica*, *P.* sp. DG56-2, *P.* sp. HLS-6, *P. rhizosphaerae*, *P. viridiflava*, *P. cichorii*, *P.* sp. MRSN12121, or *P. fluorescens*. In a further aspect, the gene that expresses tonB has SEQ ID NO. 3 or at least 70% homology thereto, at least 75% homology thereto, at least 80% homology thereto, at least 85% homology thereto, at least 90% homology thereto, at least 95% homology thereto, or at least 99% homology thereto.

Other sequences expressing tonB or related or homologous genes can be identified in a database such as, for example, GenBank. In one aspect, the gene that expresses tonB is isolated from *Pseudomonas entomophila* and can be identified by the GI number CT573326.1 in the GenBank database. In another aspect, sequences useful herein include those with GI numbers listed in Table 3:

TABLE 3

TonB Genes

| Source Organism | Sequence Description | GI Number |
| --- | --- | --- |
| *Pseudomonas entomophila* | chromosomal DNA | CT573326.1 |
| *Pseudomonas* sp. CCOS191 | chromosomal DNA | LN847264.1 |
| *Pseudomonas entomophila* | genomic DNA | CP034337.1 |
| *Pseudomonas entomophila* | genomic DNA | CP034338.1 |
| *Pseudomonas plecoglossicida* | genomic DNA | CP031146.1 |
| *Pseudomonas mosselii* | genomic DNA | CP024159.1 |
| *Pseudomonas mosselii* | genomic DNA | CP023299.1 |
| *Pseudomonas putida* | genomic DNA | CP014343.1 |
| *Pseudomonas* sp. PONIH3 | genomic DNA | CP026386.1 |
| *Pseudomonas soli* | genomic DNA | CP009365.1 |
| *Pseudomonas putida* | genomic DNA | CP018846.1 |
| *Pseudomonas putida* | genomic DNA | CP010979.1 |
| *Pseudomonas* sp. LTGT-11-2Z | genomic DNA | CP033104.1 |
| *Pseudomonas monteilii* | genomic DNA | CP022562.1 |
| *Pseudomonas* sp. DRA525 | genomic DNA | CP018743.1 |
| *Pseudomonas putida* | genomic DNA | CP003738.1 |
| *Pseudomonas monteilii* | genomic DNA | CP014062.1 |
| *Pseudomonas putida* | genomic DNA | AP013070.1 |
| *Pseudomonas* sp. FGI182 | genomic DNA | CP007012.1 |
| *Pseudomonas putida* | genomic DNA | CP002870.1 |
| *Pseudomonas putida* | genomic DNA | CP000926.1 |
| *Pseudomonas* sp. XWY-1 | genomic DNA | CP026332.1 |
| *Pseudomonas* sp. JY-Q | genomic DNA | CP011525.1 |
| *Pseudomonas putida* | genomic DNA | CP003734.1 |
| *Pseudomonas putida* | TonB | AF315582.1 |
| *Pseudomonas putida* | genomic DNA | CP017073.1 |
| *Pseudomonas* sp. KBS0802 | genomic DNA | CP042180.1 |
| *Pseudomonas putida* | genomic DNA | CP022561.1 |
| *Pseudomonas putida* | chromosomal DNA | LR134299.1 |
| *Pseudomonas* sp. SWI36 | genomic DNA | CP026675.1 |
| *Pseudomonas putida* | chromosomal DNA | LT799039.1 |
| *Pseudomonas putida* | genomic DNA | AE015451.2 |
| *Pseudomonas plecoglossicida* | genomic DNA | CP010359.1 |
| *Pseudomonas putida* | genomic DNA | CP007620.1 |
| *Pseudomonas monteilii* | genomic DNA | CP006979.1 |
| *Pseudomonas monteilii* | genomic DNA | CP006978.1 |
| *Pseudomonas putida* | chromosomal DNA | LT707061.1 |
| *Pseudomonas putida* | genomic DNA | CP016212.1 |
| *Pseudomonas putida* | genomic DNA | CP015876.1 |
| *Pseudomonas putida* | genomic DNA | CP015202.1 |
| *Pseudomonas putida* | genomic DNA | CP009974.1 |
| *Pseudomonas putida* | genomic DNA | CP003588.1 |
| *Pseudomonas putida* | genomic DNA | CP002290.1 |
| *Pseudomonas putida* | genomic DNA | CP000712.1 |
| *Stenotrophomonas rhizophila* | genomic DNA | CP031729.1 |
| *Pseudomonas putida* | genomic DNA | AP015029.1 |
| *Pseudomonas putida* | genomic DNA | CP005976.1 |
| *Pseudomonas* sp. BJP69 | genomic DNA | CP041933.1 |
| *Pseudomonas putida* | genomic DNA | CP030750.1 |
| *Pseudomonas putida* | genomic DNA | CP011789.1 |
| *Pseudomonas* sp. Leaf58 | genomic DNA | CP032677.1 |
| *Pseudomonas putida* | genomic DNA | CP024086.1 |
| *Pseudomonas putida* | genomic DNA | CP024085.1 |

TABLE 3-continued

TonB Genes

| Source Organism | Sequence Description | GI Number |
| --- | --- | --- |
| *Pseudomonas putida* | TonB | X70139.1 |
| *Pseudomonas putida* | genomic DNA | CP016634.1 |
| *Pseudomonas* sp. SWI44 | genomic DNA | CP026674.1 |
| *Pseudomonas* sp. VLB120 | genomic DNA | CP003961.1 |
| *Pseudomonas* sp. SWI6 | genomic DNA | CP026676.1 |
| *Pseudomonas putida* | genomic DNA | CP039371.1 |
| *Pseudomonas parafulva* | genomic DNA | CP031641.1 |
| *Pseudomonas parafulva* | genomic DNA | CP009747.1 |
| *Pseudomonas putida* | genomic DNA | CP000949.1 |
| *Pseudomonas* sp. 02C 26 | chromosomal DNA | CP025262.1 |
| *Pseudomonas fulva* | genomic DNA | CP014025.1 |
| *Pseudomonas* sp. UPMO17WK12:I11 | chromosomal DNA | LN865164.1 |
| *Pseudomonas fulva* | genomic DNA | CP023048.1 |
| *Pseudomonas* sp. SWI7 | genomic DNA | CP040930.1 |
| *Pseudomonas* sp. SGair0191 | genomic DNA | CP025035.2 |
| *Enterococcus faecalis* | genomic DNA | CP022312.1 |
| *Pseudomonas parafulva* | genomic DNA | CP019952.1 |
| *Pseudomonas cremoricolorata* | genomic DNA | CP009455.1 |
| *Pseudomonas monteilii* | genomic DNA | CP013997.1 |
| *Pseudomonas* sp. SNU WT1 | genomic DNA | CP035952.1 |
| *Pseudomonas alkylphenolica* | genomic DNA | CP009048.1 |
| *Pseudomonas* sp. DG56-2 | genomic DNA | CP032311.1 |
| *Pseudomonas* sp. HLS-6 | genomic DNA | CP024478.1 |
| *Pseudomonas rhizosphaerae* | genomic DNA | CP009533.1 |
| *Pseudomonas viridiflava* | chromosomal DNA | LT855380.1 |
| *Pseudomonas cichorii* | genomic DNA | CP007039.1 |
| *Pseudomonas chloroaphis* | genomic DNA | CP027707.1 |
| *Pseudomonas chloroaphis* | chromosomal DNA | LT629761.1 |
| *Pseudomonas* sp. MRSN12121 | genomic DNA | CP010892.1 |
| *Pseudomonas fluorescens* | genomic DNA | CP012830.1 |
| *Pseudomonas frederiksbergensis* | genomic DNA | CP017886.1 |
| *Pseudomonas chloroaphis* | genomic DNA | CP011110.1 |
| *Pseudomonas chloroaphis* | genomic DNA | CP027744.1 |
| *Pseudomonas* sp. ATCC 43928 | genomic DNA | CP041753.1 |
| *Pseudomonas frederiksbergensis* | genomic DNA | CP023466.1 |
| *Pseudomonas* sp. GR 6-02 | genomic DNA | CP011567.1 |
| *Pseudomonas chloroaphis* | genomic DNA | CP027718.1 |
| *Pseudomonas chloroaphis* | genomic DNA | CP027717.1 |
| *Pseudomonas chloroaphis* | genomic DNA | CP027746.1 |
| *Pseudomonas chloroaphis* | genomic DNA | CP027743.1 |
| *Pseudomonas syringae* | genomic DNA | CP032631.1 |
| *Pseudomonas syringae* | genomic DNA | CP032871.1 |
| *Pseudomonas avellanae* | genomic DNA | CP026562.1 |
| *Pseudomonas syringae* | chromosomal DNA | LT963408.1 |
| *Pseudomonas syringae* | genomic DNA | CP024712.1 |
| *Pseudomonas syringae* | genomic DNA | CP019732.1 |
| *Pseudomonas syringae* | genomic DNA | CP019730.1 |

In one aspect, the DNA constructs disclosed herein incorporate a gene that expresses hydrogenase. Hydrogenase is a protein that catalyzes the reversible oxidation of molecular hydrogen. Numerous hydrogenases are recognized including [NiFe] hydrogenases, [NiFeSe] hydrogenases, [FeFe] hydrogenases, and [Fe]-only hydrogenases, where the chemical symbols in brackets indicate the metal ions at the catalytic centers of the protein.

In one aspect, the gene that expresses hydrogenase is isolated from a bacterium. In another aspect, the bacterium can be selected from *Burkholderia pseudomallei*, *Burkholderia thailandensis*, *Burkholderia oklahomensis*, or another *Burkholderia* species, *Acidithiobacillus ferridurans*, *Acidithiobacillus ferrivorans*, *Acidithiobacillus ferrooxidans*, *Acidithiobacillus caldus*, a *Paraburkholderia* species, a *Leptospirillum* species, a *Thiomonas* species, *Rhodoferax antarcticus*, *Azoarcus aromaticum*, *Sulfuricella denitrificans*, *Variovorax* sp. HS608, *Candidatus symbiobacter mobilis*, *Azoarcus* sp. DN11, *Acidiferrobacter* sp. SPIII_3, *Rugosibacter aromaticivorans*, *Cupriavidus metallidurans*, *Sideroxydans lithotrophicus*, *Ralstonia syzygii*, *Rhodoferax ferrireducens*, *Sulfuritalea hydrogenivorans*, *Azoarcus* sp. KH32C, *Polaromonas* sp. JS666, *Cupriavidus oxalaticus*, *Ralstonia eutropha*, *Ralstonia pickettii*, *Cupriavidus necator*, *Variovorax paradoxus*, *Gallionella capsiferriformans*, *Burkholderiales bacterium* GJ-E10, or an uncultured bacterium. In a further aspect, the gene that expresses hydrogenase has SEQ ID NO. 4 or at least 70% homology thereto, at least 75% homology thereto, at least 80% homology thereto, at least 85% homology thereto, at least 90% homology thereto, at least 95% homology thereto, or at least 99% homology thereto.

Other sequences expressing hydrogenase or related or homologous genes can be identified in a database such as, for example, GenBank. In one aspect, the gene that expresses hydrogenase is isolated from *Acidithiobacillus ferridurans* and can be identified by the GI number AP018795.1 in the GenBank database. In another aspect, sequences useful herein include those with the GI numbers listed in Table 4:

TABLE 4

Hydrogenase Genes

| Source Organism | Sequence Description | GI Number |
|---|---|---|
| *Acidithiobacillus ferridurans* | genomic DNA | AP018795.1 |
| *Acidithiobacillus ferrivorans* | genomic DNA | LT841305.1 |
| *Acidithiobacillus ferrivorans* | genomic DNA | CP002985.1 |
| *Acidithiobacillus ferrooxidans* | genomic DNA | CP001219.1 |
| *Acidithiobacillus ferrooxidans* | genomic DNA | CP001132.1 |
| *Acidithiobacillus caldus* | genomic DNA | CP005986.1 |
| *Acidithiobacillus caldus* | genomic DNA | CP002573.1 |
| *Acidithiobacillus caldus* | genomic DNA | CP026328.1 |
| *Cupriavidus necator* | genomic DNA | CP002879.1 |
| *Variovorax paradoxus* | genomic DNA | CP003912.1 |
| *Gallionella capsiferriformans* | genomic DNA | CP002159.1 |
| Uncultured bacterium | CRISPR-Cas system sequence | KU516114.1 |
| *Burkholderia* sp. HB1 | genomic DNA | CP012193.1 |
| *Burkholderiales bacterium* GJ-E10 | genomic DNA | AP014683.1 |
| Uncultured bacterium | genomic DNA | KX576128.1 |
| *Cupriavidus necator* | genomic DNA | CP039287.1 |
| *Paraburkholderia xenovorans* | genomic DNA | CP008761.1 |
| *Ralstonia pickettii* | genomic DNA | CP006667.1 |
| *Ralstonia eutropha* | genomic DNA | AM260479.1 |
| *Paraburkholderia xenovorans* | genomic DNA | CP000272.1 |
| *Cupriavidus oxalaticus* | genomic DNA | CP038636.1 |
| *Paraburkholderia terricola* | genomic DNA | CP024941.1 |
| *Polaromonas* sp. JS666 | genomic DNA | CP000316.1 |
| *Paraburkholderia aromaticivorans* | genomic DNA | CP022991.1 |
| *Paraburkholderia* sp. 7MH5 | plasmid DNA | CP038152.1 |
| *Azoarcus* sp. KH32C | genomic DNA | AP012304.1 |
| *Sulfuritalea hydrogenivorans* | genomic DNA | AP012547.1 |
| *Paraburkholderia xenovorans* | genomic DNA | CP008762.1 |
| *Paraburkholderia xenovorans* | genomic DNA | CP000271.1 |
| *Rhodoferax ferrireducens* | genomic DNA | CP000267.1 |
| *Ralstonia syzygii* | genomic DNA | FR854086.1 |
| *Sideroxydans lithotrophicus* | genomic DNA | CP001965.1 |
| *Cupriavidus metallidurans* | megaplasmid DNA | CP000353.2 |
| *Paraburkholderia* sp. DCR13 | chromosomal DNA | CP029641.1 |
| *Rugosibacter aromaticivorans* | genomic DNA | CP010554.1 |
| *Paraburkholderia hospital* | chromosomal DNA | CP024939.1 |
| *Acidiferrobacter* sp. SPIII 3 | chromosomal DNA | CP027663.1 |
| *Paraburkholderia hospital* | chromosomal DNA | CP026107.1 |
| *Paraburkholderia caribensis* | chromosomal DNA | CP012747.1 |
| *Azoarcus* sp. DN11 | genomic DNA | CP021731.1 |
| *Burkholderia thailandensis* | chromosomal DNA | CP023498.1 |
| *Candidatus symbiobacter mobilis* | genomic DNA | CP004885.1 |
| *Burkholderia thailandensis* | chromosomal DNA | CP004096.1 |
| *Paraburkholderia phymatum* | plasmid DNA | CP001045.1 |
| *Variovorax* sp. HS608 | chromosomal DNA | LT607803.1 |
| *Sulfuricella denitrificans* | genomic DNA | AP013066.1 |
| *Burkholderia* sp. Bp5365 | chromosomal DNA | CP013382.1 |
| *Burkholderia* sp. 2002721687 | chromosomal DNA | CP009548.1 |
| *Thiomonas* sp. Str. 3As | chromosomal DNA | FP475956.1 |
| *Paraburkholderia caribensis* | chromosomal DNA | CP026103.1 |
| *Paraburkholderia caribensis* | chromosomal DNA | CP013349.1 |
| *Paraburkholderia caribensis* | plasmid DNA | CP013104.1 |
| *Thiomonas intermedia* | genomic DNA | CP002021.1 |
| *Burkholderia oklahomensis* | chromosomal DNA | CP013359.1 |
| *Burkholderia oklahomensis* | chromosomal DNA | CP009556.1 |
| *Thiomonas* sp. CB2 | genome assembly scaffold DNA | LK931600.1 |
| *Azoarcus aromaticum* | genomic DNA | CR555306.1 |
| *Burkholderia* sp. DHOD12 | chromosomal DNA | CP040077.1 |
| *Burkholderia thailandensis* | chromosomal DNA | CP020391.1 |
| *Burkholderia thailandensis* | chromosomal DNA | CP013410.1 |
| *Burkholderia thailandensis* | chromosomal DNA | CP004090.1 |
| *Leptospirillum ferriphilum* | genomic DNA | CP002919.1 |
| *Rhodoferax antarcticus* | genomic DNA | CP019240.1 |
| *Burkholderia thailandensis* | chromosomal DNA | CP013361.1 |
| *Burkholderia thailandensis* | chromosomal DNA | CP008915.2 |
| *Burkholderia thailandensis* | chromosomal DNA | CP022216.1 |
| *Burkholderia thailandensis* | chromosomal DNA | CP022215.1 |
| *Burkholderia thailandensis* | chromosomal DNA | CP020389.1 |
| *Burkholderia thailandensis* | chromosomal DNA | CP013413.1 |
| *Burkholderia thailandensis* | chromosomal DNA | CP010018.1 |
| *Burkholderia thailandensis* | chromosomal DNA | CP009602.1 |
| *Burkholderia thailandensis* | chromosomal DNA | CP004382.1 |
| *Burkholderia thailandensis* | chromosomal DNA | CP008786.1 |
| *Burkholderia thailandensis* | chromosomal DNA | CP004384.1 |
| *Burkholderia thailandensis* | chromosomal DNA | CP004118.1 |
| *Burkholderia thailandensis* | chromosomal DNA | CP004098.1 |
| *Burkholderia thailandensis* | chromosomal DNA | CP000085.1 |
| *Burkholderia* sp. BDU8 | chromosomal DNA | CP013388.1 |
| *Leptospirillum* sp. Group II CF-1 | genomic DNA | CP012147.1 |
| *Leptospirillum ferriphilum* | genomic DNA | CP007243.1 |
| *Burkholderia thailandensis* | chromosomal DNA | CP013408.1 |
| *Burkholderia thailandensis* | chromosomal DNA | CP004386.1 |
| *Burkholderia pseudomallei* | chromosomal DNA | CP041221.1 |
| *Burkholderia pseudomallei* | chromosomal DNA | CP041219.1 |
| *Burkholderia pseudomallei* | chromosomal DNA | CP040551.1 |
| *Burkholderia pseudomallei* | chromosomal DNA | CP040532.1 |
| *Burkholderia pseudomallei* | chromosomal DNA | CP038806.1 |
| *Burkholderia pseudomallei* | chromosomal DNA | CP038194.1 |
| *Burkholderia pseudomallei* | chromosomal DNA | CP037969.1 |
| *Burkholderia pseudomallei* | chromosomal DNA | CP037971.1 |
| *Burkholderia pseudomallei* | chromosomal DNA | CP037975.1 |
| *Burkholderia pseudomallei* | chromosomal DNA | CP037973.1 |
| *Burkholderia pseudomallei* | chromosomal DNA | CP037757.1 |
| *Burkholderia pseudomallei* | chromosomal DNA | CP037759.1 |
| *Burkholderia pseudomallei* | chromosomal DNA | CP036451.1 |
| *Burkholderia pseudomallei* | chromosomal DNA | CP036453.1 |
| *Burkholderia pseudomallei* | chromosomal DNA | CP033704.1 |
| *Burkholderia pseudomallei* | chromosomal DNA | CP033706.1 |
| *Burkholderia pseudomallei* | chromosomal DNA | CP033701.1 |
| *Burkholderia pseudomallei* | chromosomal DNA | CP023776.1 |

In one aspect, the DNA constructs disclosed herein include a gene that expresses a P-type ATPase. P-type ATPases are typically found in bacteria, archaea, and eukaryotes, and function as ion pumps and/or lipid pumps. P-type ATPases are also known as $E_1$-$E_2$ ATPases due to their interconversion between two forms (i.e., $E_1$ and $E_2$). P-type ATPases have a primarily α-helical structure and harness energy from ATP hydrolysis to transport a ligand across a cell membrane. Numerous P-type ATPases are recognized, typically classified into families based on affinity for particular ions (i.e., potassium, heavy metals, calcium, sodium/potassium, proton/potassium, sodium, proton, magnesium, and/or phospholipids).

In one aspect, the gene that expresses P-type ATPase is isolated from a bacterium such as, for example, *Escherichia coli*. Further in this aspect, the *E. coli* strain is selected from ECOL-18-VL-LA-PA-Ryan-0026, S17-1, KR2009, EK2009, BE104, EC-129, RRL B-1109, PigCaeca_2, PF9285, CJ236, BH212, BH214, BW25113, WCHE025970, NCTC12655, WPB121, WPB102, 4/2-1, ER1709, M217, ECCHD184, W5-6, K12 substr. MG1655, E706, 2452, MT102, 3426, T06, BR32-DEC, L53, WCHEC03503S1G0, L37, NCTC9107, NCTC0192, C600, SCEC020023, 99-3165, RTdelA_B_UU3, WCHEC005237, WCHEC005784, 51008369SK1, DA33133, VH1, H9, AR435, WCHEC050613, ME8067, J53, 26561, 675SK2, CFSAN064036, APEC 01, DTU-1, 2A, 1A, 2F_0, 4FA, 4A, 5A, 1FA, 3FA, 8A, 5FA, 7A, 7FA, 9FA, 9A, 6FA, 6A, 2_0, 8FA, 2FA, 3A, ECONIH6, LIM, CAR, CIT, SCEC020007, CRE1493, DH5alpha, AR_0015, AR_0011, CREC-532, CCREC-629, WG5, O6:H16 strain M9682-C1, O6:H16 strain F6699, F5656C1, O15:H11 strain 90-9272, O6:H16 strain 2014EL-1346-6, FDAARGOS_434, 1223, NIVEDI_C53, 360/16, O6:H16 strain 2011EL-1370-2, NCTC122, DS1, AT01, or another *E. coli* strain. In a further aspect, the gene that expresses P-type ATPase has SEQ ID NO. 5 or at least 70% homology thereto, at least 75% homology thereto, at least 80% homology thereto, at least 85% homology thereto, at least 90% homology thereto, at least 95% homology thereto, or at least 99% homology thereto.

Other sequences expressing P-type ATPase or related or homologous sequences can be identified in a database such as, for example, GenBank. In one aspect, the gene that expresses P-type ATPase is isolated from *E. coli* strain ECOL-18-VL-LA-PA-Ryan-0026 and can be identified in the GenBank database by the GI number CP041392.1. In one aspect, sequences useful herein include those with the GI numbers listed in Table 5:

TABLE 5

P-Type ATPase Genes

| Source Organism | Sequence Description | GI Number |
|---|---|---|
| *Escherichia coli* | genomic DNA | CP041392.1 |
| *Escherichia coli* | genomic DNA | CP040667.1 |
| *Escherichia coli* | genomic DNA | CP040664.1 |
| *Escherichia coli* | genomic DNA | CP040663.1 |
| *Escherichia coli* | genomic DNA | CP040643.1 |
| *Escherichia coli* | genomic DNA | CP038453.1 |
| *Escherichia coli* | genomic DNA | CP039753.1 |
| *Escherichia coli* | genomic DNA | CP038857.1 |
| *Escherichia coli* | genomic DNA | CP038791.1 |
| *Escherichia coli* | genomic DNA | CP029238.1 |
| *Escherichia coli* | genomic DNA | CP029239.1 |
| *Escherichia coli* | genomic DNA | CP029240.1 |
| *Escherichia coli* | genomic DNA | CP037857.1 |
| *Escherichia coli* | genomic DNA | CP036177.1 |
| *Escherichia coli* | genomic DNA | LR134083.1 |
| *Escherichia coli* | genomic DNA | CP034426.1 |
| *Escherichia coli* | genomic DNA | CP034428.1 |
| *Escherichia coli* | genomic DNA | CP023834.1 |
| *Escherichia coli* | genomic DNA | CP030240.1 |
| *Escherichia coli* | genomic DNA | AP019189.1 |
| *Escherichia coli* | genomic DNA | CP033250.1 |
| *Escherichia coli* | genomic DNA | CP032992.1 |
| *Escherichia coli* | genomic DNA | CP032667.1 |
| *Escherichia coli* | genomic DNA | CP029687.1 |
| *Escherichia coli* | genomic DNA | CP031833.1 |
| *Escherichia coli* | genomic DNA | CP034953.2 |
| *Escherichia coli* | genomic DNA | LS992185.1 |
| *Escherichia coli* | genomic DNA | LS992166.1 |
| *Escherichia coli* | genomic DNA | CP035350.1 |
| *Escherichia coli* | genomic DNA | CP034734.1 |
| *Escherichia coli* | genomic DNA | CP034595.1 |
| *Escherichia coli* | genomic DNA | CP034589.1 |
| *Escherichia coli* | genomic DNA | LR134240.1 |
| *Escherichia coli* | genomic DNA | LR134227.1 |
| *Escherichia coli* | genomic DNA | CP031214.1 |
| *Escherichia coli* | genomic DNA | CP025950.3 |
| *Escherichia coli* | genomic DNA | CP029981.1 |
| *Escherichia coli* | genomic DNA | CP023749.1 |
| *Escherichia coli* | genomic DNA | CP026580.2 |
| *Escherichia coli* | genomic DNA | CP028578.2 |
| *Escherichia coli* | genomic DNA | CP029973.1 |
| *Escherichia coli* | genomic DNA | CP029574.1 |
| *Escherichia coli* | genomic DNA | CP028704.1 |
| *Escherichia coli* | genomic DNA | CP029180.1 |
| *Escherichia coli* | genomic DNA | CP029115.1 |
| *Escherichia coli* | genomic DNA | CP019213.2 |
| *Escherichia coli* | genomic DNA | CP028703.1 |
| *Escherichia coli* | genomic DNA | CP028702.1 |
| *Escherichia coli* | genomic DNA | CP027118.1 |
| *Escherichia coli* | genomic DNA | CP027701.1 |
| *Escherichia coli* | genomic DNA | CP028166.1 |
| *Escherichia coli* | genomic DNA | CP028310.1 |
| *Escherichia coli* | genomic DNA | CP027060.1 |
| *Escherichia coli* | genomic DNA | CP026612.1 |
| *Escherichia coli* | genomic DNA | CP026358.1 |
| *Escherichia coli* | genomic DNA | CP026361.1 |
| *Escherichia coli* | genomic DNA | CP026357.1 |
| *Escherichia coli* | genomic DNA | CP026352.1 |
| *Escherichia coli* | genomic DNA | CP026353.1 |

TABLE 5-continued

P-Type ATPase Genes

| Source Organism | Sequence Description | GI Number |
|---|---|---|
| *Escherichia coli* | genomic DNA | CP026351.1 |
| *Escherichia coli* | genomic DNA | CP026360.1 |
| *Escherichia coli* | genomic DNA | CP026354.1 |
| *Escherichia coli* | genomic DNA | CP026345.1 |
| *Escherichia coli* | genomic DNA | CP026350.1 |
| *Escherichia coli* | genomic DNA | CP026347.1 |
| *Escherichia coli* | genomic DNA | CP026346.1 |
| *Escherichia coli* | genomic DNA | CP026342.1 |
| *Escherichia coli* | genomic DNA | CP026343.1 |
| *Escherichia coli* | genomic DNA | CP026348.1 |
| *Escherichia coli* | genomic DNA | CP026349.1 |
| *Escherichia coli* | genomic DNA | CP026359.1 |
| *Escherichia coli* | genomic DNA | CP026344.1 |
| *Escherichia coli* | genomic DNA | CP026356.1 |
| *Escherichia coli* | genomic DNA | CP026355.1 |
| *Escherichia coli* | genomic DNA | CP026199.1 |
| *Escherichia coli* | genomic DNA | CP026027.1 |
| *Escherichia coli* | genomic DNA | CP026026.1 |
| *Escherichia coli* | genomic DNA | CP026028.1 |
| *Escherichia coli* | genomic DNA | CP025627.1 |
| *Escherichia coli* | genomic DNA | CP019071.1 |
| *Escherichia coli* | genomic DNA | CP025520.1 |
| *Escherichia coli* | genomic DNA | CP025268.1 |
| *Escherichia coli* | genomic DNA | CP024859.1 |
| *Escherichia coli* | genomic DNA | CP024855.1 |
| *Escherichia coli* | genomic DNA | CP024830.1 |
| *Escherichia coli* | genomic DNA | CP024815.1 |
| *Escherichia coli* | genomic DNA | CP024090.1 |
| *Escherichia coli* | genomic DNA | CP024275.1 |
| *Escherichia coli* | genomic DNA | CP024266.1 |
| *Escherichia coli* | genomic DNA | CP024260.1 |
| *Escherichia coli* | genomic DNA | CP024239.1 |
| *Escherichia coli* | genomic DNA | CP024232.1 |
| *Escherichia coli* | genomic DNA | CP023870.1 |
| *Escherichia coli* | genomic DNA | CP023383.1 |
| *Escherichia coli* | genomic DNA | CP017061.1 |
| *Escherichia coli* | genomic DNA | CP023201.1 |
| *Escherichia coli* | genomic DNA | CP022912.1 |
| *Escherichia coli* | genomic DNA | LT906474.1 |
| *Escherichia coli* | genomic DNA | CP022466.1 |
| *Escherichia coli* | genomic DNA | CP022414.1 |

In one aspect, the DNA construct has the following genetic components: a) a gene that expresses a heat shock protein, b) a gene that expresses RuBisCO large subunit 1, c) a gene that expresses tonB, d) a gene that expresses hydrogenase, and e) a gene that expresses P-type ATPase.

In one aspect, the DNA constructs disclosed herein optionally include a gene that expresses dehydrogenase. The gene that expresses hydrogenase can be positioned before or after any of the genetic components used to produce the constructs described herein. In another aspect, a dehydrogenase catalyzes the removal of hydrogen atoms from a particular molecule, including, but not limited to, molecules involved in the electron transport chain reactions of cellular respiration or in anaerobic and other non-standard energy-generation metabolisms, particularly in conjunction with coenzymes such as, for example, nicotinamide adenine dinucleotide (NAD), flavin adenine dinucleotide (FAD), or flavin mononucleotide (FMN). In a further aspect, dehydrogenases are classified as oxidoreductases. In some aspects, the dehydrogenases disclosed herein are quinoproteins that use pyrrolo-quinoline quinone (also known as methoxatin) as a redox cofactor. In a further aspect, the dehydrogenases disclosed herein can stimulate bacterial growth. In a still further aspect, a dehydrogenase oxidizes its substrate by transferring a hydrogen to an electron acceptor.

In one aspect, the gene that expresses dehydrogenase is isolated from a bacterium such as, for example, *Acidithio-* bacillus ferrooxidans or another Acidithiobacillus species. In another aspect, the bacterium can be a Chloroflexi species, a Dehalococcoidia species, a Microbispora species, a Spirochaetes species, an Acidobacteria species, a Deltaproteobacteria species, an Ardenticatena species, an Anaerolina species, an Arthospira species, a Methanothermobacter species, a Xanthomonas species, or another bacterium. In another aspect, the gene that expresses dehydrogenase is isolated from an archaeon. In a further aspect, the archaeon is a Halorubrum species, a Natronorubrum species, a Natronobacterium species, a Natronolimnobius species, a Halopiger species, a Thermoplasmata species, a Bathyarchaeota species, a Halorhabdus species, a Halonotius species, a Methanolinea species, a Thermococcus species, a Hadesarchaea species, a Halostella species, a Salinarchaeum species, or another archaeon. In one aspect, the bacterium or archaeon is an extremophile such as an acidophile, halophile, or thermophile, or a combination thereof. In another aspect, the bacterium or archaeon is autotrophic (such as, for example, a cyanobacterium) or has a non-standard metabolism such as, for example, a methanogenic, organohalide respiration, a sulfate- and/or sulfur-reducing metabolism, or the like. In one aspect, the gene that expresses dehydrogenase is isolated from a primate such as, for example, a human or a golden snub-nosed monkey, a plant such as, for example, soybean, or a virus such as, for example, Rubella virus or hepatitis C virus. In a further aspect, the gene that expresses dehydrogenase has SEQ ID NO. 9 or at least 70% homology thereto, at least 75% homology thereto, at least 80% homology thereto, at least 85% homology thereto, at least 90% homology thereto, at least 95% homology thereto, or at least 99% homology thereto.

Other sequences expressing dehydrogenase or related or homologous sequences can be identified in a database such as, for example, GenBank. In one aspect, the gene that expresses dehydrogenase is isolated from A. ferrooxidans and the dehydrogenase protein can be identified in the GenBank database by the GI number CP040511.1. In one aspect, sequences useful herein include those with the GI numbers listed in Table 6:

TABLE 6

Dehydrogenase Genes

| Source Organism | Sequence Description | GI Number |
|---|---|---|
| Acdithiobacillus sp. "AMD consortium" | genomic DNA | CP044411.1 |
| Acidithiobacillus ferridurans | genomic DNA | AP018795.1 |
| Acidithiobacillus ferrooxidans | genomic DNA | CP040511.1 |
| Acidithiobacillus ferrooxidans | genomic DNA | CP001219.1 |
| Acidithiobacillus ferrooxidans | genomic DNA | CP001132.1 |
| Sphingomonas sp. Cra20 | genomic DNA | CP024924.1 |
| Pseudomonas rhodesiae | genomic DNA | CP054205.1 |
| Rhinopithecus roxellana | dispatched RND transporter family member 3 | XM_010353518.2 |
| Scophthalmus maximus | genomic DNA | CP026246.1 |
| Rhinopithecus bieti | genomic DNA | XM_017866453.1 |
| Rubella virus | E1 protein gene | KU884920.1 |
| Rubella virus | E1 protein gene | KU884918.1 |
| Streptomyces sp. Jing01 | genomic DNA | CP053189.1 |
| Neptunomonas concharum | genomic DNA | CP043869.1 |
| Pigmentiphaga sp. H8 | genomic DNA | CP033966.1 |
| Zobellia galactanivorans | genomic DNA | FP476056.1 |
| Homo sapiens | genomic DNA | AC108734.10 |
| Crassostrea gigas | integrator complex subunit 13 | XM_034450993.1 |

TABLE 6-continued

Dehydrogenase Genes

| Source Organism | Sequence Description | GI Number |
|---|---|---|
| Crassostrea gigas | integrator complex subunit 13 | XM_034450992.1 |
| Crassostrea gigas | integrator complex subunit 13 | XM_034450991.1 |
| Lutra lutra | genomic DNA | LR738418.1 |
| Aeromonas schubertii | genomic DNA | CP039611.1 |
| Xanthomonas hortorum | genomic DNA | CP016878.1 |
| Xanthomonas hortorum | genomic DNA | CP018731.1 |
| Xanthomonas hortorum | genomic DNA | CP018728.1 |
| Aeromonas schubertii | genomic DNA | CP013067.1 |
| Acomys russatus | genomic DNA | LR877214.1 |
| Xanthomonas hortorum | genomic DNA | LR828264.1 |
| Xanthomonas hortorum | genomic DNA | LR828257.1 |
| Xanthomonas gardneri | genomic DNA | LR828253.1 |
| Xanthomonas cynarae | genomic DNA | LR828251.1 |
| Hepatitis C virus | polyprotein gene | HQ318852.1 |
| Hepatitis C virus | polyprotein gene | HQ318842.1 |
| Hepatitis C virus | polyprotein gene | HQ318841.1 |
| Glycine max | genomic DNA | AC235463.1 |
| Glycine max | genomic DNA | AC235121.1 |
| Hepatitis C virus | polyprotein gene, E1-E2 region | AM271579.1 |
| Hepatitis C virus | polyprotein gene, E1-E2 region | AM271511.1 |
| Synthetic construct | envelope glycoprotein gene | EF043090.1 |

In another aspect, said construct further includes a) a promoter, b) a terminator or stop sequence, c) a gene that confers resistance to an antibiotic (a "selective marker"), d) a reporter protein, or any combination thereof.

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In another aspect, the coding sequence to be controlled is located 3' to the promoter. In still another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter also may be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, araBAD promoter, and GAL1 promoter. In a further aspect, the promoter is a native part of the vector used herein. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides from a ribosomal binding site.

In one aspect, the promoter is a GAL1 promoter. In another aspect, the GAL1 promoter is native to the plasmid used to create the vector. In another aspect, a GAL1 promoter is positioned before the gene that expresses hydrogenase, the gene that expresses P-type ATPase, the gene that expresses tonB, the gene that expresses a heat shock protein, the gene that expresses RuBisCO large subunit 1, or any combination thereof. In another aspect, the promoter is a GAL1 promoter obtained from or native to the pYES2 plasmid.

In another aspect, the promoter is an araBAD promoter. In a further aspect, the araBAD promoter is native to the plasmid used to create the vector. In still another aspect, an araBAD promoter is positioned before the gene that expresses a heat shock protein, the gene that expresses RuBisCO large subunit 1, the gene that expresses tonB, the gene that expresses hydrogenase, the gene that expresses P-type ATPase, or any combination thereof. In one aspect, the araBAD promoter is positioned before the gene that expresses hydrogenase. In another aspect, the promoter is an araBAD promoter obtained from or native to the pBAD plasmid.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/DNA/RNA polymerase complex. In one aspect, the terminator is an rrnB terminator obtained from or native to the pBAD plasmid. In an alternative aspect, the terminator is a CYC1 terminator obtained from or native to the pYES2 plasmid.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In another aspect, the vector contains one or more ribosomal binding sites. As used herein, a "ribosomal binding site" is a sequence of nucleotides located 5' to the start codon of an mRNA that recruits a ribosome to initiate protein translation. In one aspect, the ribosomal binding site can be positioned before one or more or all genes in the DNA construct, or a before a subset of genes in a DNA construct.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BasBI, NotI, XhoI, XphI, XbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA at a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior insertion into the plasmid. In a further aspect, a DNA ligase enzyme can be used to assist in the ligation process.

In another aspect, the ligation mix may be incubated in an electromagnetic chamber. In one aspect, the incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and commercially available. Such vectors include, but are not limited to, pWLneo, pSV2cat, pOG44, pXT1, pSG, pSVK3, pBSK, pYES, pYES2, pBSKII, pUC, pUC19, pBAD, and pETDuet-1 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copier per host cell and will contain selectable markers (such as genes for antibiotic resistance) to show the skilled artisan to select host eels that have been successfully transfected with the plasmids (for example, by growing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector, which confers antibiotic resistance, can survive. Optimally, only cells containing the vector to be expressed will be cultured, as this will result in the highest production efficiency of the desired gene products (e.g., peptides). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 6 or at least 70% homology thereto. The amount of fluorescence that is produced can be correlated to the amount of DNA incorporated into the transfected cells. The fluorescence produced can be detected and quantified using techniques known in the art. For example, spectrofluorometers are typically used to measure fluorescence.

The DNA construct described herein can be part of a vector. In one aspect, the vector is a plasmid, a phagemid, a cosmid, a yeast artificial chromosome, a bacterial artificial chromosome, a virus, a phage, or a transposon.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the methods described below.

In one aspect, the construct includes from 5' to 3' the following genetic components in the following order: (1) a gene that expresses a heat shock protein, (2) a gene that expresses RuBisCO large subunit 1, (3) a gene that expresses tonB, (4) a gene that expresses hydrogenase, and (5) a gene that expresses P-type ATPase.

In one aspect, the construct includes from 5' to 3' the following genetic components in the following order: a gene that expresses a heat shock protein having SEQ ID NO. 1 or at least 70% homology thereto, a gene that expresses RuBisCO large subunit 1 having SEQ ID NO. 2 or at least 70% homology thereto, a gene that expresses tonB having SEQ ID NO. 3 or at least 70% homology thereto, a gene that expresses hydrogenase having SEQ ID NO. 4 or at least 70% homology thereto, and a gene that expresses P-type ATPase having SEQ ID NO. 5 or at least 70% homology thereto.

In another aspect, the construct includes from 5' to 3' the following genetic components in the following order: (1) a gene that expresses a heat shock protein, (2) a gene that expresses RuBisCO large subunit 1, (3) a gene that expresses tonB, (4) an rrnB terminator, (5) an araBAD promoter, (6) a gene that expresses hydrogenase, and (7) a gene that expresses P-type ATPase.

In another aspect, the construct includes from 5' to 3' the following genetic components in the following order: (1) a gene that expresses a heat shock protein having SEQ ID NO. 1 or at least 90% homology thereto, (2) a gene that expresses RuBisCO large subunit 1 having SEQ ID NO. 2 or at least 90% homology thereto, (3) a gene that expresses tonB having SEQ ID NO. 3 or at least 90% homology thereto, (4) an rrnB terminator, (5) an araBAD promoter, (6) a gene that expresses hydrogenase having SEQ ID NO. 4 or at least 90% homology thereto, and (7) a gene that expresses P-type ATPase having SEQ ID NO. 5 or at least 90% homology thereto.

In still another aspect, the construct is a pBAD plasmid having from 5' to 3' the following genetic components in the following order: (1) a gene that expresses a heat shock protein having SEQ ID NO. 1 or at least 70% homology thereto, (2) a gene that expresses RuBisCO large subunit 1 having SEQ ID NO. 2 or at least 70% homology thereto, (3) a gene that expresses tonB having SEQ ID NO. 3 or at least 70% homology thereto, (4) an rrnB terminator, (5) an araBAD promoter, (6) a gene that expresses hydrogenase having SEQ ID NO. 4 or at least 70% homology thereto, and (7) a gene that expresses P-type ATPase having SEQ ID NO. 5 or at least 70% homology thereto.

In still another aspect, the construct is a pBAD plasmid having from 5' to 3' the following genetic components in the following order: (1) a gene that expresses a heat shock protein having SEQ ID NO. 1 or at least 70% homology thereto, (2) a gene that expresses RuBisCO large subunit 1 having SEQ ID NO. 2 or at least 70% homology thereto, (3) a gene that expresses tonB having SEQ ID NO. 3 or at least 70% homology thereto, (4) an rrnB terminator, (5) an araBAD promoter, (6) a gene that expresses hydrogenase having SEQ ID NO. 4 or at least 70% homology thereto, (7) a gene that expresses P-type ATPase having SEQ ID NO. 5 or at least 70% homology thereto, and (8) a gene that expresses a reporter protein having SEQ ID NO. 6 or at least 70% homology thereto.

In another aspect, the DNA construct has SEQ ID NO. 7 or at least 70% homology thereto, at least 75% homology thereto, at least 80% homology thereto, at least 85% homology thereto, at least 90% homology thereto, at least 95% homology thereto, or at least 99% homology thereto.

In one aspect, the construct includes from 5' to 3' the following genetic components in the following order: a gene that expresses a heat shock protein having SEQ ID NO. 1 or at least 70% homology thereto, a gene that expresses dehydrogenase having SEQ ID NO. 9 or at least 70% homology thereto, a gene that expresses RuBisCO large subunit 1 having SEQ ID NO. 2 or at least 70% homology thereto, a gene that expresses tonB having SEQ ID NO. 3 or at least 70% homology thereto, a gene that expresses hydrogenase having SEQ ID NO. 4 or at least 70% homology thereto, and a gene that expresses P-type ATPase having SEQ ID NO. 5 or at least 70% homology thereto.

In another aspect, the construct includes from 5' to 3' the following genetic components in the following order: (1) a gene that expresses a heat shock protein, (2) a gene that expresses a dehydrogenase, (3) a gene that expresses RuBisCO large subunit 1, (4) a gene that expresses tonB, (5) an rrnB terminator, (6) an araBAD promoter, (7) a gene that expresses hydrogenase, and (8) a gene that expresses P-type ATPase.

In another aspect, the construct includes from 5' to 3' the following genetic components in the following order: (1) a gene that expresses a heat shock protein having SEQ ID NO. 1 or at least 90% homology thereto, (2) a gene that expresses dehydrogenase having SEQ ID NO. 9 or at least 90% homology thereto, (3) a gene that expresses RuBisCO large subunit 1 having SEQ ID NO. 2 or at least 90% homology thereto, (4) a gene that expresses tonB having SEQ ID NO. 3 or at least 90% homology thereto, (5) an rrnB terminator, (6) an araBAD promoter, (7) a gene that expresses hydrogenase having SEQ ID NO. 4 or at least 90% homology thereto, and (8) a gene that expresses P-type ATPase having SEQ ID NO. 5 or at least 90% homology thereto.

In still another aspect, the construct is a pBAD plasmid having from 5' to 3' the following genetic components in the following order: (1) a gene that expresses a heat shock protein having SEQ ID NO. 1 or at least 70% homology thereto, (2) a gene that expresses dehydrogenase having SEQ ID NO. 9 or at least 70% homology thereto, (3) a gene that expresses RuBisCO large subunit 1 having SEQ ID NO. 2 or at least 70% homology thereto, (4) a gene that expresses tonB having SEQ ID NO. 3 or at least 70% homology thereto, (5) an rrnB terminator, (6) an araBAD promoter, (7) a gene that expresses hydrogenase having SEQ ID NO. 4 or at least 70% homology thereto, and (8) a gene that expresses P-type ATPase having SEQ ID NO. 5 or at least 70% homology thereto.

In still another aspect, the construct is a pBAD plasmid having from 5' to 3' the following genetic components in the following order: (1) a gene that expresses a heat shock protein having SEQ ID NO. 1 or at least 70% homology thereto, (2) a gene that expresses dehydrogenase having SEQ ID NO. 9 or at least 70% homology thereto, (3) a gene that expresses RuBisCO large subunit 1 having SEQ ID NO. 2 or at least 70% homology thereto, (4) a gene that expresses tonB having SEQ ID NO. 3 or at least 70% homology thereto, (5) an rrnB terminator, (6) an araBAD promoter, (7) a gene that expresses hydrogenase having SEQ ID NO. 4 or at least 70% homology thereto, (8) a gene that expresses P-type ATPase having SEQ ID NO. 5 or at least 70% homology thereto, and (9) a gene that expresses a reporter protein having SEQ ID NO. 6 or at least 70% homology thereto.

In another aspect, the DNA construct has SEQ ID NO. 11 or at least 70% homology thereto, at least 75% homology thereto, at least 80% homology thereto, at least 85% homology thereto, at least 90% homology thereto, at least 95% homology thereto, or at least 99% homology thereto.

In one aspect, the construct includes from 5' to 3' the following genetic components in the following order: (1) a gene that expresses hydrogenase, (2) a gene that expresses P-type ATPase, (3) a gene that expresses tonB, (4) a gene that expresses a heat shock protein, and (5) a gene that expresses RuBisCO large subunit 1.

In one aspect, the construct includes from 5' to 3' the following genetic components in the following order: a gene that expresses hydrogenase having SEQ ID NO. 4 or at least 70% homology thereto, a gene that expresses P-type ATPase having SEQ ID NO. 5 or at least 70% homology thereto, a gene that expresses tonB having SEQ ID NO. 3 or at least 70% homology thereto, a gene that expresses a heat shock protein having SEQ ID NO. 1 or at least 70% homology thereto, and a gene that expresses RuBisCO large subunit 1 having SEQ ID NO. 2 or at least 70% homology thereto.

In another aspect, the construct includes from 5' to 3' the following genetic components in the following order: (1) a gene that expresses hydrogenase, (2) a CYC1 terminator, (3) a GAL1 promoter, (4) a gene that expresses P-type ATPase, (5) a CYC1 terminator, (6) a GAL1 promoter, (7) a gene that expresses tonB, (8) a CYC1 terminator, (9) a GAL1 promoter, (10) a gene that expresses a heat shock protein, (11) a CYC1 terminator, (12) a GAL1 promoter, (13) a gene that expresses RuBisCO large subunit 1, and (14) a CYC1 terminator.

In another aspect, the construct includes from 5' to 3' the following genetic components in the following order: (1) a gene that expresses hydrogenase having SEQ ID NO. 4 or at least 90% homology thereto, (2) a CYC1 terminator, (3) a GAL1 promoter, (4) a gene that expresses P-type ATPase having SEQ ID NO. 5 or at least 90% homology thereto, (5) a CYC1 terminator, (6) a GAL1 promoter, (7) a gene that expresses tonB having SEQ ID NO. 3 or at least 90% homology thereto, (8) a CYC1 terminator, (9) a GAL1 promoter, (10) a gene that expresses a heat shock protein having SEQ ID NO. 1 or at least 90% homology thereto, (11) a CYC1 terminator, (12) a GAL1 promoter, (13) a gene that expresses RuBisCO large subunit 1 having SEQ ID NO. 2 or at least 90% homology thereto, and (14) a CYC1 terminator.

In still another aspect, the construct is a pYES2 plasmid having from 5' to 3' the following genetic components in the following order: (1) a gene that expresses hydrogenase having SEQ ID NO. 4 or at least 70% homology thereto, (2) a CYC1 terminator, (3) a GAL1 promoter, (4) a gene that expresses P-type ATPase having SEQ ID NO. 5 or at least 70% homology thereto, (5) a CYC1 terminator, (6) a GAL1 promoter, (7) a gene that expresses tonB having SEQ ID NO. 3 or at least 70% homology thereto, (8) a CYC1 terminator, (9) a GAL1 promoter, (10) a gene that expresses a heat shock protein having SEQ ID NO. 1 or at least 70% homology thereto, (11) a CYC1 terminator, (12) a GAL1 promoter, (13) a gene that expresses RuBisCO large subunit 1 having SEQ ID NO. 2 or at least 70% homology thereto, and (14) a CYC1 terminator.

In still another aspect, the construct is a pYES2 plasmid having from 5' to 3' the following genetic components in the following order: (1) a gene that expresses hydrogenase having SEQ ID NO. 4 or at least 70% homology thereto, (2) a CYC1 terminator, (3) a GAL1 promoter, (4) a gene that expresses P-type ATPase having SEQ ID NO. 5 or at least 70% homology thereto, (5) a CYC1 terminator, (6) a GAL1 promoter, (7) a gene that expresses tonB having SEQ ID NO. 3 or at least 70% homology thereto, (8) a CYC1 terminator, (9) a GAL1 promoter, (10) a gene that expresses a heat shock protein having SEQ ID NO. 1 or at least 70% homology thereto, (11) a CYC1 terminator, (12) a GAL1 promoter, (13) a gene that expresses RuBisCO large subunit 1 having SEQ ID NO. 2 or at least 70% homology thereto, (14) a CYC1 terminator, (15) a GAL1 promoter, and (16) a gene that expresses a reporter protein having SEQ ID NO. 6 or at least 70% homology thereto.

In another aspect, the DNA construct has SEQ ID NO. 8 or at least 70% homology thereto, at least 75% homology thereto, at least 80% homology thereto, at least 85% homology thereto, at least 90% homology thereto, at least 95% homology thereto, or at least 99% homology thereto.

In one aspect, the construct includes from 5' to 3' the following genetic components in the following order: (1) a gene that expresses hydrogenase, (2) a gene that expresses P-type ATPase, (3) a gene that expresses tonB, (4) a gene that expresses a heat shock protein, (5) a gene that expresses dehydrogenase, and (6) a gene that expresses RuBisCO large subunit 1.

In one aspect, the construct includes from 5' to 3' the following genetic components in the following order: a gene that expresses hydrogenase having SEQ ID NO. 4 or at least 70% homology thereto, a gene that expresses P-type ATPase having SEQ ID NO. 5 or at least 70% homology thereto, a gene that expresses tonB having SEQ ID NO. 3 or at least 70% homology thereto, a gene that expresses a heat shock protein having SEQ ID NO. 1 or at least 70% homology thereto, a gene that expresses dehydrogenase having SEQ ID NO. 9 or at least 70% homology thereto, and a gene that expresses RuBisCO large subunit 1 having SEQ ID NO. 2 or at least 70% homology thereto.

In another aspect, the construct includes from 5' to 3' the following genetic components in the following order: (1) a gene that expresses hydrogenase, (2) a CYC1 terminator, (3) a GAL1 promoter, (4) a gene that expresses P-type ATPase, (5) a CYC1 terminator, (6) a GAL1 promoter, (7) a gene that expresses tonB, (8) a CYC1 terminator, (9) a GAL1 promoter, (10) a gene that expresses a heat shock protein, (11) a CYC1 terminator, (12) a GAL1 promoter, (13) a gene that expresses dehydrogenase, (14) a CYC1 terminator, (15) a GAL1 promoter, and (16) a gene that expresses a gene that expresses RuBisCO large subunit 1.

In another aspect, the construct includes from 5' to 3' the following genetic components in the following order: (1) a gene that expresses hydrogenase having SEQ ID NO. 4 or at least 90% homology thereto, (2) a CYC1 terminator, (3) a GAL1 promoter, (4) a gene that expresses P-type ATPase having SEQ ID NO. 5 or at least 90% homology thereto, (5) a CYC1 terminator, (6) a GAL1 promoter, (7) a gene that expresses tonB having SEQ ID NO. 3 or at least 90% homology thereto, (8) a CYC1 terminator, (9) a GAL1 promoter, (10) a gene that expresses a heat shock protein having SEQ ID NO. 1 or at least 90% homology thereto, (11) a CYC1 terminator, (12) a GAL1 promoter, (13) a gene that expresses dehydrogenase having SEQ ID NO. 9 or at least 90% homology thereto, (14) a CYC1 terminator, (15) a GAL1 promoter, and (16) a gene that expresses RuBisCO large subunit 1 having SEQ ID NO. 2 or at least 90% homology thereto.

In still another aspect, the construct is a pYES2 plasmid having from 5' to 3' the following genetic components in the following order: (1) a gene that expresses hydrogenase having SEQ ID NO. 4 or at least 70% homology thereto, (2) a CYC1 terminator, (3) a GAL1 promoter, (4) a gene that expresses P-type ATPase having SEQ ID NO. 5 or at least 70% homology thereto, (5) a CYC1 terminator, (6) a GAL1 promoter, (7) a gene that expresses tonB having SEQ ID NO. 3 or at least 70% homology thereto, (8) a CYC1 terminator, (9) a GAL1 promoter, (10) a gene that expresses a heat shock protein having SEQ ID NO. 1 or at least 70% homology thereto, (11) a CYC1 terminator, (12) a GAL1 promoter, (13) a gene that expresses dehydrogenase having SEQ ID NO. 9 or at least 70% homology thereto, (14) a CYC1 terminator, (15) a GAL1 promoter, and (16) a gene that expresses RuBisCO large subunit 1 having SEQ ID NO. 2 or at least 70% homology thereto.

In still another aspect, the construct is a pYES2 plasmid having from 5' to 3' the following genetic components in the following order: (1) a gene that expresses hydrogenase having SEQ ID NO. 4 or at least 70% homology thereto, (2) a CYC1 terminator, (3) a GAL1 promoter, (4) a gene that expresses P-type ATPase having SEQ ID NO. 5 or at least 70% homology thereto, (5) a CYC1 terminator, (6) a GAL1 promoter, (7) a gene that expresses tonB having SEQ ID NO. 3 or at least 70% homology thereto, (8) a CYC1 terminator, (9) a GAL1 promoter, (10) a gene that expresses a heat shock protein having SEQ ID NO. 1 or at least 70% homology thereto, (11) a CYC1 terminator, (12) a GAL1 promoter, (13) a gene that expresses dehydrogenase having SEQ ID NO. 9 or at least 70% homology thereto, (14) a CYC1 terminator, (15) a GAL1 promoter, (16) a gene that expresses RuBisCO large subunit 1 having SEQ ID NO. 2 or at least 70% homology thereto, (17) a CYC1 terminator, (18) a GAL1 promoter, (19) a gene that expresses a reporter protein having SEQ ID NO. 6 or at least 70% homology thereto.

In another aspect, the DNA construct has SEQ ID NO. 10 or at least 70% homology thereto, at least 75% homology thereto, at least 80% homology thereto, at least 85% homology thereto, at least 90% homology thereto, at least 95% homology thereto, or at least 99% homology thereto.

Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce a genelight solution such as, for example, those disclosed herein. "Heterologous" genes and proteins are genes and proteins that have been experimentally inserted into a cell that are not normally expressed by the cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which an exogenous nucleic acid is transferred or introduced into the host cell.

A transformed cell includes the primary subject cell and its progeny. The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

Preparation of Genelight Extracts

A satisfactory microbiological culture contains available sources of hydrogen donors and acceptors, carbon, nitrogen, sulfur, phosphorus, inorganic salts and, in certain cases, vitamins or other growth-promoting substances. For example, the addition of peptone provides a readily-available source of nitrogen and carbon. Furthermore, the use of different types of media results in different growth rates and different stationary phase densities. A rich media results in a short doubling time and higher cell density at stationary phase. Minimal media results in slow growth and low final cell densities. Efficient agitation and aeration increase final cell densities.

Culturing or fermenting of host cells can be accomplished by any technique known in the art. In one aspect, batch fermentation can be conducted. In batch fermentation, the composition of the culture medium is set at the beginning and the system is closed to future alterations. In some aspects, a limited form of batch fermentation may be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial cells are immobilized on a substrate. Fermentation may be carried out on any scale and may include methods in which literal "fermentation" is carried out as well as other culture methods that are non-fermentative.

In one aspect, the microorganisms can be cultured for a period of from 2 days to 2 weeks, or for about 2, about 3, about 4, about 5, about 6, about 7, about 8, about 9, about 10, about 11, about 12, about 13, or about 14 days, where any value can be the lower or upper endpoint of a range (e.g., about 3 days to about 13 days, about 8 days to about 12 days, etc.). In one aspect, the microorganisms are cultured for about 10 days.

In another aspect, the microorganisms can be cultured at any temperature appropriate for the microorganisms, with the understanding that the temperature may vary according to the microorganism (for example, a thermophilic microorganism may require a higher culture temperature than a mesophile). In one aspect, the microorganisms are cultured at a temperature of from about 20 to about 37° C., or are cultured at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., or about 37° C., where any value can be the lower or upper endpoint of a range, where any value can be the lower or upper endpoint of a range (e.g., about 21° C. to about 36° C., about 25° C. to about 30° C., etc.).

In certain aspects, after culturing the microorganisms for a sufficient time, the microbial cells can be lysed with one or more enzymes. For example, when the microbial cells are fungal, the fungal cells can be lysed with lyticase. In one aspect, the lyticase concentration can be about 500 μL, about 600 μL, about 700 μL, about 800 μL, about 900 μL, or about 1,000 μL per liter of culture, where any value can be the lower or upper endpoint of a range, where any value can be the lower or upper endpoint of a range (e.g., about 500 μL to about 900 μL, about 600 μL to about 800 μL, etc.).

In addition to or in place of enzymes, other components can be used to facilitate lysis of the microbial cells. In one aspect, chitosan can be used in combination with an enzyme to lyse the microbial cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation. In one aspect, the chitosan is from about 60% to about 100% acetylated, or about 70%, about 75%, about 80%, about 85%, about 90%, about 95%, or about 100% acetylated, where any value can be the lower or upper endpoint of a range, where any value can be the lower or upper endpoint of a range (e.g., about 60% to about 90%, about 70% to about 80%, etc.).

The molecular weight of the chitosan can vary, as well. For example, the chitosan can comprise about 3, 4, 5, 6, 7, 8, 9, 10, 11, 12, 13, 14, 15, 16, 17, 18, 19, or 20 glucosamine units and/or N-acetylglucosamine units, where any value can be the lower or upper endpoint of a range, where any value can be the lower or upper endpoint of a range (e.g., 2 to 19, 3 to 10, 5 to 7, etc.). In one aspect, chitosan can be added until a concentration of about 0.0015%, about 0.0025%, about 0.005%, about 0.0075%, about 0.01%, about 0.015%, about 0.02%, about 0.03%, about 0.04%, or about 0.05%, where any value can be an upper or lower endpoint of a range (e.g., 0.002% to 0.04%, 0.05% to 0.015%, etc.).

In one aspect, the microbial cultures are used without further processing in the applications that follow (i.e., with whole, growing/reproducing cells). In an alternative aspect, the cells are filtered out using a filter membrane such as, for example, filter with a 1-2 μm size cutoff. Further in this aspect, the filtrate is preserved and used as the microbial extract in the applications that follow. In still another aspect, the filtrate can be partially or fully dried to produce a solid or powder (such as, for example, by lyophilization) prior to use. Further in this aspect, the filtrate can be resuspended in water until it dissolves, with stirring and heating if necessary, or can be partially resuspended into a suspension or a slurry. In still another aspect, cells can be lysed as described previously and the composition including lysed cells can be used as the microbial extract in the applications that follow, either as-is or dried. In some aspects, the dried composition containing lysed cells can be reconstituted as a solution or slurry as described above for the filtrate. In still other aspects, the composition containing lysed cells can be further purified by filtration or another method prior to use as an extract, and can be used as-is or dried and reconstituted as described above.

In one aspect, a dried filtrate, lysed cell culture, or whole cell culture can be reconstituted in water as a solution, suspension, or slurry and used in further applications. In another aspect, the filtrate, lysed cell culture, or whole cell culture can be used as-is, without further processing. In still another aspect, any of the solutions, suspensions, or slurries described above can be mixed together, with or without water or another solvent, and used in the applications that follow.

Genelight Extracts as Power Sources

In one aspect, described herein are circuits containing the genelight extracts and compositions described herein. In another aspect, the circuits incorporate the extracts and compositions as electrolyte solutions, i.e., as in a battery. In a further aspect, the circuits include metal electrodes immersed in the extracts and compositions and wired to one another to provide for transfer of electric charge. In one aspect, the electrodes are made from zinc, cadmium, copper, silver, graphite, rhodium, or lead. In one aspect, the electrodes are copper and zinc. In a further aspect, the circuits are arranged as series or as parallel circuits.

In another aspect, described herein is a battery containing the extracts and compositions described herein. In one aspect, the battery uses the extracts and compositions as electrolytes and incorporates a circuit of the type previously described. In another aspect, the battery can be used to power a device or part of a device such as those described herein. In one aspect, the battery is sufficient power for the device and no external power supply is needed. In an alternative aspect, the battery acts as a supplement to another power source.

In a further aspect, the battery and/or circuit described herein use only environmentally safe, natural materials from the extracts and compositions as electrolytes and can be disposed of and/or recycled by the consumer. In a still further aspect, the battery or circuit does not contain toxic chemicals or heavy metals. In another aspect, the battery or circuit does not present a fire hazard. In yet another aspect, at the end of its useful life, the battery or circuit can be disassembled and the electrolyte removed and used for another application described herein (e.g., enhancing the growth of plants or microorganisms).

In one aspect, the equations in Table 7 below can be useful in modeling, describing, and/or predicting the behavior of microbial circuits and electronic devices using those circuits constructed using the extracts and compositions described herein:

TABLE 7

Equations Useful for Circuits Incorporating Microbial Extracts

| Property | Formula | Variable Descriptions | Units |
| --- | --- | --- | --- |
| Biological Charge | BQ = OIDC × {CR × pH × [C](IC$_e$ − IC$_c$)EZ} | CR: culture redox<br>pH: culture pH<br>[C]: cell concentration (cells/mL)<br>EZ: extract size<br>IC: iron concentration<br>OIDC: organic-inorganic dilution coefficient | mv × mg mL |

TABLE 7-continued

Equations Useful for Circuits Incorporating Microbial Extracts

| Property | Formula | Variable Descriptions | Units |
| --- | --- | --- | --- |
| Electric Power | $P = V \times I$ | V: electric potential<br>I: electric current | watts (W) |
| Genelight Electric Power[a] | $W_{BL} = OIDC \times V \times I$ | V: electric potential<br>I: electric current<br>OIDC: organic-inorganic dilution coefficient | watts (W) |
| Microbial Electric Current | $I = OIDC \times P/V$ | V: electric potential<br>P: microbial electric power<br>OIDC: organic-inorganic dilution coefficient | amperes (A) |
| Photon Emission Duration[a] | $PED = (P \times BQ \times \lambda)$ | P: microbial electric power<br>BQ: biological charge<br>λ: color wavelength | W × mv × mg<br>mL |

[a]Equations specific to circuits including an LED or other light-producing element.

Applications of Genelight Extracts

In one aspect, the compositions and extracts described herein are useful in a variety of applications such as, for example, powering lighting sources, powering warming and cooling devices, and powering battery operated or other electrical devices in a variety of environments and settings.

Lighting Applications

In one aspect, for any device or in any situation where lighting is required and where use of an LED is suitable, the compositions and extracts disclosed herein can be incorporated into a circuit as described previously, wherein the circuit can provide lighting for one or more of: cell phones, medical instruments, holiday lighting displays, handheld flashlights, indicator lights on radar or sonar equipment, digital displays of alphanumeric information, billboards, automobiles (both interior and exterior), airport runways, train tracks, subways, highways, street signs, traffic lights, auxiliary lighting for building safety, exit signs and other lighted signs, flares, night-vision equipment, telescopes, binoculars, rifle scopes, distance finders, and the like.

Warming and Cooling Applications

In another aspect, wherever a temperature differential is required, the compositions and extracts disclosed herein can be incorporated into a circuit as described previously, wherein the circuit can provide warming and/or cooling for one or more of: clothing including, but not limited to, gloves, hats, coats, shoes, socks, blankets, or baby clothing; climate control in buildings including, but not limited to, floor heating, roof heating, building heating, water heaters, fans, and the like; food preparation and storage including but not limited to, refrigerators, freezers, beverages coolers and warmers, food warmers, ice chests, cooking apparatuses including stoves and grills, and the like. In still another aspect, the compositions and extracts disclosed herein can be used as add-ins or backups to other power sources such as, for example, gas, coal, nuclear, solar, or wind energy, or can be used during power outages instead of or in addition to generators.

Battery-Powered and Electrical Devices

In one aspect, the compositions and methods described herein can be incorporated into a circuit as described previously, wherein the circuit can be incorporated into an electronic device such as a battery of any size including a rechargeable battery, a key fob or remote control, an electronic reading device, a laptop or portable computer, or similar. In another aspect, the circuit can be incorporated into a kitchen appliance such as, for example, a microwave, toaster, coffee maker, oven, electric knife, food and beverage slicers, grinders, mixers, and dispensers, blenders, and the like. In still another aspect, the circuit can be incorporated into a television, portable video device, radio, speaker, microphone, video game console or controller, headphones, sound canceling equipment, or similar. In still another aspect, the circuit can be incorporated into a toy, a bicycle or tricycle, a musical instrument, a prosthetic limb, pacemaker, a CPAP device, a device for stimulating muscle growth and regeneration, or an insulin pump or other powered medical implant, a thermometer, a hearing aid, eyeglasses, another medical device, a scientific instrument such as, for example, a microscope, a power tool such as an air compressor, a gas detection device, a smoke detector, or an electric toothbrush or other small personal hygiene or grooming device. In one aspect, the circuit can be used in the transportation industry, for example, in automobiles, trucks, trains, buses and other means of public transportation, subways, watercraft of various sizes, aircraft, drones, motorcycles, golf carts, and the like. In another aspect, the circuit can be used in any type of pump (i.e., water, sewage, oil field, marine, swimming pool or hot tub, artificial heart). In yet another aspect, the circuit can be incorporated into electric fencing egress and control, a clock or other timekeeping device, irrigation systems and landscaping equipment, a cash register, voting equipment, buzzers, security systems, pest control devices, and equipment for industrial or home cleaning and sterilizing.

In one aspect, the devices can be wireless devices. In an alternative aspect, the devices may optionally require wires for operation.

Environmental Suitability

Devices and applications of the compositions and extracts disclosed herein are suitable for use in a variety of environments. In one aspect, the devices can be used in applications under water, at high altitudes, at temperature extremes both high and low, in situations where traditional batteries and/or power sources would present a flammability hazard or explosion risk, in space, in laboratories and industrial facilities, in remote locations, and in areas with weather extremes including wind, rain, sandstorms, and the like.

Methods for Enhancing the Growth of Microorganisms

In one aspect, the compositions and extracts disclosed herein can be used as a culture medium for commercially important microorganisms, or can be used as a supplement to an existing medium. Further in this aspect, culturing microorganisms in the presence of the compositions and extracts disclosed herein can lead to enhanced growth rates and/or enhanced production of desirable metabolites.

In a further aspect, the compositions and extracts disclosed herein are useful in culturing the following types or organisms: (1) *Saccharomyces cerevisiae* for use in yeast doughs, brewing beer and wine, genetic research, and production of desirable secondary metabolites including the enzymes invertase and raffinase; *Kluyveromyces* species for the commercial production of lactase; and *Candida* species for the commercial production of lipase; (2) *Lactobacillus* species for use in making fermented foods such as yogurt, kefir, cheese, sauerkraut, pickles, hard cider, wine, and beer as well as for the commercial production of lactic acid and engineered *Lactobacillus* species engineered to produce protein drugs such as, for example, insulin; (3) *Pyrococcus furiosus, Thermus aquaticus, Bacillus stearothermophilus, Thermus filiformis, Thermus* thermophiles, and other thermophiles for production of heat stable polymerases for use in the polymerase chain reaction (PCR); (4) *Xanthomonas* species for production of xanthan gum, used in a variety of food and cosmetic products; (5) *Aspergillus niger*, used in the production of citric acid and fermentation of sake and other alcoholic beverages and this and other *Aspergillus* species for commercial production of α-amylase, aminoacylase, glucoamylase, catalase, glucose oxidase, lactase, pectinase, pectin lyase, and protease; *Trichoderma* species for the commercial production of cellulose; *Mucor miehei* for the commercial production of rennet; *Rhizopus* species for the commercial production of lipase; and *Mortierella* species for the commercial production of raffinase; (6) *Clostridium* species for production of botulinum toxin for cosmetic and medical purposes as well as the production of butanol (i.e., from *Clostridium acetobutylicum*); (7) *Streptomyces* species for production of antibiotics, antiparasitic, antineoplastic, and antifungal compounds including, but not limited to, chloramphenicol, daptomycin, fosfomycin, lincomycin, neomycin, nourseothricin, puromycin, streptomycin, tetracycline, oleandomycin, tunicamycin, mycangimycin, boromycin, bambermycin, clavulanic acid, guadinomine, ivermectin, migrastatin, bleomycin, erythromycin, geldanamycin, and the like; (8) *Penicillium* species for the production of penicillin and other beta-lactam antibiotics and precursors to semi-synthetic beta-lactam antibiotics; (9) *Acetobacter aceti* for production of acetic acid; (10) *Bacillus* species for commercial production of α-amylase, β-amylase, glucose isomerase, penicillin amidase, and protease; *E. coli* for commercial production of asparaginase; and *Klebsiella* species for commercial production of pullulanase; (11) *Trichoderma polysporum* for the production of cyclosporine A, (12) yeasts such as *Monascus purpureus* for the production of statin drugs for lowering blood cholesterol; (13) *Bacillus thuringiensis* for the production of insecticides, and other commercially important bacteria, fungi, algae, and cyanobateria.

In an alternative aspect, the compositions and extracts disclosed herein can be used as an animal food or animal supplement. Further in this aspect, the compositions and extracts disclosed herein may contain vitamins, minerals, proteins, peptides, carbohydrates, and/or other nutrients essential for animal growth and development and/or maintenance of animal health.

Methods for Enhancing the Physiological Properties of Plants

The compositions and extracts described herein can enhance or improve the physiological properties of a plant. The term "physiological property" as defined herein includes any physical, chemical, or biological feature that is improved using the compositions and extracts described herein. In one aspect, the compositions and extracts can enhance the growth rate of the plant. In another aspect, the physiological property includes increased root tension, root length, hormone production, drought tolerance, disease resistance, photosynthesis, or any combination thereof.

Herein, "plant" is used in a broad sense to include, for example, any species of woody, ornamental, crop, cereal, fruit, or vegetable plant, as well as photosynthetic green algae. "Plant" also refers to a plurality of plant cells that are differentiated into a structure that is present at any stage of the plant's development. Such structures include, but are not limited to, fruits, shoots, stems, leaves, flower petals, roots, tubers, corms, bulbs, seeds, gametes, cotyledons, hypocotyls, radicles, embryos, gametophytes, tumors, and the like. "Plant cell," "plant cells," or "plant tissue" as used herein refer to differentiated and undifferentiated tissues of plants including those present in any of the tissues described above, as well as to cells in culture such as, for example, single cells, protoplasts, embryos, calluses, etc.

The selection of the plant used in the methods described herein can vary depending on the application. For example, a specific plant can be selected that produces certain desirable metabolites. Current techniques for producing most plant metabolites are expensive. For example, large amounts of fresh plant biomass must be cultivated and harvested and expensive and time-consuming extraction methods must be used. The compositions and extracts described herein enhance the production of metabolites from plants that naturally produce these metabolites.

In one aspect, plant cells when contacted with the compositions and extracts described herein exhibit enhanced production of various desirable metabolites. Recipient cell targets include, but are not limited to, meristem cells, Type I, Type II, and Type III callus, immature embryos and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescences, seedling apical meristems, microspores, and the like. Those cells that are capable of proliferating as callus are also useful herein. Methods for growing plant cells are known in the art. In one aspect, plant calluses grown from 2 to 4 weeks can be used herein. The plant cells can also be derived from plants varying in age. For example, plants that are 80 days to 120 days old after pollination can be used to produce calluses useful herein.

The plant cells can be contacted with the compositions and extracts described herein in a number of different ways. In one aspect, the compositions and extracts described herein can be added to media containing the plant cells, or can be the media containing the plant cells. In another aspect, the compositions and extracts can be injected into the plant cells via syringe. The amount of extract and the duration of exposure to the extract can vary as well.

Once the plant cells have been in contact with the compositions and extracts for a sufficient time to produce a desired metabolite, the metabolite is isolated. In one aspect, the metabolite is extracted from the media containing the plant cells. The selection of extraction solvent can vary depending on the solubility of the metabolite.

In other aspects, the compositions and extracts described herein can increase the growth rate of a plant. In particular, the compositions and extracts described herein are effective in accelerating plant development in the early stages of tissue culturing. By accelerating plant development in the early stages, it is possible to harvest more metabolites from the plant. Additionally, traditional methods for tissue culture involve the use of synthetic growth factors such as 2,4-dichlorophenoxyacetic acid (2,4-D), which can pose environmental concerns. The compounds and extracts described herein avoid the need for such compounds.

In certain aspects, any of the compositions and extracts described above can be used in combination with a polysaccharide to enhance one or more physiological properties of the plant. In one aspect, the plant (e.g., cells, seeds, callus, mature plant) is first contacted with the compositions and extracts described herein, then subsequently contacted with the polysaccharide. In another aspect, the plant is first contacted with the polysaccharide, then subsequently contacted with the compositions or extracts described herein. In a still further aspect, the plant cells are contacted simultaneously with the polysaccharide and the compositions and extracts described herein.

Inn one aspect, the polysaccharide includes a polyactive carbohydrate as described and produced in WO 2019/055456, which is incorporated by reference in its entirety with respect to polyactive carbohydrates. In another aspect, the polysaccharide is a polyactive carbohydrate produced by a biological device transformed with a DNA construct as depicted in FIGS. 1A-1 and 2A-2B in WO 2019/055456. In another aspect, the polysaccharide is a polyactive carbohydrate produced by a biological device transformed with a DNA construct having SEQ ID NO. 5 or at least 90% homology thereof or SEQ ID NO. 7 or at least 90% homology thereof as provided in WO 2019/055456.

In one aspect, the polysaccharide includes chitosan, glucosamine (GlcN), N-acetylglucosamine (NAG), or any combination thereof. Chitosan is generally composed of GlcN and NAG units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, chitosan isolated from shells of crab, shrimp, lobster, and/or krill is useful herein.

In one aspect, the polysaccharide is in a solution of water and acetic acid at less than 1% by weight, less than 0.75% by weight, less than 0.5% by weight, less than 0.25% by weight, or less than 0.1% by weight. In another aspect, the amount of chitosan that is applied to the plant cells is from 0.01 wt % to 0.1 wt % by weight, or 0.01 wt %, 0.02 wt %, 0.03 wt %, 0.04 wt %, 0.05 wt %, 0.06 wt %, 0.07 wt %, 0.08 wt %, 0.09 wt %, or 0.1 wt %, where any value can be an upper or lower endpoint of a range (e.g., 0.01 wt % to 0.09 wt %, 0.02 wt % to 0.08 wt %, etc.). The polysaccharides used herein are generally natural polymers and thus present no environmental concerns. Additionally, the polysaccharides can be used in acceptably low concentrations. In certain aspects, however, the polysaccharides can be used in combination with one or more plant growth regulators.

In one aspect, the polysaccharide is in a solution of water and acetic acid at less than 1% by weight, less than 0.75% by weight, less than 0.5% by weight, less than 0.25% by weight, or less than 0.1% by weight. In another aspect, the amount of chitosan that is applied to the plant cells is from 0.01 wt % to 0.1 wt % by weight, or 0.01 wt %, 0.02 wt %, 0.03 wt %, 0.04 wt %, 0.05 wt %, 0.06 wt %, 0.07 wt %, 0.08 wt %, 0.09 wt %, or 0.1 wt %, where any value can be an upper or lower endpoint of a range (e.g., 0.01 wt % to 0.09 wt %, 0.02 wt % to 0.08 wt %, etc.). The polysaccharides used herein are generally natural polymers and thus present no environmental concerns. Additionally, the polysaccharides can be used in acceptably low concentrations. In certain aspects, however, the polysaccharides can be used in combination with one or more plant growth regulators.

In one aspect, disclosed herein are compositions composed of the genelight extracts described herein with one or more polysaccharides. In one aspect, the composition includes water. In one aspect, the composition includes the genelight extract, chitosan, polyactive carbohydrate, and water. In one aspect, the genelight extract is less than 1% by weight, less than 0.75% by weight, less than 0.5% by weight, less than 0.25% by weight, less than 0.1% by weight, less than 0.5% by weight, or less than 0.3% by weight of the composition. In one aspect, the polysaccharide is chitosan and is less than 1% by weight, less than 0.75% by weight, less than 0.5% by weight, less than 0.25% by weight, less than 0.1% by weight, less than 0.5% by weight, or less than 0.3% by weight of the composition. In one aspect, the polysaccharide is a polyactive carbohydrate and is less than 1% by weight, less than 0.75% by weight, less than 0.5% by weight, less than 0.25% by weight, less than 0.1% by weight, less than 0.5% by weight, or less than 0.3% by weight of the composition.

In one aspect, the plant growth regulator is an auxin, a cytokinin, a gibberellin, abscisic acid, or a polyamine. In a further aspect, the auxin is a natural or synthetic auxin. In a still further aspect, the auxin is indole-3-acetic acid (IAA), 4-chloroindole-3-acetic acid (4-Cl-IAA), 2-phenylacetic acid (PAA), indole-3-butyric acid (IBA), 2,3-dichlorophenoxyacetic acid (2,4-D), α-naphthalene acetic acid (α-NAA), 2-methoxy-3,6-dichlorobenzoic acid (dicamba), 4-amino-3,5,6-trichloropicolinic acid (torden or picloram), 2,4,5-trichloropicolinic acid (2,4,5-T), or a combination thereof. In another aspect, the cytokinin is zeatin, kinetin, 6-benzylaminopurine, diphenylurea, thidizuron (TDZ), 6-(γ, γ-dimethylallylamino)purine, or a combination thereof. In another aspect, the gibberellin is gibberellin A1 (GA1), gibberellic acid (GA3), ent-gibberellane, ent-kaurene, or a combination thereof. In yet another aspect, the polyamine is putrescine, spermidine, or a combination thereof.

In one aspect, the plant cell or callus is first contacted with a polysaccharide and subsequently contacted with a plant growth regulator. In another aspect, the plant cell or callus is first contacted with a plant growth regulator and subsequently contacted with a polysaccharide. In an alternative aspect, the plant cell or callus is simultaneously contacted with a polysaccharide and a plant growth regulator. In a further aspect, the plant cell or callus is only contacted with a polysaccharide and is not contacted with a plant growth regulator.

The plant cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a plant callus by techniques such as, for example, coating the callus or injecting the polysaccharide into the callus. In this aspect, the age of callus can vary depending on the type of plant. The amount of polysaccharide can vary depending upon, among other things, the selection and number of plant cells. The use of the polysaccharide in the methods described herein permits rapid tissue culturing at room temperature. Due to the ability of the polysaccharide to prevent microbial contamination, the tissue can grow for extended periods of time ranging from days to several weeks. Moreover, tissue culturing with the polysaccharide can occur in the dark and/or light. As discussed above, the plant cells are also contacted with any of the compositions or extracts described above. Thus, the use of the polysaccharides and compositions and extracts described herein is a versatile way to culture and grow plant cells—and, ultimately, plants of interest—with enhanced physiological properties.

In other aspects, the plant cells can be cultured in a liquid medium on a larger scale in a bioreactor. For example, plant cells can be cultured in agar and medium, then subsequently contacted with the compositions and extracts described herein. After a sufficient culturing time (e.g., two to four weeks), the plant cells are introduced into a container with the same medium used above and, additionally, the polysaccharide. In certain aspects, the polysaccharide can be introduced with anionic polysaccharides including, but not limited to, alginates (e.g., sodium alginate, calcium alginate, potassium alginate, etc.). After the introduction of the polysaccharide, if using, the solution is mixed for a sufficient time to produce a desired result (e.g., production of a desired metabolite). Alternatively, the initial liquid medium in the bioreactor can include any of the compositions and/or extracts described herein.

In one aspect, provided herein is a plant grown by the process that involves contacting plant gamete cells or a plant reproductive organ with the extracts disclosed herein. In a further aspect, the plant is produced by the following method:

(a) contacting a plant callus with the extracts;
(b) culturing the plant callus; and
(c) growing the plant from the plant callus.

In a further aspect, the same method can be applied to other plant parts including fruits, stems, roots, tubers, corms, bulbs, flowers, buds, seeds, and the like. In a still further aspect, the same method can be applied to an entire plant.

In one aspect, the plant callus is immersed in a solution of polysaccharide (e.g., chitosan), then inoculated with the compositions and/or extracts described herein. In another aspect, the plant callus can be from 2 days up to 20 days old prior to inoculation with the compositions and/or extracts described herein. The plant callus is then allowed to grow until it is of sufficient weight and size. In one aspect, the plant callus is allowed to grow (i.e., culture) for 1 to 10 weeks after inoculation. Following growth or culture of the callus for a sufficient period of time, desired metabolites can be collected according to methods known in the art; said methods are specific to the desired metabolites and make use of properties ranging from molecular size to charge to hydrophobicity or hydrophilicity to other properties useful for collection and purification of the metabolites.

Turf Applications

In one aspect, the compositions and extracts disclosed herein can be used to improve the health and appearance of grass and/or turf such as, for example, grass or turf on sports playing fields, lawns, golf courses, and the like. In one aspect, application of the compositions and extracts enhances root growth.

In a further aspect, plant hormones can promote or stimulate plant growth and development. In one aspect, application of the compounds or extracts disclosed herein stimulates endogenous production of plant hormones, in turn enhancing root growth. In a further aspect, application of the compounds or extracts increases the production of cytokinins by the plants. Cytokinins are responsible for the growth of roots and anchoring of a plant in soil. Still further in this aspect, root strength is especially important on golf courses due to foot traffic as well as contact with golf clubs. In another aspect, application of the compounds or extracts increases the production of salicylic acid by the plants. Salicylic acid promotes and/or enhances photosynthesis, transpiration, and mineral uptake. In one aspect, increased production of salicylic acid maintains an aesthetically-pleasing green appearance in, for example, turf grasses, as well as protecting the plant against pathogenic microorganisms. In still another aspect, application of the compounds or extracts increases the production of jasmonic acid by plants. Jasmonic acid protects against environmental damage, microbial pathogens, and insects, as well as protecting against early senescence of plants. Jasmonic acid is particularly important for field grasses (e.g., on golf courses) since the grasses are kept green for most of the year.

In one aspect, application of the compounds or extracts disclosed herein increases root tension (i.e., how difficult it is to pull up a plant or section of sod to which the compounds or extracts have been applied) and/or root length. In another aspect, applications of the compounds or extracts disclosed herein leads to a greener appearance of plants such as, for example, field grasses or turf grasses. In one aspect, the compositions and extracts described herein can increase the root force of sod by about 50% to about 200%, or about 50%, about 75%, about 100%, about 125%, about 150%, about 175%, or about 200% compared to sod that has not been treated with the composition or extract, where any value can be a lower and upper endpoint of a range (e.g., about 50% to about 175%, about 75% to about 125%, etc.).

In one aspect, the compositions and extracts described herein can increase the root force of a plant by about 50% to about 200%, or about 50%, about 75%, about 100%, about 125%, about 150%, about 175%, or about 200% compared to a plant that has not been treated with the composition or extract, where any value can be a lower and upper endpoint of a range (e.g., about 50% to about 175%, about 75% to about 125%, etc.).

In one aspect, the compounds and extracts disclosed herein can be applied at a volume of about 50 to about 200 mL per square meter of, for example, turf, or can be applied at about 50 mL, about 75 mL, about 100 mL, about 125 mL, about 150 mL, about 175 mL, or about 200 mL per square meter of turf, or a combination of any of the foregoing values, or a range encompassing any of the foregoing values. In one aspect, the compounds and extracts are applied to turf at a volume of about 75 mL per square meter. In an alternative aspect, the compounds and extracts are applied to turf at a concentration of about 150 mL per square meter.

In one aspect, the compositions and extracts disclosed herein are applied multiple times to the plants of interest. Further in this aspect, the compositions and extracts can be applied once per week, twice per week, or three times per week. In one aspect, the compositions and/or extracts are applied to the plants of interest twice per week.

In another aspect, the compositions and extracts disclosed herein can be applied alone or in combination with another product intended to enhance plant growth. In one aspect, the compositions and extracts disclosed herein are applied in combination with a fertilizer such as, for example, activated sewage sludge including, but not limited to, Hou-actinite, or another commercially-available fertilizer. In one aspect, the compositions and extracts disclosed herein are applied after fertilizer application, or can be applied before fertilizer application, or can be applied at the same time as fertilizer is applied to the plants of interest. In still another aspect, another compound such as, for example, chitosan, can be applied to the plants in addition to the compositions and extracts disclosed herein. In one aspect, the chitosan can be applied as a solution with a concentration of from about 0.01% to about 0.05% (w/v), or can be applied as a solution with a concentration of about 0.01, 0.02, 0.03, 0.04, or about 0.05%. In one aspect, the chitosan is applied as a solution with a concentration of about 0.02%. In another aspect, In one aspect, the chitosan can be applied at a concentration of about 50 to about 200 mL per square meter of, for example, turf, or can be applied at about 50, 75, 100, 125, 150, 175, or about 200 mL per square meter of turf, or a combination of any of the foregoing values, or a range encompassing any of the foregoing values. In one aspect, the chitosan is applied to turf at a concentration of 75 mL per square meter. In an alternative aspect, the chitosan is applied to turf at a concentration of 150 mL per square meter. In another aspect, the chitosan can be applied to the turf once per week, twice per week, or three times per week. In one aspect, the chitosan is applied twice per week. In still another aspect, the chitosan can be applied before the compounds and extracts disclosed herein, or after the compounds and extracts disclosed herein, or simultaneously with the compounds and extracts disclosed herein.

In any of the above aspects, application of the compounds and extracts disclosed herein leads to an increase in plant hormones and, in turn, improvement in properties such as earlier rooting, root anchoring or tension, root strength, root length, green coloration, nutrient availability, reduction of irrigation needs, prevention of erosion, and other desirable properties of plants. In another aspect, enhancing plant growth including magnesium uptake and production of chlorophyll a and/or chlorophyll b can be used to trap carbon dioxide from the atmosphere.

Anti-UV Applications

The genelight extracts produced herein may be applied to any material that may benefit from a reduction in exposure to UV radiation. The exact formulation of the extract plus any carriers can be adjusted based on the desired use. In one aspect, the extract is formulated with only non-toxic components if it is to be used on a human or animal or with another microorganism, such as in a fermentation process or on an agricultural product. In another aspect, the extract can be mixed with other substances to provide UV-protective properties to the overall composition. In still another aspect, if coated on the material to be protected, the extract itself can be covered with a further protective coating to project, for example, against mechanical wear and damage.

Methods of Applying Extracts to Surfaces

In the case when the extract is applied to the surface of an article, it can be applied using techniques known in the art such spraying or coating. In other aspects, the extract can be intimately mixed with a substance or material that ultimately produces the article. For example, the extract can be mixed with molten glass so that the extract is dispersed throughout the final glass product.

In one aspect, the extract is formulated or applied in such a manner as to block approximately about 50%, about 60%, about 70%, about 80%, about 90%, about 95%, or about 99% of the UV radiation that encounters the extract, where any value can be a lower and upper end-point of a range (e.g., about 60% to about 95%, about 70% to about 80%). In a further aspect, the extract can also be formulated to block these percentages of particular UV wavelengths, or, more generally, to block these percentages of UVA, UVB, or UVC radiation.

Uses of the Extracts

Extracts according to the present disclosure can be used for a variety of purposes. These purposes include, but are not limited to, the following:

1. blocking UV radiation or other types of radiation;
2. protecting human skin against damage and/or skin cancer induced by UV radiation or other types of radiation;
3. protecting against side effects of radiation used in cancer treatments;
4. protecting animals from deleterious effects of UV radiation or other radiation;
5. protecting plastic, fiberglass, glass, rubber, or other solid surfaces from UV radiation or other radiation;
6. providing a UV radiation screen or screen for other types of radiation;
7. protecting astronauts and/or other persons or organisms as well as equipment during space trips;
8. enhancement of industrial fermentation processes or other processes requiring energy by allowing the use of UV radiation in connection with the process to supply additional energy and thus to increase the ultimate energy-requiring output of the cells without substantially killing the fermenting organism;
9. protection of experimentation, fermentation, biochemical, and/or biological processes under the presence of UV radiation, for example in extraterrestrial conditions such as on the moon or Mars; and
10. protection of agricultural plants, particularly agricultural plants in which the revenue-producing part of the plant is above ground, such as fruits, vine vegetables, beans and peas, and leaf vegetables.

Agricultural Applications

In one aspect, the genelight can be applied to an agricultural plant. In one aspect, the plant can be one that produces fruit or vegetable, such as, for example, a watermelon or a tomato. Further in this aspect, the extract can be applied during at least a part of the plant's growth to increase the amounts of one or more nutrients of the fruit or vegetable, such as a vitamin, mineral, or other recommended dietary component. In one specific aspect, the amount of lycopene can be increased (which may be accompanied by a decrease in carotene or other less-valuable nutrients formed by competing pathways). In another aspect, the amount of a flavor-enhancing component, such as glucose, can be increased. Further in this aspect, an increase in glucose can help protect against water loss.

In one aspect, the genelight extract can be applied for about 25%, about 50%, about 75%, about 90%, about 95%, or about 99% of the fruit's or vegetable's on-plant life, where any value can be a lower and upper endpoint of a range (e.g., about 25% to about 95%, about 50% to about 75%, etc.), and where the on-plant life includes the time span from the formation of a separate body that will constitute the fruit or vegetable (in some aspects, excepting flowers) until the fruit or vegetable is harvested. In one aspect, the extract can be first applied when the fruit or vegetable is sufficiently large to no longer be substantially protected from UV radiation by leaves. In another aspect, the extract can first be applied five days, one week, or two weeks prior to harvest. Further in this aspect, application at this later stage can be particularly useful with fruits or vegetables in which an increase in a nutrient or flavor-enhancing component can be obtained by protecting the fruit or vegetable from UV radiation later in its on-plant life.

In one aspect, the genelight extract can be applied once or multiple times to each fruit or vegetable. In another aspect, it can be applied weekly, or it can be reapplied after the fruit or vegetable is exposed to rain or after a turning process. In another aspect, the agricultural plant can be another food crop that grows above ground and is exposed to natural UV radiation, wherein the agricultural product produced can be a fruit, leaf, seed, flower, grain, nut, stem, vegetable, or mushroom.

In another aspect, it is desirable for agricultural plants that do not produce parts typically consumed by humans to be protected from UV irradiation. In a further aspect, these other agricultural plants can includes sources of fibers such as, for example, cotton and linen (flax), of cork, of wood or lumber, of feedstocks for producing ethanol or biodiesel (including, but not limited to, sugar beet, sugarcane, cassava, sorghum, corn, wheat, oil palm, coconut, rapeseed, peanut, sunflower, soybean, and the like), of animal feedstocks or fodder, or of decorative or horticultural plants.

In one aspect, any part of the plant can be coated with the genelight extract, including, but not limited to, the part of the plant that is collected during harvest. In an alternative aspect, the harvested part of the plant is not coated, but another part can be coated with the extracts disclosed herein. In addition to the aspects already described, in one aspect, coating a plant with the extracts described herein can prolong the life of the plant, increase production capacity of a desired product, can increase the growth rate of the plant relative to an untreated plant of the same type, can increase production of a desired metabolite that might otherwise decrease due to UV-induced stress, can increase yield of a crop of such plants, and the like.

In a further aspect, application can be accomplished with a commercial sprayer. In another aspect, application can be only on the upper portions of the fruit or vegetable, which are exposed to substantially greater amounts of UV radiation than the lower portions of the fruit or vegetable.

Cosmetics and Pharmaceutical Compositions Containing the Extracts

In another aspect, provided herein is a pharmaceutical composition containing the genelight extracts described herein. In one aspect, the pharmaceutical composition can be applied to a subject, wherein the subject is exposed to radiation. In one aspect, the radiation is applied as a strategy to treat cancer. In another aspect, the pharmaceutical composition is used to prevent radiation-induced cellular and DNA damage. In another aspect, dosage ranges of the extract in the pharmaceutical composition can vary from about 0.01 g extract/mL of pharmaceutical composition to about 1 g extract/mL of pharmaceutical composition, or can be about 0.01 g extract/mL, about 0.02 g extract/mL, about 0.025 g extract/mL, about 0.05 g extract/mL, about 0.075 g extract/mL, or about 1 g extract/mL of pharmaceutical composition, where any value can be a lower and upper endpoint of a range (e.g., about 0.01 g extract/mL to about 0.075 g extract/mL, about 0.025 g extract/mL to about 0.05 g extract/mL, etc.). In an alternative aspect, provided herein is a cosmetic composition containing the genelight extracts produced herein. Further in this aspect, the cosmetic composition can be a cleanser, lotion, cream, shampoo, hair treatment, makeup, lip treatment, nail treatment, or related composition. In still a further aspect, the compositions containing the extracts can have both pharmaceutical and cosmetic applications. In yet another aspect, the compositions containing the extracts can be used in veterinary medicine.

The cosmetic compositions can be formulated in any physiologically acceptable medium typically used to formulate topical compositions. The cosmetic compositions can be in any galenic form conventionally used for a topical application such as, for example, in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/VV or O/W/O), microemulsions, vesicular dispersions of ionic and/or non-ionic type, or wax/aqueous phase dispersions. These compositions are prepared according to the usual methods.

The cosmetic compositions can also contain one or more additives commonly used in the cosmetics field, such as emulsifiers, preservatives, sequestering agents, fragrances, thickeners, oils, waxes or film-forming polymers. In one aspect, in any of the above scenarios, the pharmaceutical, cosmetic, or veterinary composition also includes additional UV-protective compounds or UV-blocking agents such as, for example, zinc oxide, titanium dioxide, carotenoids, oxybenzone, octinoxate, homosalate, octisalate, octocrylene, avobenzone, or a combination thereof.

In one aspect, the composition is a sunscreen. A sunscreen can be formulated with any of the extracts produced herein. In addition to the extract, the sunscreen in certain aspects can be formulated with one or more UV-protective compounds or UV-blocking agents listed above. The sunscreen can be formulated as a paste, lotion, cream, aerosol, or other suitable formulations for topical use. In certain aspects, the sunscreen can be formulated as a transparent composition.

In one aspect, the cosmetic composition can be a film composed of the genelight extracts produced herein that can be directly applied to the skin. For example, the film can be composed of a biocompatible material such as a protein or oligonucleotide, where the extract is coated on one or more surfaces of the film or, in the alternative dispersed throughout the film. For example, the film can be composed of DNA. In this application, the films can be used as a wound covering and provide protection from UV photodamage. The films can also be prepared so that they are optically transparent. Here, it is possible to view the wound without removing the covering and exposing the wound. The films can also include other components useful in cosmetic applications such as, for example, compounds to prevent or reduce wrinkles.

In one aspect, the pharmaceutical, cosmetic, or veterinary compositions described herein are applied to subjects. In one aspect, the subject is a human, another mammal, or a bird. In a further aspect, the mammal is a pet such as a dog or cat or is livestock such as horses, goats, cattle, sheep, and the like. In an alternative aspect, the bird is a pet bird or is poultry such as, for example, a chicken or turkey. In any of these aspects, the compositions can be applied to skin, fur, feathers, wool, hooves, horns, or hair as appropriate and applicable.

In a related aspect, the compositions and extracts disclosed herein and/or the pharmaceutical, cosmetic, or veterinary compositions disclosed herein are applied to isolated human or animal cells. Further in this aspect, the compositions and extracts and/or the pharmaceutical, cosmetic, or veterinary compositions disclosed herein can be applied to the isolated human or animal cells in any desired volume ratio such as, for example, from about 1:7 to about 7:1, or about 1:7, 2:5, 5:4, 5:2, or about 7:1. In one aspect, the compositions or extracts disclosed herein are applied to human fibroblast cells in culture at a volume ratio of about 5:4.

Further in this aspect, the compositions and extracts disclosed herein protect the isolated human or animal cells from UV-induced cell death. Still further in this aspect, this protection can be assessed by known means such as, for example, staining with trypan blue and counting living and/or dead cells under a microscope, or by assessing total amount of genomic DNA present in the sample by a means such as, for example, gel electrophoresis followed by quantification of stain intensity.

Paints, Inks, Dyes, and Stains

In another aspect, provided herein is a paint, dye, stain, or ink containing the genelight extracts disclosed herein. In one aspect, there are several benefits to having a paint that is resistant to UV irradiation. In a further aspect, imparting UV resistance to a paint slows or stops photodegradation, bleaching, or color fading. In another aspect, a paint with UV resistance prevents chemical modification of exposed paint surfaces. Further in this aspect, chemical modification of exposed paint surfaces includes change in finish, structural changes in binders, flaking, chipping, and the like. In one aspect, the paint provided herein resists these changes.

Articles Incorporating the Genelight Extracts

In still another aspect, provided herein is an article coated with the genelight extracts disclosed herein. In one aspect, the article is made of glass, plastic, metal, wood, fabric, or any combination thereof. In one aspect, the article is a construction material such as, for example, steel, concrete or cement, brick, wood, window or door glass, fiberglass, siding, wallboard, a flooring material, masonry, mortar, grout, stone, artificial stone, stucco, shingles, roofing materials, and the like. In an alternative aspect, the material is an aeronautical or aerospace material such as, for example, the metal or metal alloy body of an aircraft or spacecraft, paint on the body of an aircraft or spacecraft, glass windows on an aircraft or spacecraft, carbon fiber composite, titanium or aluminum, a ceramic heat absorbing tile, and the like. In still another aspect, the article is a fabric article such as, for example, clothing, drapes, outdoor upholstery, a tent or outdoor pavilion, a flag or banner, or the like. In another aspect, the extract can be applied to the article to fine artwork, solid pieces (e.g., vases), and historical documents in order to preserve them. In another aspect, the extract can be applied to outdoor signs such as highway billboards and advertising.

In other aspects, the genelight extract can be incorporated within or throughout the article. In one aspect, the extract can be mixed with molten glass to produce glass article that are UV resistant such as, for example, sunglasses, car windshields, window glass, and eyeglasses. In another aspect, the glass article can be a bottle for storing a beverage or food container in order to increase the shelf-life of the beverage or food. It is contemplated that the extract can be applied externally to the glass articles as well.

In another aspect, the genelight extract can be mixed with fiberglass or plastics in order to reduce negative effects to aircraft, watercraft, boats, jet skis, decking, house siding, motor homes, sunroofs, and moon roofs that are constantly exposed to UV radiation. It is contemplated that the extract can be applied externally to the fiberglass or plastic articles as well.

In another aspect, the genelight extract can be mixed with rubber, silicon, or latex used to make a variety of articles such as water hoses, tires, and the like. It is contemplated that the extract can be applied externally to the rubber, silicone, or latex articles as well.

In another aspect, the genelight extract can be mixed with foams used to make a variety of articles such as automotive dashboard padding, seat cushions, and the like. It is contemplated that the extract can be applied externally to the foam articles as well.

In another aspect, the genelight extracts described herein can be incorporated into an optical film. In one aspect, the extract is applied to at least one surface of the film. In another aspect, the extract can be dispersed throughout the film. The film can be transparent, translucent or opaque. The film can be composed of, but not limited to, polyolefin resin, such as polyethylene (PE) or polypropylene (PP); polyester resin, such as polyethylene terephthalate (PET); polyacrylate resin, such as polymethyl (meth)acrylate (PMMA); polycarbonate resin; polyurethane resin or a mixture thereof. The optical film can be applied to any substrate where it is desirable to reduce or prevent UV exposure or damage. For example, the optical film can be applied to windows to reduce or prevent UV radiation from entering a structure (e.g., building, vehicle, etc.).

Methods for Reducing or Preventing Exposure to UV Radiation

In another aspect, provided herein is a method of reducing or preventing the exposure of an item to UV radiation by applying the genelight extracts described herein to the item or incorporating the extract within/throughout the article. Further in this aspect, "reducing" is defined relative to an untreated control. That is, if two like items are exposed to equal amounts of UV radiation for an equal amount of time, but one has been treated with the UV-resistant extracts and the other has not, and some objective response is measured (e.g., color fading, structural degradation, plant size or yield, etc.), the treated item will appear to have been exposed to a lower amount of UV (for example, the color of the treated item will have faded less and will remain closer to the original, or a treated plant will appear larger and more vigorous and will have a greater yield, etc.). In some aspects, treatment with the extracts disclosed herein will prevent UV exposure from occurring. As used herein, "prevent" indicates that a treated item will not be affected, changed, or altered by UV exposure.

In one aspect, the genelight extract blocks from about 50% to about 100% of UV radiation from contacting the item. Further in this aspect, the extract blocks about 50%, about 55%, about 60%, about 65%, about 70%, about 75%, about 80%, about 85%, about 90%, about 95%, about 99%, or about 100% of UV radiation from contacting the item, where any value can be a lower and upper endpoint of a range (e.g., about 50% to about 90%, about 60% to about 80%, etc.). In another aspect, the extract blocks from about 50% to about 100% of longwave UV radiation from contacting the item. Further in this aspect, the extract blocks about 50%, about 55%, about 60%, about 65%, about 70%, about 75%, about 80%, about 85%, about 90%, about 95%, about 99%, or about 100% of longwave UV radiation from contacting the item, where any value can be a lower and upper endpoint of a range (e.g., about 50% to about 90%, about 60% to about 80%, etc.). In one aspect, the extract blocks from about 50% to 100% of shortwave UV radiation from contacting the item. Further in this aspect, the extract blocks about 50%, about 55%, about 60%, about 65%, about 70%, about 75%, about 80%, about 85%, about 90%, about 95%, about 99%, or about 100% of shortwave UV radiation from contacting the item, where any value can be a lower and upper endpoint of a range (e.g., about 50% to about 90%, about 60% to about 80%, etc.).

Depending upon the application, the genelight extract can prevent or reduce damage cause by UV radiation from limited to extended periods of time. By varying the amount of extract that is applied as well as the number of times the extract is applied, the degree of UV protection can be varied. In certain aspects, it may be desirable for the article to be protected from UV damage for a short period of time then subsequently biodegrade.

Preventing or Reducing the Growth of Barnacles

In another aspect, the genelight extracts produced herein can be used to reduce or prevent the growth of barnacles on boats and other water vehicles. In one aspect, the extract can be admixed with a paint that is typically applied to water vehicles, where the paint also includes chitosan. In one aspect, the chitosan can be acetylated to a specific degree of acetylation in order to enhance tissue growth during culturing as well as metabolite production. In one aspect, the chitosan is from about 60% to about 100%, or about 60%, about 65%, about 70%, about 75%, about 80%, about 85%, about 90%, about 95%, about 99%, or about 100%, where any value can be a lower and upper endpoint of a range (e.g., about 60% to about 90%, about 70% to about 80%, etc.). In one aspect, chitosan isolated from the shells of crab, shrimp, lobster, and/or krill is useful herein. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units, where any value can be a lower and upper endpoint of a range (e.g., 3 to about 19, 5 to 7, etc.).

Protection of Microbial Cultures from the Effects of UV Radiation

In one aspect, the compositions and extracts disclosed herein can be applied to cultures of commercially-important microorganisms. Further in this aspect, the compositions and extracts disclosed herein offer protection from UV radiation to the microorganisms. In one aspect, the microorganisms are used for the production of industrially-important enzymes or chemical compounds such as, for example, *Acetobacter aceti* (source of acetic acid), *Aspergillus niger* (source of citrus acid), any microorganism that produces enzymes such as, for example, cellulases, amylase, palatase, lipozyme, lipase, lipopan F, xylose isomerase, resinase, penicillin amidase, or amidase. In another aspect, the microorganisms are important for fermentation in food production, including, but not limited to, *Saccharomyces cerevisiae* for the production of bread and for alcoholic fermentation, bacteria such as *Streptococcus* thermophiles, *Lactobacillus delbrueckii*, and other lactobacilli and bifidobacteria important in the production of yogurt, skyr, kefir, and other fermented dairy products, *Lactococcus* species and *Propionibacter shermani* used in the production of some cheeses, *Clostridium butyricum* useful in the process of retting of jute, hemp, and/or flax, microorganisms used for water treatment and/or sewage treatment, experimental microorganisms useful in molecular biology, genetic engineering, and other laboratory uses including, but not limited to, *E. coli, B. subtilis*, and the like, microooragnisms useful in the production of B vitamins and other vitamins, microorganisms such as *Bacillus thuringiensis* useful for agricultural pest control, and the like.

In one aspect, the cultures and extracts disclosed herein can be mixed in any proportion with cultures of commercially important microorganisms for the purpose of providing protection from UV-irradiation to the commercially important microorganisms. In one aspect, the cultures and extracts can be applied in a volume ratio of from 1:7 to 7:1 to cultures of the commercially important microorganisms, or can be applied in a ratio of about 1:7, 2:5, 3:4, 4:3, 5:2, 7:1, or a combination of any of the foregoing values, or a range encompassing any of the foregoing values. In a further aspect, the cultures and extracts are applied in a ratio of 5:2 to cultures of commercially important microorganisms.

In another aspect, treatment with the cultures and extracts disclosed herein protects the commercially important microorganisms from negative effects of UV radiation for a period of from 10 minutes to 2 hours, or for about 10 minutes, 15 minutes, 20 minutes, 30 minutes, 1 hour, 90 minutes, or about 2 hours, or a combination of any of the foregoing values or a range encompassing any of the foregoing values.

In one aspect, successful protection from negative effects of UV radiation can be assessed by culturing cells of the commercially important microorganism in a Petri dish and counting colonies, or by any other common means for assessing cell survival, with higher numbers of surviving cells being indicative of successful UV protection. In any of the above aspects, the cultures and extracts disclosed herein are biocompatible and do not harm the commercially important microorganisms.

ASPECTS

The present disclosure can be described in accordance with the following numbered Aspects, which should not be confused with the claims.

Aspect 1. A DNA construct comprising the following genetic components: (a) a gene that expresses a heat shock protein, (b) a gene that expresses RuBisCO large subunit 1, (c) a gene that expresses tonB, (d) a gene that expresses hydrogenase, and (e) a gene that expresses p-type ATPase.

Aspect 2. The DNA construct of aspect 1, wherein the gene that expresses a heat shock protein expresses HSP70.

Aspect 3. The DNA construct of aspect 2, wherein the gene that expresses HSP70 has SEQ ID NO. 1 or at least 70% homology thereto.

Aspect 4. The DNA construct of any preceding aspect, wherein the gene that expresses RuBisCO large subunit 1 has SEQ ID NO. 2 or at least 70% homology thereto.

Aspect 5. The DNA construct of any preceding aspect, wherein the gene that expresses tonB has SEQ ID NO. 3 or at least 70% homology thereto.

Aspect 6. The DNA construct of any preceding aspect, wherein the gene that expresses hydrogenase has SEQ ID NO. 4 or at least 70% homology thereto.

Aspect 7. The DNA construct of any preceding aspect, wherein the gene that expresses p-type ATPase has SEQ ID NO. 5 or at least 70% homology thereto.

Aspect 8. The DNA construct in any preceding aspect, wherein the DNA construct further comprises a promoter.

Aspect 9. The DNA construct of aspect 8, wherein the promoter comprises a GAL1 promoter, an araBAD promoter, or both.

Aspect 10. The DNA construct in any preceding aspect, wherein the DNA construct further comprises a terminator.

Aspect 11. The DNA construct of aspect 10, wherein the terminator comprises a CYC1 terminator, an rrnB terminator, or a combination thereof.

Aspect 12. The DNA construct of aspect 9, wherein a GAL1 promoter is positioned before (a) the gene that expresses a heat shock protein, (b) the gene that expresses RuBisCO large subunit 1, (c) the gene that expresses tonB, (d) the gene that expresses hydrogenase, (e) the gene that expresses p-type ATPase, or any combination thereof.

Aspect 13. The DNA construct of aspect 11, wherein a CYC1 terminator is positioned after (a) the gene that expresses a heat shock protein, (b) the gene that expresses RuBisCO large subunit 1, (c) the gene that expresses tonB, (d) the gene that expresses hydrogenase, (e) the gene that expresses p-type ATPase, or any combination thereof.

Aspect 14. The DNA construct of aspect 9, wherein an araBAD promoter is positioned before (a) the gene that expresses a heat shock protein, (b) the gene that expresses RuBisCO large subunit 1, (c) the gene that expresses tonB, (d) the gene that expresses hydrogenase, (e) the gene that expresses p-type ATPase, or any combination thereof.

Aspect 15. The DNA construct of aspect 11, wherein an rrnB terminator is positioned after (a) the gene that expresses a heat shock protein, (b) the gene that expresses RuBisCO large subunit 1, (c) the gene that expresses tonB, (d) the gene that expresses hydrogenase, (e) the gene that expresses p-type ATPase, or any combination thereof.

Aspect 16. The DNA construct of any preceding aspect, wherein the DNA construct further comprises a gene that confers resistance to an antibiotic.

Aspect 17. The DNA construct of aspect 16, wherein the antibiotic comprises tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolones, rifampin, rifampicin, sulfonamides, cephalothin, erythromycin, gentamicin, penicillin, or a combination thereof.

Aspect 18. The DNA construct in any preceding aspect, wherein the construct further comprises a gene that expresses a reporter protein.

Aspect 19. The DNA construct of aspect 18, wherein the reporter protein is a fluorescent protein.

Aspect 20. The DNA construct of aspect 19, wherein the reporter protein comprises a red fluorescent protein, a cyan fluorescent protein, a green fluorescent protein, a yellow fluorescent protein, or a combination thereof.

Aspect 21. The DNA construct of aspect 20, wherein the reporter protein is a green fluorescent protein.

Aspect 22. The DNA construct of aspect 21, wherein the green fluorescent protein is EGFP.

Aspect 23. The DNA construct of aspect 18, wherein the gene that expresses a reporter protein has SEQ ID NO. 6 or at least 70% homology thereto.

Aspect 24. The DNA construct of aspect 1, wherein the DNA construct comprises from 5' to 3' the following genetic components in the following order: (1) a gene that expresses a heat shock protein, (2) a gene that expresses RuBisCO large subunit 1, (3) a gene that expresses tonB, (4) a gene that expresses hydrogenase, and (5) a gene that expresses p-type ATPase.

Aspect 25. The DNA construct of aspect 1, wherein the DNA construct comprises from 5' to 3' the following genetic components in the following order: (1) a gene that expresses a heat shock protein having SEQ ID NO. 1 or at least 70% homology thereto, (2) a gene that expresses RuBisCO large subunit 1 having SEQ ID NO. 2 or at least 70% homology thereto, (3) a gene that expresses tonB having SEQ ID NO. 3 or at least 70% homology thereto, (4) a gene that expresses hydrogenase having SEQ ID NO. 4 or at least 70% homology thereto, and (5) a gene that expresses p-type ATPase having SEQ ID NO. 5 or at least 70% homology thereto.

Aspect 26. The DNA construct of aspect 1, wherein the DNA construct comprises from 5' to 3' the following genetic components in the following order: (1) a gene that expresses a heat shock protein having SEQ ID NO. 1 or at least 70% homology thereto, (2) a gene that expresses RuBisCO large subunit 1 having SEQ ID NO. 2 or at least 70% homology thereto, (3) a gene that expresses tonB having SEQ ID NO. 3 or at least 70% homology thereto, (4) an rrnB terminator, (5) an araBAD promoter, (6) a gene that expresses hydrogenase having SEQ ID NO. 4 or at least 70% homology thereto, and (7) a gene that expresses p-type ATPase having SEQ ID NO. 5 or at least 70% homology thereto.

Aspect 27. The DNA construct of aspect 1, wherein the DNA construct has SEQ ID NO. 7 or at least 70% homology thereto.

Aspect 28. The DNA construct of aspect 1, wherein the DNA construct comprises from 5' to 3' the following genetic components in the following order: (1) a gene that expresses hydrogenase, (2) a gene that expresses p-type ATPase, (3) a gene that expresses tonB, (4) a gene that expresses a heat shock protein, and (5) a gene that expresses RuBisCO large subunit 1.

Aspect 29. The DNA construct of aspect 1, wherein the DNA construct comprises from 5' to 3' the following genetic components in the following order: (1) a gene that expresses hydrogenase having SEQ ID NO. 4 or at least 70% homology thereto, (2) a gene that expresses p-type ATPase having SEQ ID NO. 5 or at least 70% homology thereto, (3) a gene that expresses tonB having SEQ ID NO. 3 or at least 70% homology thereto, (4) a gene that expresses a heat shock protein having SEQ ID NO. 1 or at least 70% homology thereto, and (5) a gene that expresses RuBisCO large subunit 1 having SEQ ID NO. 2 or at least 70% homology thereto.

Aspect 30. The DNA construct of aspect 1, wherein the DNA construct comprises from 5' to 3' the following genetic components in the following order: (1) a gene that expresses hydrogenase having SEQ ID NO. 4 or at least 70% homology thereto, (2) a CYC1 terminator, (3) a GAL1 promoter, (4) a gene that expresses p-type ATPase having SEQ ID NO. 5 or at least 70% homology thereto, (5) a CYC1 terminator, (6) a GAL1 promoter, (7) a gene that expresses tonB having SEQ ID NO. 3 or at least 70% homology thereto, (8) a CYC1 terminator, (8) a GAL1 promoter, (9) a gene that expresses a heat shock protein having SEQ ID NO. 1 or at least 70% homology thereto, (10) a CYC1 terminator, (11) a GAL1 promoter, (12) a gene that expresses RuBisCO large subunit 1 having SEQ ID NO. 2 or at least 70% homology thereto, and (13) a CYC1 terminator.

Aspect 31. The DNA construct of aspect 1, wherein the DNA construct has SEQ ID NO. 8 or at least 70% homology thereto.

Aspect 32. The DNA construct in any one of aspects 1-31, wherein the construct further comprises a gene that expresses a dehydrogenase.

Aspect 33. The DNA construct of aspect 32, wherein the DNA construct comprises from 5' to 3' the following genetic components in the following order: (1) a gene that expresses a heat shock protein, (2) a gene that expresses dehydrogenase, (3) a gene that expresses RuBisCO large subunit 1, (4) a gene that expresses tonB, (5) a gene that expresses hydrogenase, and (6) a gene that expresses p-type ATPase.

Aspect 34. The DNA construct of aspect 32, wherein the DNA construct comprises from 5' to 3' the following genetic components in the following order: (1) a gene that expresses a heat shock protein having SEQ ID NO. 1 or at least 70% homology thereto, (2) a gene that expresses dehydrogenase having SEQ ID NO. 9 or at least 70% homology thereto, (3) a gene that expresses RuBisCO large subunit 1 having SEQ ID NO. 2 or at least 70% homology thereto, (4) a gene that expresses tonB having SEQ ID NO. 3 or at least 70% homology thereto, (5) a gene that expresses hydrogenase having SEQ ID NO. 4 or at least 70% homology thereto, and (6) a gene that expresses p-type ATPase having SEQ ID NO. 5 or at least 70% homology thereto.

Aspect 35. The DNA construct of aspect 32, wherein the DNA construct comprises from 5' to 3' the following genetic components in the following order: (1) a gene that expresses a heat shock protein having SEQ ID NO. 1 or at least 70% homology thereto, (2) a gene that expresses dehydrogenase having SEQ ID NO. 9 or at least 70% homology thereto, (3) a gene that expresses RuBisCO large subunit 1 having SEQ ID NO. 2 or at least 70% homology thereto, (4) a gene that expresses tonB having SEQ ID NO. 3 or at least 70% homology thereto, (5) an rrnB terminator, (6) an araBAD promoter, (7) a gene that expresses hydrogenase having SEQ ID NO. 4 or at least 70% homology thereto, and (8) a gene that expresses p-type ATPase having SEQ ID NO. 5 or at least 70% homology thereto.

Aspect 36. The DNA construct of aspect 32, wherein the DNA construct has SEQ ID NO. 11 or at least 70% homology thereto.

Aspect 37. The DNA construct of aspect 32, wherein the DNA construct comprises from 5' to 3' the following genetic components in the following order: (1) a gene that expresses hydrogenase, (2) a gene that expresses p-type ATPase, (3) a gene that expresses tonB, (4) a gene that expresses a heat shock protein, (5) a gene that expresses dehydrogenase, and (6) a gene that expresses RuBisCO large subunit 1.

Aspect 38. The DNA construct of aspect 32, wherein the DNA construct comprises from 5' to 3' the following genetic components in the following order: (1) a gene that expresses hydrogenase having SEQ ID NO. 4 or at least 70% homology thereto, (2) a gene that expresses p-type ATPase having SEQ ID NO. 5 or at least 70% homology thereto, (3) a gene that expresses tonB having SEQ ID NO. 3 or at least 70% homology thereto, (4) a gene that expresses a heat shock protein having SEQ ID NO. 1 or at least 70% homology thereto, (5) a gene that expresses dehydrogenase having SEQ ID NO. 9 or at least 70% homology thereto, and (6) a gene that expresses RuBisCO large subunit 1 having SEQ ID NO. 2 or at least 70% homology thereto.

Aspect 39. The DNA construct of aspect 32, wherein the DNA construct comprises from 5' to 3' the following genetic components in the following order: (1) a gene that expresses hydrogenase having SEQ ID NO. 4 or at least 70% homology thereto, (2) a CYC1 terminator, (3) a GAL1 promoter, (4) a gene that expresses p-type ATPase having SEQ ID NO. 5 or at least 70% homology thereto, (5) a CYC1 terminator, (6) a GAL1 promoter, (7) a gene that expresses tonB having SEQ ID NO. 3 or at least 70% homology thereto, (8) a CYC1 terminator, (8) a GAL1 promoter, (9) a gene that expresses a heat shock protein having SEQ ID NO. 1 or at least 70% homology thereto, (10) a CYC1 terminator, (11) a GAL1 promoter, (12) a gene that expresses dehydrogenase having SEQ ID NO. 9 or at least 70% homology thereto, (13) a CYC1 terminator, (14) a GAL1 promoter, and (15) a gene that expresses RuBisCO large subunit 1 having SEQ ID NO. 2 or at least 70% homology thereto, and (13) a CYC1 terminator.

Aspect 40. The DNA construct of aspect 1, wherein the DNA construct has SEQ ID NO. 10 or at least 70% homology thereto.

Aspect 41. A vector comprising the DNA construct in any preceding aspect.

Aspect 42. The vector of aspect 41, wherein the vector is a plasmid.

Aspect 43. The vector of aspect 42, wherein the plasmid is pWLNEO, pSV2CAT, pOG44, pXTI, pSG, pSVK3, pBSK, pBR322, pYES, pYES2, pBSKII, pUC, or pBAD.

Aspect 44. The vector of aspect 43, wherein the plasmid is pBAD.

Aspect 45. The vector of aspect 43, wherein the plasmid is pYES2.

Aspect 46. A biological device comprising host cells transformed with the DNA construct or vector of any preceding aspect.

Aspect 47. The biological device of aspect 46, wherein the host cells comprise yeast or bacteria.

Aspect 48. The biological device of aspect 47, wherein the bacteria comprise *Escherichia coli*.

Aspect 49. The biological device of aspect 47, wherein the yeast comprise *Saccharomyces cerevisiae*.

Aspect 50. An extract produced by culturing the biological device of any of aspects 46-49 in a culture medium.

Aspect 51. The extract of aspect 50, wherein the extract is formulated as a liquid, a slurry, a powder, or a mixture thereof.

Aspect 52. A battery comprising an electrolyte, wherein the electrolyte comprises the extract of any aspect 50 or 51.

Aspect 53. An article or device comprising the extract of aspect 50 or 51 or the battery of aspect 44.

Aspect 54. The article or device of aspect 53, wherein the article or device comprises a standalone light, an indicator light on a larger device, a lighted panel on a larger device, a computer, a tablet, a smartphone, a medical device, a portable heating device, a portable cooling device, a grooming or personal care device, a lighted sign, a toy, a scientific instrument, a pump, a transportation device or vehicle, a kitchen device, or a household appliance.

Aspect 55. The article or device of aspect 53 or 54, wherein the device includes a light emitting diode.

Aspect 56. A method of culturing cells comprising growing the cells in a medium comprising the extract of aspect 50 or 51.

Aspect 57. The method of aspect 56, wherein the cells comprise bacteria or fungi.

Aspect 58. The method of aspect 57, wherein the bacteria or fungi comprise *Saccharomyces cerevisiae*, a *Kluyveromyces* species, a *Candida* species, a *Lactobacillus* species, *Pyrococcus furiosus*, *Thermus aquaticus*, *Bacillus stearothermophilus*, *Thermus filiformis*, *Thermus thermophiles*, a *Xanthomonas* species, *Aspergillus niger* or another *Aspergillus* species, a *Trichoderma* species, *Mucor miehei*, a *Rhizopus* species, a *Mortierella* species, *Clostridium acetobutylicum* or another *Clostridium* species, a *Streptomyces* species, a *Penicillium* species, *Acetobacter acetii*, *Bacillus thuringiensis* or another *Bacillus* species, *E. coli*, a *Klebsiella* species, or *Trichoderma polysporum*.

Aspect 59. A plant grown by the process comprising contacting plant gamete cells, a plant reproductive organ, or a plant callus with the extract of aspect 50 or 51.

Aspect 60. The plant of aspect 59, wherein the plant is produced by a method comprising the steps of:
a. contacting the plant callus with the extract;
b. culturing the plant callus; and
c. growing the plant from the plant callus.

Aspect 61. A pharmaceutical composition comprising the extract of aspect 50 or 51.

Aspect 62. The pharmaceutical composition of aspect 61, further comprising a UV-blocking agent.

Aspect 63. The pharmaceutical composition of aspect 62, wherein the UV-blocking agent is zinc oxide, titanium dioxide, a carotenoid, oxybenzone, octinoxate, homosalate, octisalate, octocrylene, avobenzone, or any combination thereof.

Aspect 64. A sunscreen comprising the extract of aspect 50 or 51.

Aspect 65. A paint, ink, dye, or stain comprising the extract of aspect 50 or 51.

Aspect 66. A plant coated with the extract of aspect 50 or 51.

Aspect 67. An agricultural product coated with the extract of aspect 50 or 51.

Aspect 68. The agricultural product of aspect 67, wherein the agricultural product comprises fruits, leaves, seeds, flowers, grains, nuts, stems, vegetables, or mushrooms.

Aspect 69. A method for improving a physiological property of a plant, the method comprising applying the extract of aspect 50 or 51 to the plant, wherein the property is improved compared to the property of the same plant that has not been applied the extract.

Aspect 70. The method of aspect 69, wherein the property comprises increased root tension, root length, hormone production, drought tolerance, disease resistance, photosynthesis, or any combination thereof.

Aspect 71. The method of aspect 69 or 70, wherein the plant is grass, trees, bushes, shrubs, flower, vines, coffee, soybean, or cotton.

Aspect 72. The method of aspect 71, wherein the grass is growing on a golf course, a lawn, or an athletic playing field.

Aspect 73. The method of any of aspects 60-72, wherein the extract is applied in an amount of from about 50 to about 200 mL per square meter of grass.

Aspect 74. The method of aspect 73, wherein about 75 mL of extract are applied per square meter of grass.

Aspect 75. The method of aspect 73, wherein about 150 mL of extract are applied per square meter of grass.

Aspect 76. The method of any of aspects 69-75, wherein the extract is applied twice per week.

Aspect 77. The method of any of aspects 69-75, wherein the extract is applied in combination with a second compound that promotes plant growth.

Aspect 78. The method of aspect 77, wherein the second compound is applied before the extract.

Aspect 79. The method of aspect 77, wherein the second compound is applied after the extract.

Aspect 80. The method of aspect 77, wherein the second compound is applied simultaneously with the extract.

Aspect 81. The method of aspect 77, wherein the second compound is a polysaccharide, a fertilizer, or a combination thereof.

Aspect 82. The method of any one of aspects 77-81, wherein the second compound is chitosan, a polyactive carbohydrate, or a combination thereof.

Aspect 83. The method of aspect 82, wherein the second compound is in an aqueous solution having a concentration of from about 0.01% to about 0.05%.

Aspect 84. The method of aspect 83, wherein the second compound has a concentration of about 0.02%.

Aspect 85. The method of aspect 81, wherein the fertilizer is activated sewage sludge.

Aspect 86. An article comprising the extract of aspect 50 or 51, wherein the article is coated with the extract, the extract is dispersed throughout the article, or a combination thereof.

Aspect 87. The article of aspect 86, wherein the article is made of glass, fiberglass, plastic, metal, wood, fabric, foam, rubber, latex, silicone, or any combination thereof.

Aspect 88. A method of reducing or preventing exposure of an item to UV radiation comprising applying to the item the extract in aspect 50 or 51.

Aspect 89. The method of aspect 88, wherein the extract blocks at least 50% of UV radiation from contacting the item.

Aspect 90. The method of aspect 88, wherein the extract blocks at least 50% of longwave UV radiation from contacting the item.

Aspect 91. The method of aspect 88, wherein the extract blocks at least 50% of shortwave UV radiation from contacting the item.

Aspect 92. The method of aspect 88, wherein the item comprises the skin of a subject.

Aspect 93. The method of aspect 88, wherein the item comprises an agricultural product.

Aspect 94. The method of aspect 88, wherein the item comprises a construction material, an aeronautical material, or an aerospace material.

Aspect 95. The method of aspect 88, wherein the item comprises a culture of a microorganism.

Aspect 96. The method of aspect 88, wherein the item comprises a culture of isolated human or animal cells.

Aspect 97. A method for reducing or preventing the growth of barnacles on a surface, the method comprising applying a paint comprising the extract in aspect 50 or 51 and chitosan to the surface.

Aspect 98. The method of aspect 97, wherein the chitosan is from 60% to 100% acetylated and has from 3 to 20 glucosamine units, N-acetylglucosamine units, or a combination thereof.

Aspect 99. A cosmetic composition comprising a physiologically acceptable medium and the extract of aspect 50 or 51.

Aspect 100. An optical film comprising the extract of aspect 50 or 51.

Aspect 101. A method of reducing or preventing exposure of an item to UV radiation comprising applying to the item the extract of aspect 50 or 51.

Aspect 102. The method of aspect 101, wherein the extract blocks at least 50% of UV radiation from contacting the item.

Aspect 103. The method of aspect 101, wherein the extract blocks at least approximately 50% of longwave UV radiation from contacting the item.

Aspect 104. The method of aspect 101, wherein the extract blocks at least approximately 50% of shortwave UV radiation from contacting the item.

Aspect 105. The method of aspect 101, wherein the item comprises the skin of a subject.

Aspect 106. The method of aspect 101, wherein the item comprises an agricultural product.

Aspect 107. The method of aspect 101, wherein the item comprises a construction material, and aeronautical, or an aerospace material.

Aspect 108. An article comprising the extract of aspect 50 or 51, wherein the article is coated with the extract, the extract is dispersed throughout the article, or a combination thereof.

Aspect 109. The article of aspect 108, wherein the article is made of glass, fiberglass, plastic, metal, wood, fabric, foam, rubber, latex, silicone, or any combination thereof.

Aspect 110. A composition comprising water, genelight extract of aspects 50-51, and one or more one or more polysaccharides.

Aspect 111. The composition of aspect 110, wherein the polysaccharide comprises chitosan, a polyactive carbohydrate, or a combination thereof.

Aspect 112. The composition of aspects 110-111, wherein the genelight extract is less than 1% by weight, less than 0.75% by weight, less than 0.5% by weight, less than 0.25% by weight, less than 0.1% by weight, less than 0.5% by weight, or less than 0.3% by weight of the composition.

Aspect 113. The composition of aspects 110-112, wherein chitosan is less than 1% by weight, less than 0.75% by weight, less than 0.5% by weight, less than 0.25% by weight, less than 0.1% by weight, less than 0.5% by weight, or less than 0.3% by weight of the composition.

Aspect 114. The composition of aspects 110-113, wherein the polyactive carbohydrate is less than 1% by weight, less than 0.75% by weight, less than 0.5% by weight, less than 0.25% by weight, less than 0.1% by weight, less than 0.5% by weight, or less than 0.3% by weight of the composition.

Aspect 115. A method for improving a physiological property of a plant, the method comprising applying to the plant a composition comprising water, RuBisCO, and a heat shock protein, wherein the property is improved compared to the property of the same plant that has not been applied the composition.

Aspect 116. The method of Aspect 115, wherein the property comprises increased root tension, root length, hormone production, drought tolerance, disease resistance, photosynthesis, or any combination thereof.

Aspect 117. The method of Aspect 115, wherein the plant is grass, trees, bushes, shrubs, flower, vines, coffee, soybean, or cotton.

Aspect 118. The method of Aspect 117, wherein the grass is growing on a golf course, a lawn, or an athletic playing field.

Aspect 119. The method of Aspect 115, wherein the heat shock protein comprises HSP70.

Aspect 120. The method of Aspect 115, wherein the composition is produced by culturing a biological device in a culture medium, wherein the biological device comprises host cells transformed with a DNA construct comprising the following genetic components: (a) a gene that expresses a heat shock protein, (b) a gene that expresses RuBisCO large subunit 1, (c) a gene that expresses tonB, (d) a gene that expresses hydrogenase, and (e) a gene that expresses p-type ATPase.

Aspect 121. The method of Aspect 120, wherein the gene that expresses a heat shock protein expresses HSP70.

Aspect 122. The method of Aspect 120, wherein the construct further comprises a gene that expresses a reporter protein.

Aspect 123. The method of Aspect 120, wherein the DNA construct comprises from 5' to 3' the following genetic components in the following order: (1) a gene that expresses a heat shock protein, (2) a gene that expresses RuBisCO large subunit 1, (3) a gene that expresses tonB, (4) a gene that expresses hydrogenase, and (5) a gene that expresses p-type ATPase.

Aspect 124. The method of Aspect 120, wherein the DNA construct comprises from 5' to 3' the following genetic components in the following order: (1) a gene that expresses a heat shock protein having SEQ ID NO. 1 or at least 70% homology thereto, (2) a gene that expresses RuBisCO large subunit 1 having SEQ ID NO. 2 or at least 70% homology thereto, (3) a gene that expresses tonB having SEQ ID NO. 3 or at least 70% homology thereto, (4) a gene that expresses hydrogenase having SEQ ID NO. 4 or at least 70% homology thereto, and (5) a gene that expresses p-type ATPase having SEQ ID NO. 5 or at least 70% homology thereto.

Aspect 125. The method of Aspect 120, wherein the DNA construct comprises from 5' to 3' the following genetic components in the following order: (1) a gene that expresses a heat shock protein having SEQ ID NO. 1 or at least 70% homology thereto, (2) a gene that expresses RuBisCO large subunit 1 having SEQ ID NO. 2 or at least 70% homology thereto, (3) a gene that expresses tonB having SEQ ID NO. 3 or at least 70% homology thereto, (4) an rrnB terminator, (5) an ara-BAD promoter, (6) a gene that expresses hydrogenase having SEQ ID NO. 4 or at least 70% homology thereto, and (7) a gene that expresses p-type ATPase having SEQ ID NO. 5 or at least 70% homology thereto.

Aspect 126. The method of Aspect 120, wherein the DNA construct comprises from 5' to 3' the following genetic components in the following order: (1) a gene that expresses hydrogenase, (2) a gene that expresses p-type ATPase, (3) a gene that expresses tonB, (4) a gene that expresses a heat shock protein, and (5) a gene that expresses RuBisCO large subunit 1.

Aspect 127. The method of Aspect 120, wherein the DNA construct comprises from 5' to 3' the following genetic components in the following order: (1) a gene that expresses hydrogenase having SEQ ID NO. 4 or at least 70% homology thereto, (2) a gene that expresses p-type ATPase having SEQ ID NO. 5 or at least 70% homology thereto, (3) a gene that expresses tonB having SEQ ID NO. 3 or at least 70% homology thereto, (4) a gene that expresses a heat shock protein having SEQ ID NO. 1 or at least 70% homology thereto, and (5) a gene that expresses RuBisCO large subunit 1 having SEQ ID NO. 2 or at least 70% homology thereto.

Aspect 128. The method of Aspect 120, wherein the construct further comprises a gene that expresses a dehydrogenase.

Aspect 129. The method of Aspect 120, wherein the DNA construct comprises from 5' to 3' the following genetic components in the following order: (1) a gene that expresses a heat shock protein, (2) a gene that expresses dehydrogenase, (3) a gene that expresses RuBisCO large subunit 1, (4) a gene that expresses tonB, (5) a gene that expresses hydrogenase, and (6) a gene that expresses p-type ATPase.

Aspect 130. The method of Aspect 120, wherein the DNA construct comprises from 5' to 3' the following genetic components in the following order: (1) a gene that expresses a heat shock protein having SEQ ID NO. 1 or at least 70% homology thereto, (2) a gene that expresses dehydrogenase having SEQ ID NO. 9 or at least 70% homology thereto, (3) a gene that expresses RuBisCO large subunit 1 having SEQ ID NO. 2 or at least 70% homology thereto, (4) a gene that expresses tonB having SEQ ID NO. 3 or at least 70% homology thereto, (5) a gene that expresses hydrogenase having SEQ ID NO. 4 or at least 70% homology thereto, and (6) a gene that expresses p-type ATPase having SEQ ID NO. 5 or at least 70% homology thereto.

Aspect 131. The method of Aspect 120, wherein the DNA construct comprises from 5' to 3' the following genetic components in the following order: (1) a gene that expresses hydrogenase, (2) a gene that expresses p-type ATPase, (3) a gene that expresses tonB, (4) a gene that expresses a heat shock protein, (5) a gene that expresses dehydrogenase, and (6) a gene that expresses RuBisCO large subunit 1.

Aspect 132. The method of Aspect 120, wherein the DNA construct comprises from 5' to 3' the following genetic components in the following order: (1) a gene that expresses hydrogenase having SEQ ID NO. 4 or at least 70% homology thereto, (2) a gene that expresses p-type ATPase having SEQ ID NO. 5 or at least 70% homology thereto, (3) a gene that expresses tonB having SEQ ID NO. 3 or at least 70% homology thereto, (4) a gene that expresses a heat shock protein having SEQ ID NO. 1 or at least 70% homology thereto, (5) a gene that expresses dehydrogenase having SEQ ID NO. 9 or at least 70% homology thereto, and (6) a gene that expresses RuBisCO large subunit 1 having SEQ ID NO. 2 or at least 70% homology thereto.

Aspect 133. The method of Aspect 120, wherein the DNA construct has SEQ ID NOS. 7, 8, 10, 11, or at least 70% homology thereto.

Aspect 134. The method of Aspect 120, wherein the DNA construct is incorporated in a vector.

Aspect 135. The method of Aspect 134, wherein the vector is a plasmid selected from the group consisting of pWLNEO, pSV2CAT, pOG44, pXTI, pSG, pSVK3, pBSK, pBR322, pYES, pYES2, pBSKII, pUC, or pBAD.

Aspect 136. The method of Aspect 120, wherein the host cells comprise bacteria or fungi.

Aspect 137. The method of Aspect 115, wherein the composition further comprises chitosan, a polyactive carbohydrate, or a combination thereof.

Aspect 138. The method of Aspect 137, wherein chitosan is less than 1% by weight of the composition.

Aspect 139. The method of Aspect 137, wherein the polyactive carbohydrate is less than 1% by weight of the composition.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the desired process. Only reasonable and routine experimentation will be required to optimize such processes and conditions.

Example 1: Preparation of DNA Construct for the Production of Genelight Cultures The DNA construct was composed of the genetic components described herein and assembled in plasmid vectors (e.g., pYES2, pBAD). Sequences of genes and/or proteins with desired properties were identified in GenBank; these included a gene that expresses HSP70, a gene that expresses RuBisCO large subunit 1, a gene that expresses tonB, a gene that expresses hydrogenase, and a gene that expresses P-type ATPase. These sequences were synthesized by CloneTex Systems, Inc. (Austin, TX). Other genetic parts were also obtained for inclusion in the DNA constructs including, for example, promoter genes (e.g., GAL1 promoter and/or araBAD promoter), reporter genes (e.g., EGFP), and terminator sequences (e.g., CYC1 terminator and/or rrnB terminator). These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes according to directions and using reagents provided by the enzymes' supplier (Promega). The complete insert, containing restriction sites on each end, was then ligated into the plasmid. Successful construction of the insert and ligation of the insert into the plasmid were confirmed by gel electrophoresis.

In some experiments, PCR-amplified pieces of all gene fragments were combined by using homologous recombination technology (Gibson Assembly).

Figure 2:
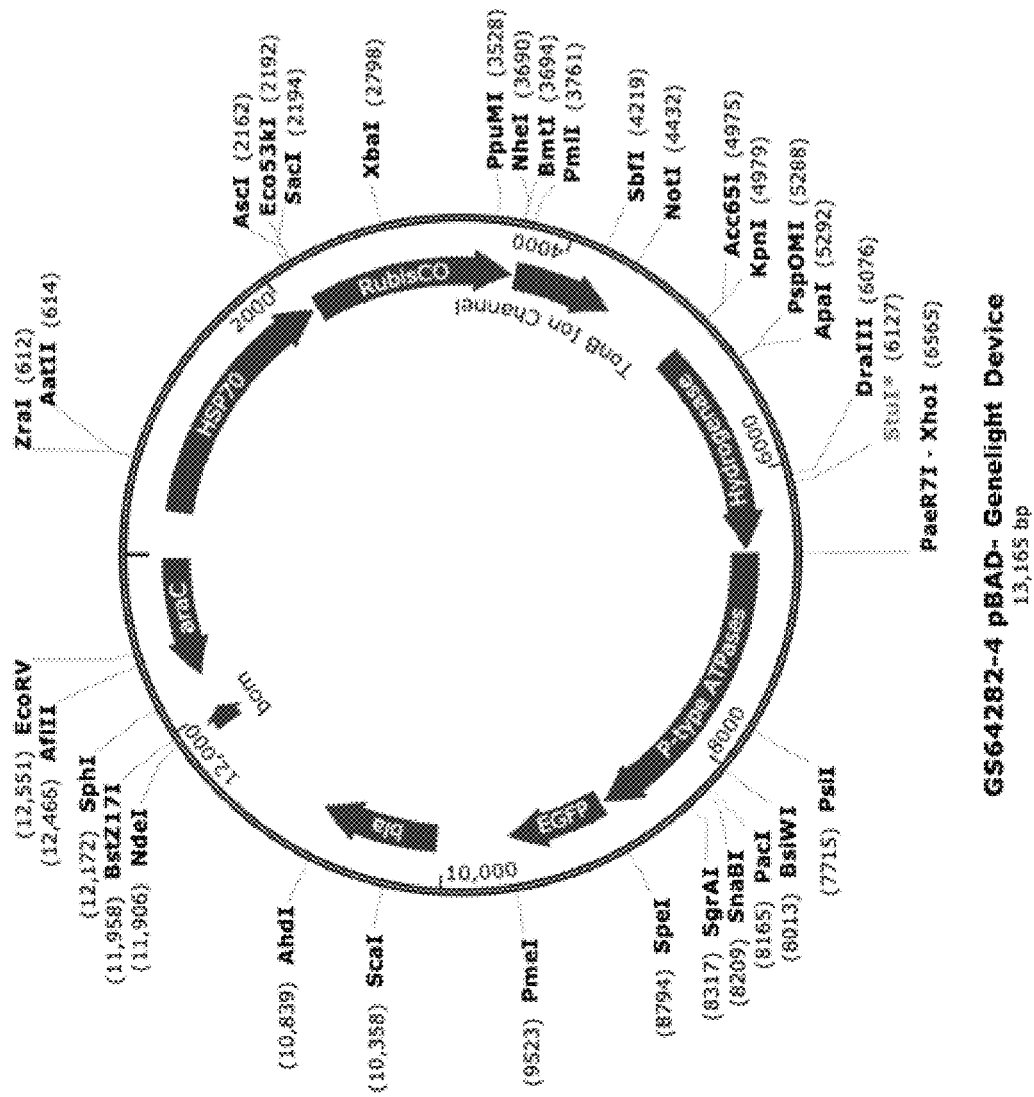
FIG. 2 shows a circular schematic of a constructed pBAD plasmid showing the direction, placement, and size of genetic parts used for an exemplary DNA device described herein.

From 5' to 3', one version of the construct includes (a) a gene that expresses HSP70, (b) a gene that expresses RuBisCO large subunit 1, (c) a gene that expresses tonB, (d) a gene that expresses rrnB terminator, (e) a gene that expresses araBAD promoter, (f) a gene that expresses hydrogenase, (g) a gene that expresses P-type ATPase, and (h) a gene that expresses EGFP (FIGS. 1 and 2).

Figure 3:
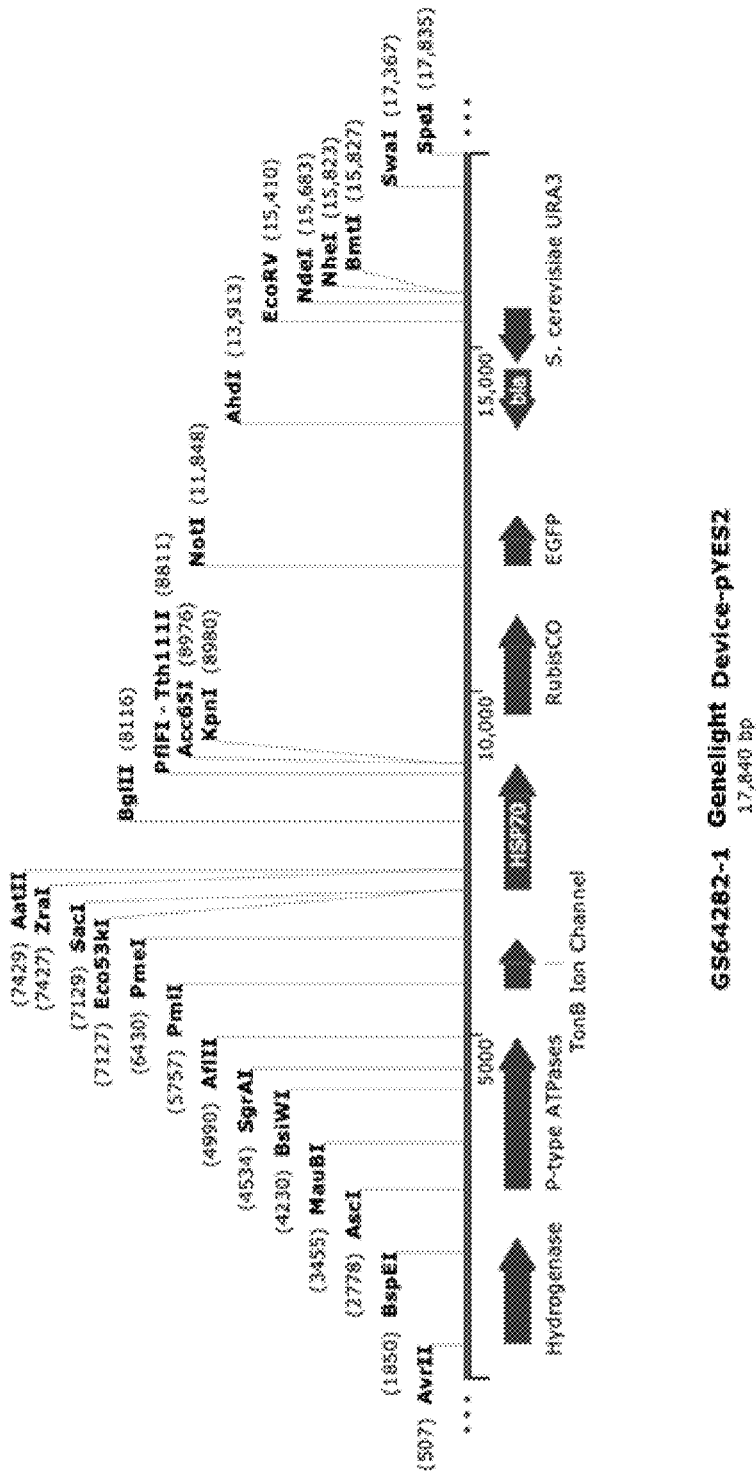
FIG. 3 shows a linear schematic of a constructed pYES2 plasmid showing the direction, placement, and size of genetic parts used for an exemplary DNA device described herein.
Figure 4:
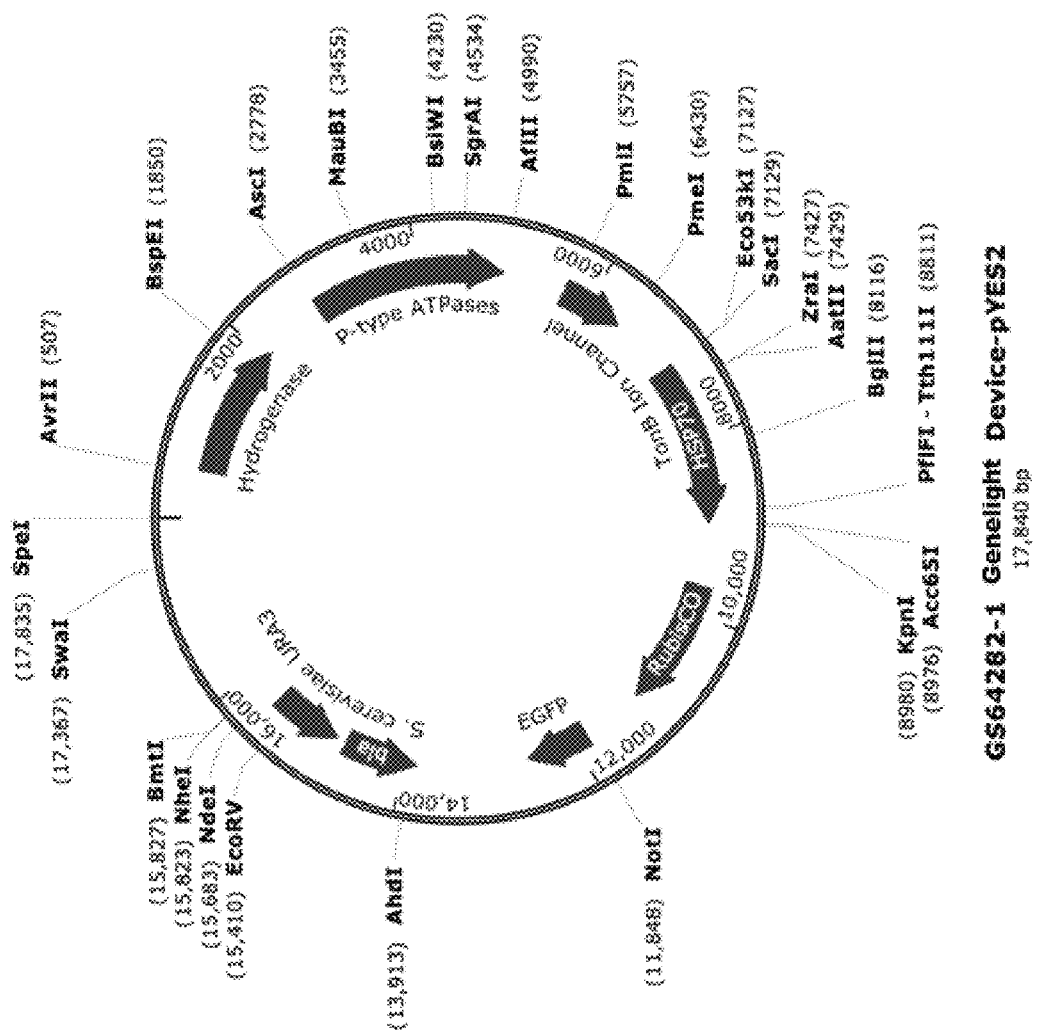
FIG. 4 shows a circular schematic of a constructed pYES2 plasmid showing the direction, placement, and size of genetic parts used for an exemplary DNA device described herein.

From 5' to 3', a second version of the construct includes (a) a gene that expresses hydrogenase, (b) a CYC1 terminator, (c) a GAL1 promoter, (d) a gene that expresses P-type ATPase, (e) a CYC1 terminator, (f) a GAL1 promoter, (g) a gene that expresses tonB, (h) a CYC1 terminator, (i) a GAL1 promoter, (j) a gene that expresses HSP70, (k) a CYC1 terminator, (l) a GAL1 promoter, (m) a gene that expresses RuBisCO large subunit 1, (n) a CYC1 terminator, (o) a GAL1 promoter, and (p) a gene that expresses EGFP (FIGS. 3 and 4).

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, *Molecular Cloning: A Laboratory Manual*, $2^{nd}$ ed., Vol. 1, Cold Spring Harbor Laboratory Press: Cold Spring Harbor, NY). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a NanoVue spectrophotometer (GE Life Sciences) and a standard UV/Visible spectrophotometer using the ratio of absorbances at 260 nm and 280 nm. In order to verify final ligations, DNA was visualized and purified via electrophoresis using a Thermo EC-150 power supply.

The DNA construct was made with gene parts fundamental for expression of sequences such as, for example, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the method described below.

A first DNA device for the production of genelight cultures and extracts was constructed by assembling a plasmid (pBAD) having the following genetic components in the following order: (a) a gene that expresses HSP70 having SEQ ID NO. 1, (b) a gene that expresses RuBisCO large subunit 1 having SEQ ID NO. 2, (c) a gene that expresses tonB having SEQ ID NO. 3, (d) an rrnB terminator, (e) an araBAD promoter, (f) a gene that expresses hydrogenase having SEQ ID NO. 4, (g) a gene that expresses P-type ATPase having SEQ ID NO. 5, and (h) a gene that expresses EGFP having SEQ ID NO. 6. The DNA construct having SEQ ID NO. 7 was transformed into cells, as described below, to produce the biological devices. Plasmids containing the first DNA device are shown in FIGS. 1 and 2.

A second DNA device for the production of genelight cultures and extracts were constructed by assembling a plasmid (pYES2) having the following genetic components in the following order: (a) a gene that expresses hydrogenase having SEQ ID NO. 4, (b) a CYC1 terminator, (c) a GAL1 promoter, (d) a gene that expresses P-type ATPase having SEQ ID NO. 5, (e) a CYC1 terminator, (f) a GAL1 promoter, (g) a gene that expresses tonB having SEQ ID NO. 3, (h) a CYC1 terminator, (i) a GAL1 promoter, (j) a gene that expresses HSP70 having SEQ ID NO. 1, (k) a CYC1 terminator, (l) a GAL1 promoter, (m) a gene that expresses RuBisCO large subunit 1 having SEQ ID NO. 2, (n) a CYC1 terminator, (o) a GAL1 promoter, and (p) a gene that expresses EGFP. The DNA construct having SEQ ID NO. 8 was transformed into cells, as described below, to produce the biological devices. Plasmids containing the second DNA device are shown in FIGS. 3 and 4.

Example 2: Selection of Microorganisms

In some experiments, the genelight cultures and extracts were produced using transfected yeasts (*Saccharomyces cerevisiae*, ATCC® 200892™). Bacterial devices were constructed with one *Escherichia coli* (catalogue no. C29871 from New England BioLabs).

Example 3: Development of Competent Yeast Cells

Yeast cells were made competent by subjecting them to an electrochemical process adapted from Gietz and Schiestl (*Nature Protocols*, 2007, 2:35-37). Briefly, a single yeast colony was inoculated into 100 mL YPD (yeast extract peptone dextrose) growth media. Yeast was grown overnight on a shaker at 30° C. to $OD_{600}$=1.0. (Acceptable results were obtained with $OD_{600}$ values ranging from 0.6 to 1.8.) Cells were centrifuged at 2000 rpm in a tabletop centrifuge and resuspended in 10 mL TEL buffer (10 mM Tris-HCl, 1 mM EDTA, 0.1 M LiAc, pH=7.5) and shaken vigorously overnight at room temperature. Cells were again centrifuged and resuspended in 1 mL TEL buffer. Cells prepared in this manner could be stored in the refrigerator for up to one month.

Example 4: Transformation of Microbial Cells to Produce Genelight Devices

Competent cells were stored in the freezer until needed. Cells were thawed on ice and 100 µL of competent cells in TEL buffer were placed in a sterile 1.5 mL microcentrifuge tube. To this was added 5 µL of a 10 mg/mL solution of salmon sperm DNA (carrier DNA). Transforming DNA was added in various amounts. From 1 to 5 µg was sufficient for plasmids from commercial sources, but more DNA was required when transforming yeast with artificial DNA constructs. 10 µL of the DNA device were added to the microcentrifuge tube containing the competent yeast cells and the contents of the tube were mixed. The DNA-yeast suspension was incubated for 30 min at room temperature.

A PLATE solution (consisting of 40% PEG-3350 in 1×TEL buffer) was prepared. 0.7 mL of PLATE solution was added to the DNA-yeast suspension and the contents were mixed thoroughly and incubated for 1 h at room temperature. The mixture was placed in an electromagnetic chamber for 30 minutes. Cells were then heated at 42° C. for 5-10 minutes and 250 µL aliquots were plated on yeast malt agar to which selective growth compounds had been added. Plates were incubated overnight at 30° C.

DNA expression and effectiveness of transformation were determined by fluorescence of the transformed cells expressed in fluorescence units (FSUs) using a 20/20 Luminometer (Promega) according to a protocol provided by the manufacturer. Plasmid DNA extraction, purification, PCR, and gel electrophoresis were also used to confirm transformation. Different transformed devices were obtained. Different types of fluorescent reporter proteins were used (e.g., yellow, red, green, and cyan) for all transformed cells and/or constructs. However, the green fluorescent protein EGFP was preferred. When no fluorescent reporter protein was assembled, no fluorescence was observed.

*S. cerevisiae* cells were subjected to transformation with the construct of SEQ ID. NO 8. Transformed yeast cells were incubated for 30 min at 28-30° C. Colonies of transformed yeast cells were selected, their DNA isolated and subjected to PCR amplification. Two control treatments were also carried out: (1) a negative control involving competent yeast and nuclease free water instead of a plasmid and (2) a positive control involving competent yeast with unmodified pYES2 plasmid. Transformed yeast were selected on a synthetic complete (SC) dropout plate deficient in uracil. A well-isolated clone was selected from the SC plate and preserved in YPD medium containing 15% glycerol for storage at −80° C. until later use.

Alternatively, the construct of SEQ ID. NO 8 was transformed into competent *E. coli* using a standard heat shock protocol. Four clones were selected from a transformed plate and processed for full-length DNA sequencing. A clone with 100% DNA sequence accuracy was selected for further processing and was used to obtain a high concentration of plasmid construct at a mid-scale plasmid purification level.

Example 5: Production of Microbial Extracts

*E. coli* cells transformed with SEQ ID NO 7 as described herein were grown in nutrient broth (25 mL of device inoculum in 1 L of medium) with 1 μg/mL ampicillin and 100 μM isopropyl β-D-1-thiogalactopyranoside (IPTG) at 37° C. for 96 hours. The cultures were then sonicated 7 times for a total of 2 min and 30 s and then autoclaved for 15 min.

*S. cerevisiae* cells transformed with SEQ ID NO 8 as described herein were grown in yeast malt medium (25 mL of device inoculum in 1 L of medium) with 1 mg/mL of glucosamine, 2% raffinose, and induction with 1% galactose at 30° C. for 72 hours. The cultures were then sonicated 7 times for a total of 2 min and 30 s and then autoclaved for 15 min.

Electrochemical Properties of Microbial Extracts

Electrochemical properties of the extracts produced as described above were measured using a MASTECH 19-Range Digital Multimeter (MAS830B), an Eclipse Tools LED Light Intensity Meter (MT-4617 LED), and a Hach HQ11D portable pH/ORP/mV meter for water (HQ11D53000000). For experiments requiring the construction of a circuit, 12 cm copper and zinc electrodes were used, and 5 tubes with 20 mL extract in each tube were used to construct the circuit. LEDs used were white in color. Properties for *S. cerevisiae* extracts are summarized in Table 8 below:

TABLE 8

| Selected Properties of *S. cerevisiae* Extracts | |
|---|---|
| Optical Density of Culture | 2.86 |
| Optical Density of Extract | 4.86 |
| Voltage | 5.3 V |
| Amperage | $2.0 \times 10^{-4}$ A |
| Lux | 22.6 lux |
| pH | 6.2 |
| Conductivity | 8.76 mS/cm |
| Redox | 71.3 mV |

Example 6: Construction of a Microbial Battery

Figure 5:
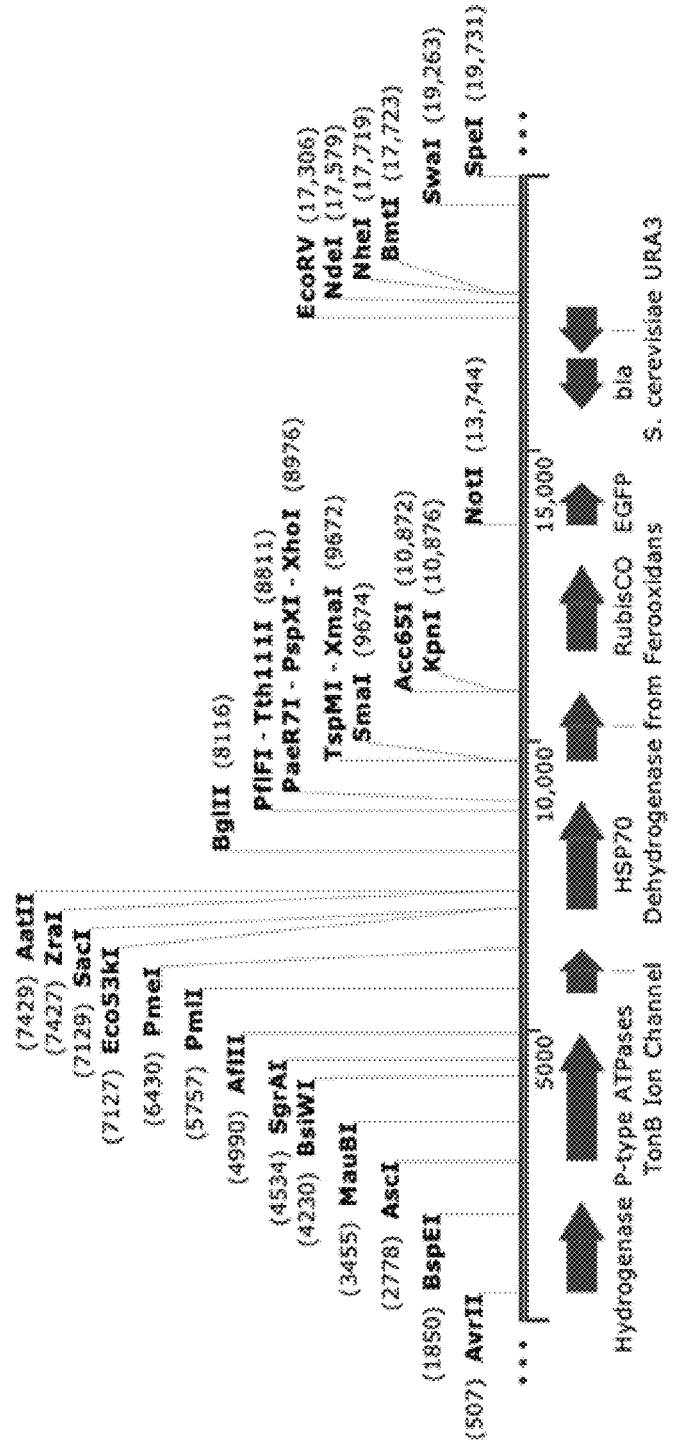
FIG. 5 shows a linear schematic of a constructed pYES2 plasmid showing the direction, placement, and size of genetic parts used for an exemplary DNA device described herein.
Figure 6:
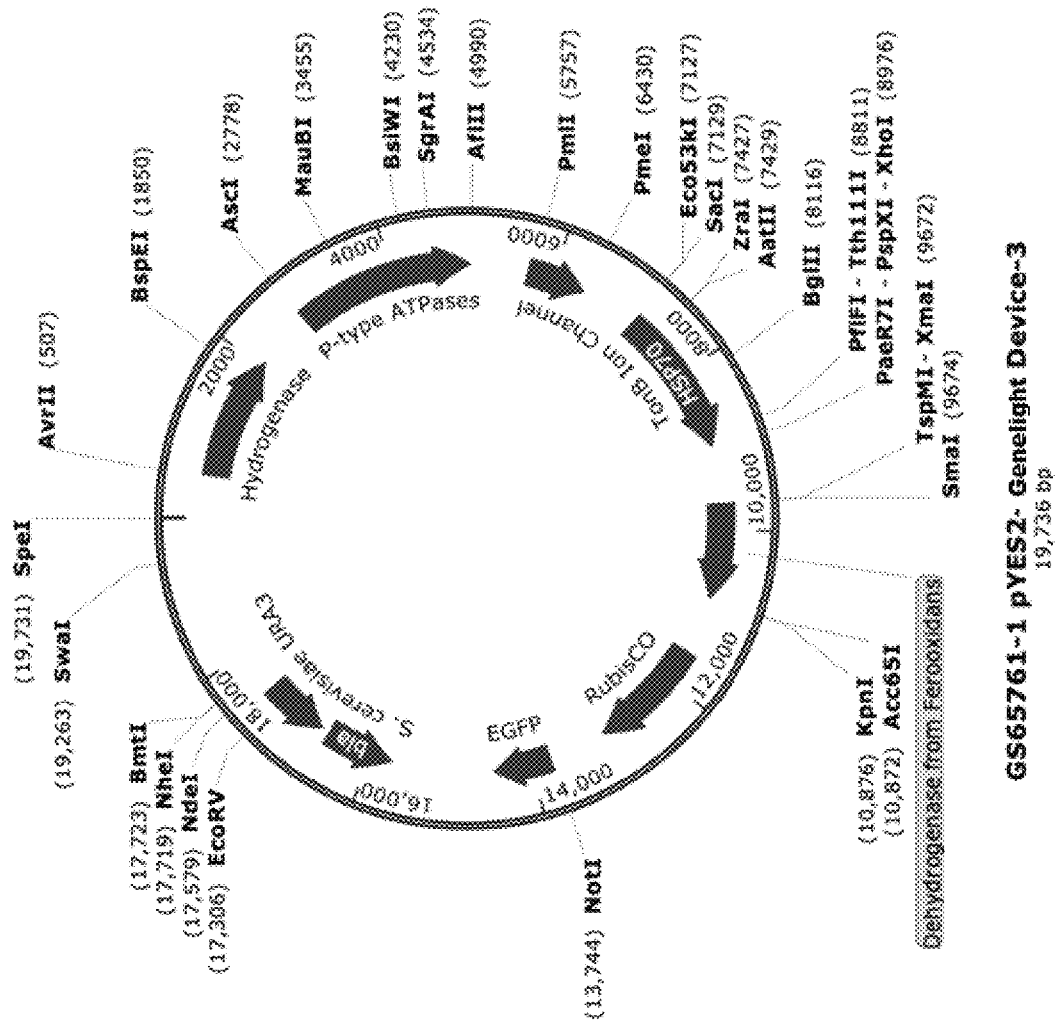
FIG. 6 shows a circular schematic of a constructed pYES2 plasmid showing the direction, placement, and size of genetic parts used for an exemplary DNA device described herein.

A microbial electrical circuit was constructed as follows (FIGS. 5 and 6A-6B). A series of tubes was arranged in either a linear or a parallel manner. Tubes with volume capacities of 10, 15, 20, and 50 mL were evaluated, but the 50 mL capacity tubes were preferred.

25 mL aliquots of extract produced from the *E. coli* transformed with SEQ ID NO 7 were placed in each tube. Five tubes were used for each experiment, but a higher number of tubes was workable if higher voltage was needed for the circuit.

Alternatively, a slurry of lyophilized extract and liquid extract was used. In a typical experiment, 1.5 g of lyophilized material and 150 μL of liquid extract were combined. Other mixtures were evaluated (1 g lyophilized extract and 50 μL of liquid extract, 1 g lyophilized extract and 200 μL of liquid extract, 2 g lyophilized extract and 200 μL of liquid extract) but were not preferred.

Following distribution of extract in the tubes, zinc and copper electrodes were introduced into each tube. Electrodes were connected to one another with appropriate wires and the circuit was closed using various colors of LED lights (e.g., white, blue, green, yellow, and red) at different luminescences or intensities. See FIG. 5 for an example microbial circuit compared to a traditional serial circuit. See also FIGS. 6A-6B wherein the microbial circuit is used to power an LED.

Effectiveness of different microbial extract circuits was assessed using commercial instruments. Voltage (V) and current (A) as well as intensity and luminescence (lux) were measured for the circuit and for light produced by the LEDs using a multimeter (MASTECH MAS830DB), a photometer (PROSKIT MT4617LD), and direct observation, as appropriate. Oxidation and reduction were measured with an electrode sensor (HATCH HQ11d).

Example 7: Protective Effect of Genelight Extracts on *Bacillus subtilis*

The UV-protective effects of the extracts disclosed herein were tested in *Bacillus subtilis* (ATCC® 82) cultures. *S. cerevisiae* cells transformed with SEQ ID NO 8 were fermented in yeast malt medium with 2% raffinose, 1 mg/mL glucosamine, and galactose for induction at 30° C. for 72 hours. The cultures were then sonicated 7 times for a total of 2 min, 30 sec. The supernatants were filtered using 8 μm, 5 μm, 2 and 1.2 μm filters and then used as-is in further experiments. Extracts produced from *E. coli* transformed with SEQ ID NO 7 were prepared as described previously.

Extinction Coefficient Determination

Extinction coefficient for the extracts disclosed herein was determined at 280 nm. Absorbance was measured using a microplate reader, with the molar extinction coefficient determined by the following equation:

$$\varepsilon = \frac{A \times l}{c \times V}$$

where ε is the extinction coefficient of the extract, A is absorbance, l is the area of the well in the microplate reader, c is the concentration of extract, and V is the sample volume. The extinction coefficient was based on a sample concentration of 7.7 mg/ml of genelight extract produced from *E. coli* and 9.0 mg/ml of genelight extract produced from yeast transformed with the SEQ ID NOS 7 and 8, respectively. Experimentally-determined extinction coefficients can be found in Table 9 below:

TABLE 9

| Extinction Coefficient (ε280) for Genelight Extracts | | |
|---|---|---|
| Device | ε | A |
| *E. coli*-based | 104 | 2.4 |
| *S. cerevisiae*-based | 122 | 3.3 |

Effects of Genelight Extracts on *Bacillus subtilis* Cultures

*B. subtilis* cultures were grown at 30° C. for 1-2 days. Aliquots were removed from culture and diluted to different concentrations to determine optimum concentration for further experiments. Experiments were spectrophotometric and optical densities (OD) of 0.5, 1.0, 1.4, and 2.0 were tested, with 1.4 found to be preferable. The above dilutions were mixed with different concentrations of genelight extracts prepared as described above to obtain different proportions (for example, a 5:2 ratio would indicate 5 parts extract versus 2 parts *B. subtilis* 1.4 OD culture). These solutions were placed in Petri dishes with a total volume of 7 mL; the experiments were conducted in triplicate.

Petri dishes were placed in a UV incubator and 1 mL samples were removed at different times (30 min, 1 hour, 2 hours) and thoroughly mixed. 500 μL aliquots of these samples were placed on nutrient agar using a standard streaking method. Three agar plate replicates were used each time; remaining portions of the aliquots were reserved for measurement of ATP. The agar plates were incubated at 30° C. for 1-4 days, following which, bacterial colonies of *B. subtilis* were viewed and counted.

Figure 7:
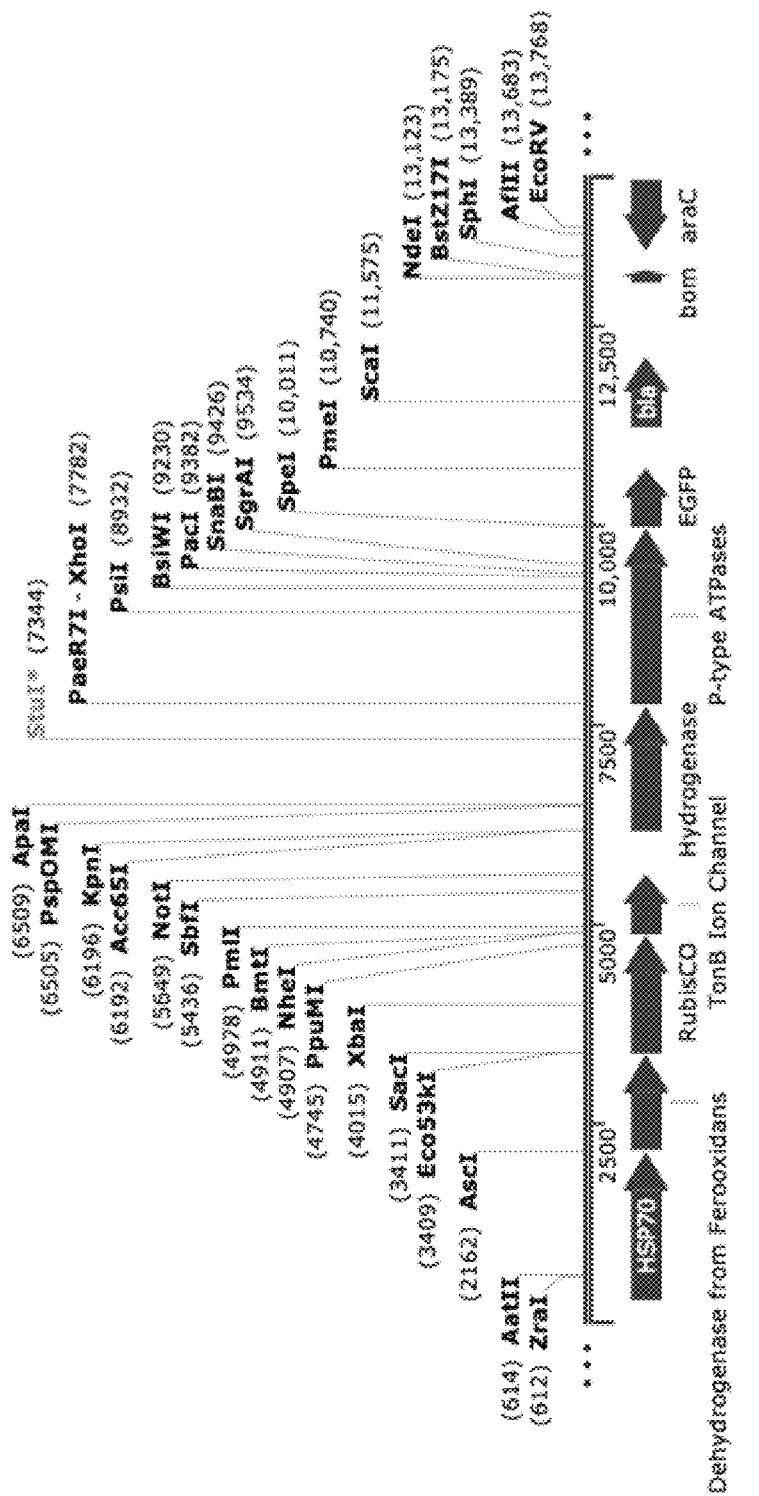
FIG. 7 shows a linear schematic of a constructed pBAD plasmid showing the direction, placement, and size of genetic parts used for an exemplary DNA device described herein.
Figure 8:
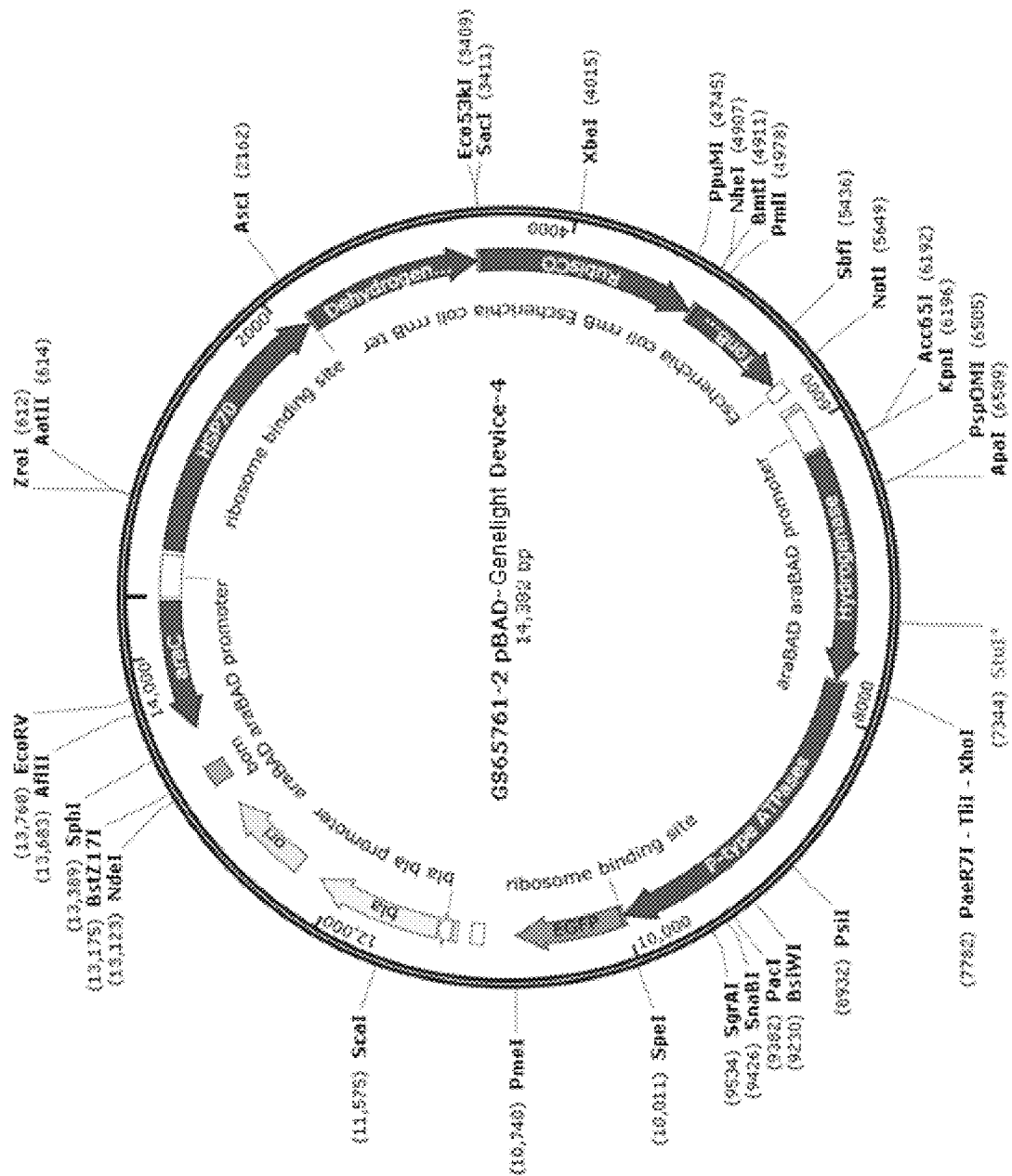
FIG. 8 shows a circular schematic of a constructed pBAD plasmid showing the direction, placement, and size of genetic parts used for an exemplary DNA device described herein.
Figure 9:
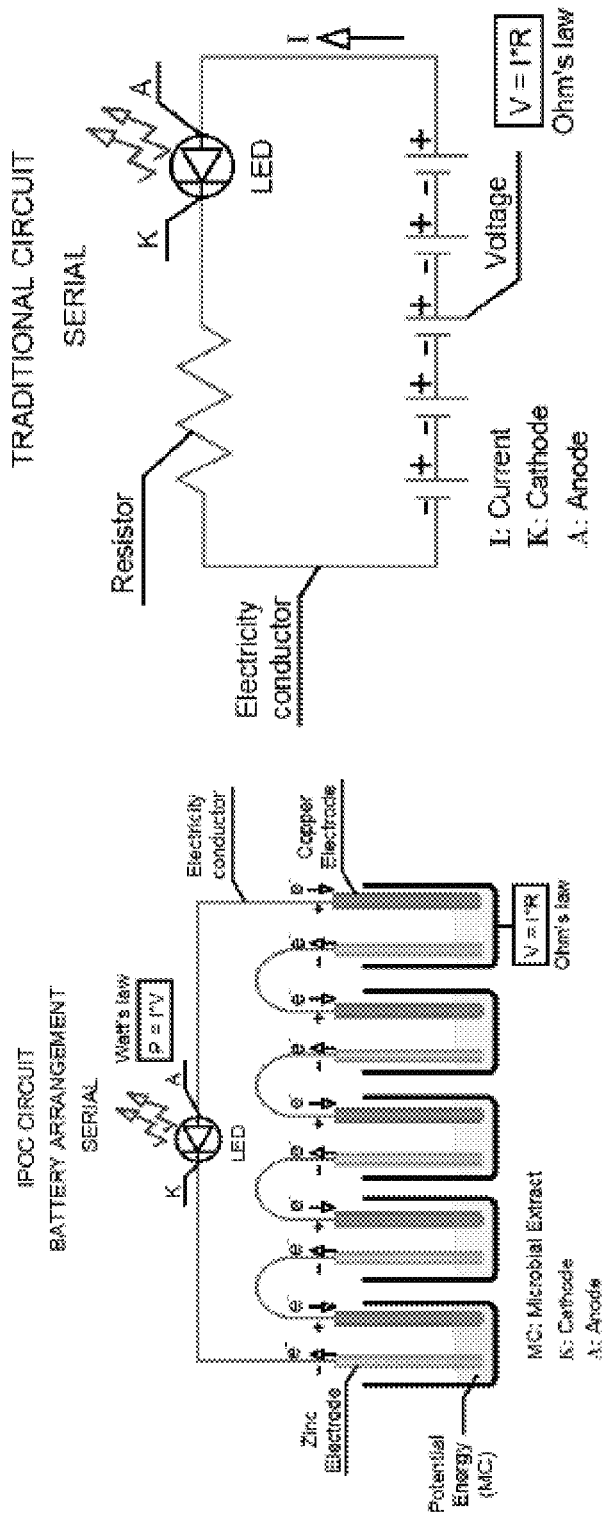
FIG. 9 shows a circuit constructed with the microbial extracts described herein including zinc and copper electrodes (left) and a standard circuit (right).
Figure 10A:
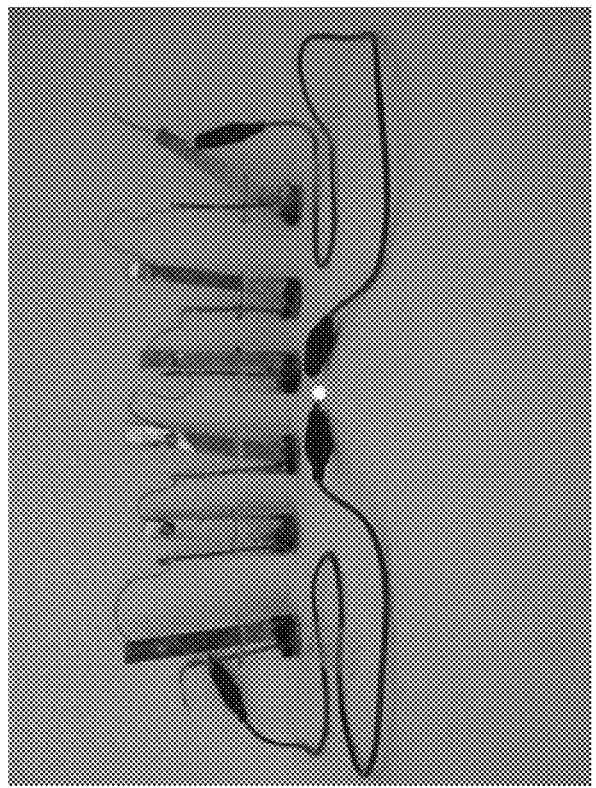
FIGS. 10A-10B show LED light production from a circuit constructed with the microbial extracts disclosed herein (both panels).
Figure 10B:
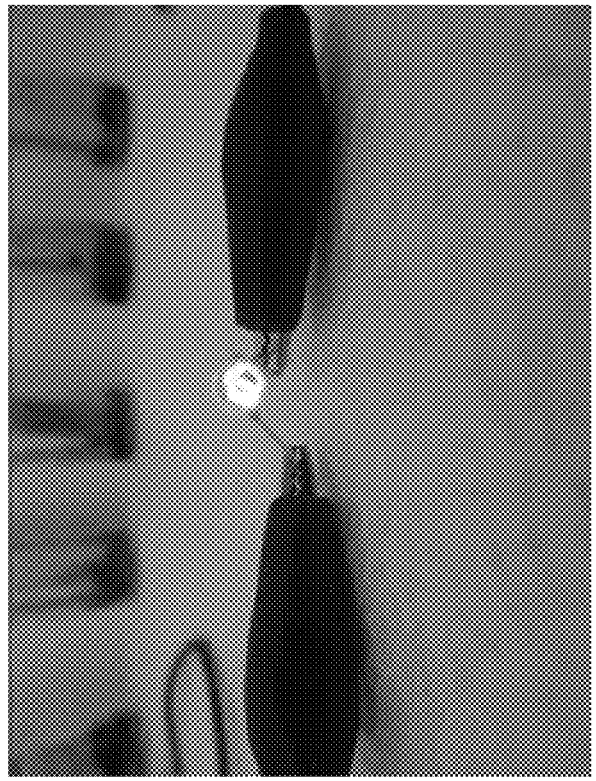
Figures 11A, 11B:
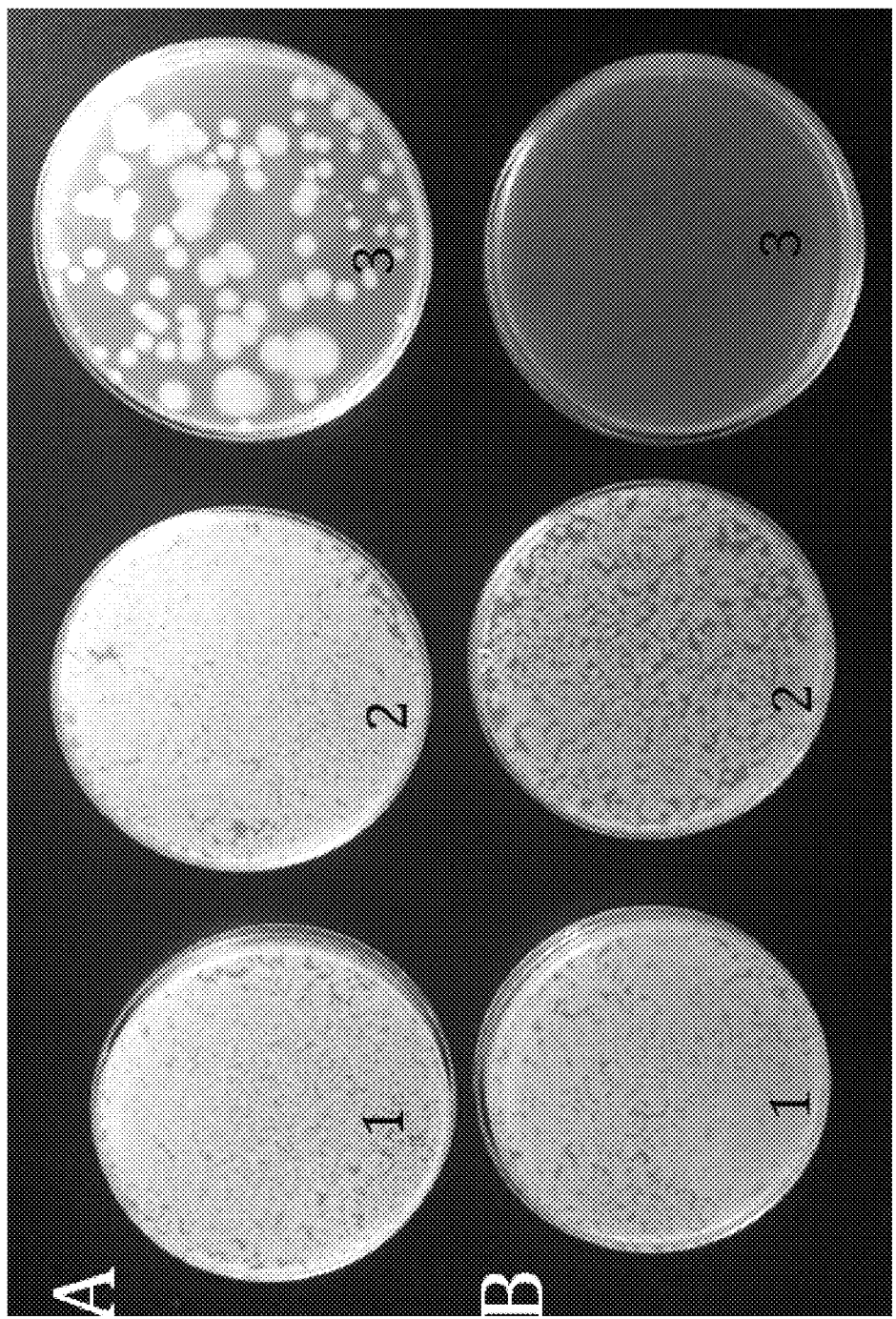
FIGS. 11A-11B shows *Bacillus subtilis* colonies after 30 minutes of UV exposure (7A) and after 2 hours of UV exposure (7B). Samples labeled 1 are *B. subtilis* cultures treated with extracts from the *E. coli* devices disclosed herein. Samples labeled 2 are *B. subtilis* cultures treated with extracts from the *S. cerevisiae* devices disclosed herein. Samples labeled 3 are *B. subtilis* controls (treated with water only).

FIGS. 7A and 7B shows *B. subtilis* colonies after 30 minutes (FIG. 7A) or 2 hours (FIG. 7B). Results from the *E. coli* based extracts are shown in the dishes marked 1, results from the *S. cerevisiae* experiments are shown in the dishes marked 2, and untreated controls with water added to make up the 7 mL volume are shown in the dishes marked 3. *B. subtilis* cultures treated with genelight extracts prior to UV irradiation exhibited higher counts of living cells and higher cell density than untreated controls.

Effects of Genelight Extracts on Human Fibroblast Cells

Extracts for fibroblast experiments were prepared as follows. *S. cerevisiae* cells transformed with SEQ ID NO 8 were fermented in yeast malt medium with 2% raffinose and induced with 1% galactose at 30° C. for 72 hours. Samples were sonicated 7 times for a total of 2 min and 30 sec and the supernatant was filtered through 8 μm, 5 μm, 3 μm, 2 μm, and 1.2 μm membranes.

Human skin fibroblasts (ATCC® CRL-2522) were maintained in culture media for propagation and renewal following ATCC® recommendations. Propagation medium was based on Eagle's Minimal Essential Medium including 0.025% trypsin and 0.03% EDTA. Fetal bovine serum was added to the medium to a final concentration of 10%. Medium was also renewed according to ATCC® instructions.

Fibroblast cells were grown at 37° C. under 5% $CO_2$.

Different proportions of extracts were applied to fibroblast cultures. The mixtures were then exposed to UV-B radiation at 302 nm for different periods of time and incubated at 37° C. and 5% $CO_2$. Each experiment was performed in triplicate. Aliquots of fibroblast cells were harvested and subjected to microscopic analysis, with dead, living, and apoptotic cells counted following staining with trypan blue. Cells were counted at 20× magnification using several microscopic field views. Results are presented in Table 10 below for samples composed of 5 parts genelight extract per 4 parts fibroblast culture:

TABLE 10

UV-Protective Effect of Genelight Cultures on Human Skin Fibroblasts

| Type of Cell | Control (Fibroblasts + Water) | | Treatment (Fibroblasts + Genelight Extract) | |
|---|---|---|---|---|
| (Percentages) | 30 min | 1 hour | 30 min | 1 hour |
| Live | 0 | 0 | 33 | 20 |
| Dead | 60 | 80 | 0 | 53 |
| Apoptotic | 40 | 20 | 67 | 27 |
| Total Survival | 40 | 20 | 100 | 47 |
| Protection | — | | 60 | 27 | where "live" cells appear as elongated cells without blue pigmentation, "dead" cells are spherical with intense blue pigmentation, and "apoptotic" cells are slightly curved and either lack pigmentation or are faintly pigmented. Total survival percentage is the sum of living and apoptotic cells, while protection percentage is the difference between total survival percentage of treated cultures and total survival percentage for the controls. Thus, more fibroblasts survived for a longer time when treated with the genelight extracts disclosed herein.

Total Genomic DNA from Fibroblast Cells

A QIAmp DNA Mini Kit (item 51304 from Qiagen) was used to determine total DNA in the fibroblast cells following UV exposure using a protocol provided by the manufacturer. DNA concentration was determined using the 260/280 nm ratio measured in a Lambda 25 UV/Vis Spectrophotometer (PerkinElmer). DNA was separated using 1.2% agarose gel electrophoresis with a voltage of 100 V. Gel results can be seen in FIG. 12 and are summarized in Table 11 below:

TABLE 11

Total Genomic DNA from Fibroblast Cells

| Treatment Group | DNA Concentration (ng/μL) |
|---|---|
| Cells Prior to Treatment | 37.8 |
| Cells Treated with *E. coli* Extracts | 31.8 |
| Cells Treated with *S. cerevisiae* Extracts | 10.2 |
| Untreated Cells (Water Control) | 14.2 |

Figure 12:
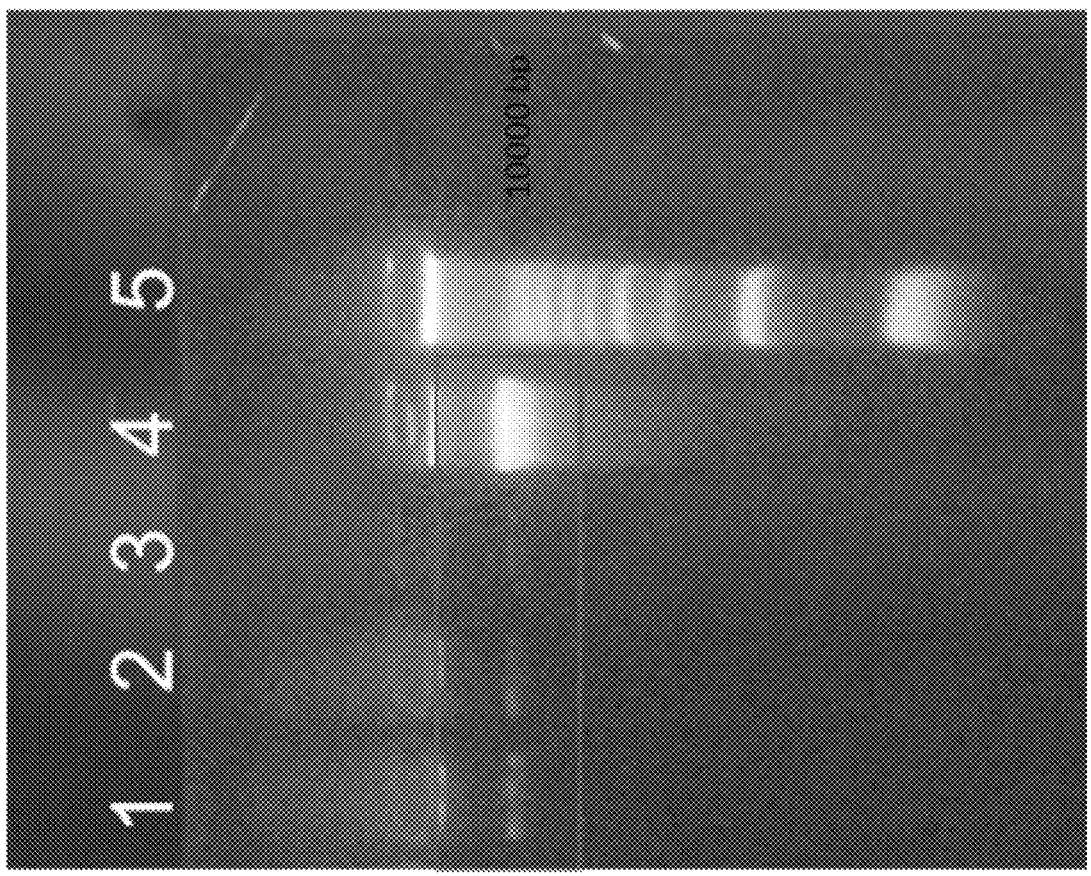
FIG. 12 shows quantitation of genomic DNA from human fibroblasts with and without treatment using the devices and extracts disclosed herein. Lane 1 shows DNA expression prior to any irradiation or treatment. Lane 2 shows DNA expression in human fibroblasts treated with extracts from *E. coli* devices as disclosed herein and then exposed to UV irradiation. Lane 3 shows DNA expression in human fibroblasts treated with extracts from *S. cerevisiae* devices as disclosed herein and then exposed to UV irradiation. Lane 4 shows DNA expression in human fibroblasts treated with water only and then exposed to UV irradiation. Lane 5 is a 1 kb DNA ladder.

FIG. 12 shows quantitation of genomic DNA from human fibroblasts with and without treatment using the devices and extracts disclosed herein. Lane 1 shows DNA expression prior to any irradiation or treatment. Lane 2 shows DNA expression in human fibroblasts treated with extracts from *E. coli* devices as disclosed herein and then exposed to UV irradiation. Lane 3 shows DNA expression in human fibroblasts treated with extracts from *S. cerevisiae* devices as disclosed herein and then exposed to UV irradiation. Lane 4 shows DNA expression in human fibroblasts treated with water only and then exposed to UV irradiation. Lane 5 is a 1 kb DNA ladder.

Example 8: Effect of Genelight Extracts on Plant Hormone Production

The effect of the microbial devices and extracts disclosed herein on root and plant development was assessed as follows. Extracts were prepared by culturing *E. coli* transformed with SEQ ID NO 7 in LB broth at 37° C. and 150 rpm with 1 μg/mL ampicillin. Induction was initiated with 2% raffinose and 100 μM IPTG. The culture was then sterilized in an autoclave for 15 min and sonicated 3 times for a total of 2 min and 30 sec.

Golf course soil was fertilized with Hou-Actinite prior to placing sod pieces of approximately 2,025 cm$^2$ in size. Experimental treatments were applied after the sod was placed on the soil and roots were not yet visible. Sod treated with the genelight cultures and extracts disclosed herein showed earlier rooting (within the first 48 hours) compared to a control (fertilized soil alone, with rooting after 48 hours). Treatment resulted in an improved appearance of the grass after two weeks.

Two applications of genelight extracts per week were made to the sod samples, using either 75 mL of extract per square meter of sod or 150 mL per square meter of sod. Three measurements were taken for each treatment and sampling time using a ruler to measure root length, and the mean of these measurements was calculated.

Root tension per area was measured using a tension meter and is expressed in Newtons (kg·m/s$^2$). The tension meter was placed on different parts of the sod (i.e., center and edges) and a mean from these three tension measurements was calculated. Tension forces were also determined for each plant and these results corroborate the larger-scale results. A higher value indicates more rooting per unit area, which means better anchoring of the plant to the soil. Sod treated with the extracts disclosed herein exhibited higher tension at about two times the value for the control of fertilizer alone. Root length and tension results for bacterial devices are summarized in Table 12 below:

TABLE 12

Root Length and Tension for Bacterial Devices

| Treatment | Dose (mL/ square meter) | Root Force for Sod (Tension/ Pressure) | Root Force for Single Plant (Tension/ Pressure) | Root Length (in) Days | | |
|---|---|---|---|---|---|---|
| | | | | 2 | 7 | 10 |
| E. coli extract | 150 | 21.33 | 4.33 | 1.5 | 2 | 2.5 |
| E. coli extract | 75 | 19.33 | 4.33 | 2 | 2.5 | 2.2 |

Yeast extracts were also tested. Root tension was measured for a 45×45 cm area chosen from a 1-square meter area of sod as well as for individual plants. Three replicates were tested for each measurement. Controls were also assessed wherein the area of sod was not treated but was only watered as normal. Root lengths were also measured as three replicates. Root length and tension results for yeast-based devices are summarized in Table 13 below:

TABLE 13

Root Length and Tension for Yeast Devices

| Treatment | Root Force for Sod (Tension/Area) | Root Force for Single Plant (Tension/Area) | Root Length (in) Week | | |
|---|---|---|---|---|---|
| | | | 1 | 2 | 5 |
| Control (Water) | 14 | 5.3 | 0.2 | 0.6 | 1.5 |
| Yeast Extract | 22 | 6.66 | 1 | 1.8 | 2.5 |

Example 9: Effect of Genelight Extracts on Uptake of Mineral Ions

The optimum concentration of the disclosed compositions and extracts to enhance uptake of mineral nutrients in Bermuda grass was assessed as follows. Extracts prepared from *E. coli* biological devices as described herein were used undiluted (1×) or were diluted 10-fold (10×), 50-fold (50×), 100-fold (100×), and 1000-fold (1000×). Extracts were used alone or in combination with chitosan and were compared to controls of polyactive carbohydrate as defined herein and of fertilizer (Hou-actinite) alone. Mineral nutrient levels for phosphorus, iron, magnesium, calcium, and potassium were evaluated.

For some experiments, metal concentration was measured using a Perkin-Elmer Nexlon 350X ICP-MS operating in a dual detector mode. Bermuda grass samples were processed as follows prior to performing ICP-MS analysis. Samples were ground to powder in dry ice and transferred in a metal-free tube. 2 mL (10× dilution) using 5% hydrogen peroxide and 1% nitric acid solution were added to the sample. The sample mixture was centrifuged at 1000 rpm for 2 min in order to obtain a homogeneous dispersion. An internal standard (indium, 10 ng/mL) was also added to the solution. Blank subtraction was applied after internal standard correction, with a 3-point calibration curve typically used to quantify compounds. The accuracy of the ICP-MS analytical protocol was periodically evaluated via the analysis of certified reference materials (serum and urine toxicology controls) from UTAK Laboratories, Inc. Results in mg of metal per kg of sample are presented in Tables 14A-14B below:

TABLE 14A

Mineral Ion Analysis in Bermuda Grass for *E. coli* Devices

| Treatment | Li | Na | Mg | Al | P | K | Ca | Ti | V | Cr | Mn | Fe |
|---|---|---|---|---|---|---|---|---|---|---|---|---|
| Chitosan 0.02% | 0.713 | 970 | 710 | 104 | 893 | 4508 | 2550 | 3.95 | 0.803 | 52.3 | 84.2 | 1281 |
| Polyactive Carbohydrate | 0.586 | 213 | 195 | 41 | <LOQ | 1060 | 890 | 2.43 | 0.317 | 12.2 | 13.6 | 253 |
| 1X Genelight Extract + Chitosan | 0.617 | 461 | 477 | 163 | 1006 | 4064 | 3085 | 6.11 | 0.691 | 6.15 | 51.1 | 520 |
| 1X Genelight Extract + Chitosan + Fertilizer | 0.555 | 336 | 234 | 66 | <LOQ | 1173 | 1515 | 3.33 | 0.534 | 7.39 | 36.7 | 371 |
| Polyactive Carbohydrate + Chitosan + Fertilizer | 0.571 | 104 | 92 | 50 | <LOQ | 728 | 588 | 2.47 | 0.354 | 19.1 | 15.9 | 336 |
| No Treatment | 0.638 | 457 | 357 | 72 | <LOQ | 1355 | 1741 | 3.37 | 0.482 | 10.1 | 28.1 | 394 |
| 1X Genelight Extract | 0.587 | 645 | 422 | 52 | 1051 | 3064 | 1566 | 3.28 | 0.491 | 24.3 | 52.8 | 521 |
| 10X Genelight Extract | 0.691 | 394 | 343 | 167 | 673 | 2529 | 2474 | 5.08 | 1.02 | 9.62 | 74.1 | 835 |
| 50X Genelight Extract | 0.730 | 714 | 417 | 120 | 1411 | 6202 | 3327 | 4.30 | 1.34 | 89.6 | 66.1 | 2073 |
| 100X Genelight Extract | 0.670 | 420 | 399 | 111 | 1028 | 4617 | 3783 | 4.08 | 0.913 | 23.2 | 53.7 | 778 |
| 1000X Genelight Extract | 0.548 | 156 | 193 | 57 | <LOQ | 1654 | 1560 | 3.51 | 0.377 | 6.49 | 53.2 | 262 |

TABLE 14B

Mineral Ion Analysis in Bermuda Grass for E. coli Devices

| Treatment | Co | Cu | Ge | As | Rb | Sr | Zr | Mo | Cs | Ba | La | W | Tl |
|---|---|---|---|---|---|---|---|---|---|---|---|---|---|
| Chitosan 0.02% | 0.489 | 9.18 | 0.148 | 0.307 | 2.40 | 20.9 | <LOQ | 2.46 | 0.063 | 24.6 | 0.959 | 0.124 | 0.029 |
| Polyactive Carbohydrate | 0.196 | 4.08 | 0.346 | 0.318 | 0.82 | 5.50 | <LOQ | 0.923 | <LOQ | 8.34 | 3.21 | 0.036 | 0.004 |
| 1X Genelight Extract + Chitosan | 0.307 | 5.16 | 0.171 | 0.461 | 2.86 | 19.9 | 0.498 | 1.10 | 0.099 | 16.1 | 1.37 | 0.069 | 0.015 |
| 1X Genelight Extract + Chitosan + Fertilizer | 0.332 | 4.30 | 0.114 | 0.300 | 0.86 | 8.62 | <LOQ | <LOQ | <LOQ | 10.7 | 0.728 | 0.145 | 0.004 |
| Polyactive Carbohydrate + Chitosan + Fertilizer | 0.198 | 3.69 | 0.127 | <LOQ | 0.65 | 4.15 | <LOQ | 0.956 | <LOQ | 9.53 | 0.648 | <LOQ | 0.004 |
| No Treatment | 0.243 | 4.62 | <LOQ | 0.297 | 0.88 | 11.5 | <LOQ | 1.35 | <LOQ | 15.9 | 0.873 | 0.034 | 0.005 |
| 1X Genelight Extract | 0.311 | 5.96 | 0.135 | <LOQ | 1.73 | 9.77 | <LOQ | 1.46 | <LOQ | 14.6 | 1.02 | 0.089 | 0.005 |
| 10X Genelight Extract | 0.777 | 5.49 | 0.135 | 0.335 | 1.49 | 13.3 | 0.445 | 1.15 | 0.072 | 13.6 | 0.926 | 0.188 | 0.005 |
| 50X Genelight Extract | 0.677 | 6.96 | 0.275 | 0.497 | 2.79 | 20.9 | 0.459 | 3.44 | <LOQ | 20.5 | 2.29 | 0.131 | 0.006 |
| 100X Genelight Extract | 0.392 | 6.28 | <LOQ | 0.367 | 2.35 | 17.5 | 0.414 | 1.56 | <LOQ | 13.6 | 0.744 | 0.088 | 0.006 |
| 1000X Genelight Extract | 0.218 | 4.18 | 0.127 | <LOQ | 1.00 | 6.95 | <LOQ | 1.04 | 0.062 | 10.6 | 1.01 | 0.052 | 0.005 |

These results demonstrate the efficacy of the 50× and 100× dilutions for enhancing uptake of mineral nutrients compared to a fertilizer control. 1× and 10× dilutions were also more effective than the control. The 1000× dilution showed higher potassium uptake and equal phosphorus uptake compared to a fertilizer control. Thus, treatment with the disclosed extracts over a wide range of dilutions equates to greater mineral uptake and healthier, better developed plants.

Example 10: Effect of Genelight Extracts on Chlorophyll Production

Chlorophyll a is the pigment in plants that acts directly in the reactions of photosynthesis requiring light, while chlorophyll b is an accessory pigment that acts indirectly in photosynthesis by transferring energy from the light it absorbs to chlorophyll a. The ratio of chlorophyll a to chlorophyll b in a typical chloroplast is about 3:1. Bermuda grass was treated with the extracts disclosed herein undiluted (B1) and with various dilutions (10× or B10; 50× or B50, 100× or B100, and 1000× or B1000) as well as with a control of fertilizer alone (Hou-actinite).

Samples were prepared as follows: 25 mL polypropylene tubes were labeled. Acetone to be used as the extraction solvent, previously prepared to include a vitamin E internal standard, was removed from the freezer and brought to room temperature. Grass samples were ground to powder and placed in the polypropylene tubes. 5 mL of 100% acetone containing the internal standard was added to each tube and the tubes were immediately covered with Parafilm and transferred to a −25° C. freezer for at least 30 min.

The samples were removed from the freezer and Parafilm was removed. A 47 mm GF/F sample filter was added to each tube and the tubes were re-covered. The samples were again transferred to a −25° C. freezer for 1 hour.

Samples were removed from the freezer and filters were macerated using an ultrasonic probe with a duty cycle of 90% and an output level of 5. Tubes were partially submerged in an ice and water bath during sonication to minimize heat accumulation. The condition of the sonicator tip was periodically monitored and polished using fine grade sandpaper to yield a smooth surface, and was rinsed with acetone and wiped with a Kimwipe between samples to prevent cross-contamination. This procedure required approximately 10 s and could be timed by counting the pulses emitted by the probe. Cavitation was prevented by pausing during sonication to push the filter slurry back down to the bottom of the tube if necessary.

After processing, samples were placed in a −25° C. freezer for 3-6 hours, then removed and filtered using a 0.45 μm PTFE syringe cartridge filter attached to a disposable plastic syringe. The pigment extract was collected in glass scintillation vials with foil-lined, labeled caps and the vials were placed in a dark environment.

After filtration, sample extracts were vortexed. Approximately 500 μL of each extract was transferred to an amber HPLC vial and capped with an HPLC cap having a silicone/PTFE liner. The vials were placed in a pre-chilled temperature-controlled autosampler and HPLC analysis was started. Unused extracts were stored in a freezer until the HPLC analyses were successfully completed.

HPLC analysis was conducted using a Supelcosil LC318 C18 column (25 cm×4.6 mm with 5 μm particle size for computer modeling work and 10 cm×4.6 mm with 5 μm particle size for pigment isolations). Flow rate was 1 mL/min. Mobile phase A was 70:30 (v/v) methanol and 28 mM aqueous TEAA, pH 6.5, while mobile phase B was methanol. A linear gradient of 5% (0 minutes) to 100% mobile phase B (20 minutes) was used for elution.

Relative amounts of chlorophyll a and chlorophyll b are given in Table 15 below:

TABLE 15

Primary Pigments per μg of Grass Sample after Treatment with E. coli Extracts

| Sample | Chlorophyll a | Chlorophyll b |
|---|---|---|
| B1 | 4835.148 | 1050.309 |
| B10 | 3054.033 | 817.857 |
| B50 | 843.357 | 249.964 |
| B100 | 5918.972 | 1343.685 |
| B1000 | 3509.713 | 978.343 |
| Control | 2827.165 | 680.853 |

The disclosed extracts and dilutions induce greater levels of both chlorophyll a and chlorophyll b compared to a fertilizer control, with the 100× (B100) dilution having the strongest effect.

Example 11: Effect of Genelight Extracts on Plant Hormone Production

Bermuda grass was grown for two weeks; during this time period, either extracts from the *E. coli* devices disclosed herein or a fertilizer control (Hou-actinite) were applied three times.

Samples were analyzed for plant hormones, chlorophyll, and minerals as described above. Hormone concentration and root length are based on the mean of three replicates, while mineral concentrations reported herein are based on single samples. Summarized results are presented in Table 16 below, while Tables 17A-17B contain a more detailed breakdown of additional plant hormones:

TABLE 16

Effect of Genelight Extracts on Plant Hormone Production

| Treatment | Hormone Quantity (ng/sample) | | | Mean Root Length (in) | Chlorophyll b (µg/sample) | Other Pigments (µg/sample) | Mineral Analysis (mg/kg) | | | |
|---|---|---|---|---|---|---|---|---|---|---|
| | Auxins | Jasmonic Acid | Salicylic Acid | | | | Mg | K | P | Ca |
| Genelight Extract (1X) | 243.33 | 25.94 | 3444.94 | 2.9 | 4291.216 | 2479.246 | 558 | 4064 | 1248 | 2165 |
| Control (fertilizer) | 115.56 | 2.21 | 859.43 | 1.5 | 3548.283 | 866.046 | 383 | 4340 | 1218 | 1590 |

TABLE 17A

Plant Hormone Production in Bermuda Grass for *E. coli* Devices

| Treatment | ABA[a] | SA[b] | cZ[c] | cZR[c] | tZr[c] | GA8[d] | GA12[d] | GA19[d] | GA24[d] | GA53[d] | IAA[e] | Methyl IAA[e] | IAA-Asp[e] |
|---|---|---|---|---|---|---|---|---|---|---|---|---|---|
| Chitosan 0.02% | 75.694 | 427.058 | 0.323 | 0.288 | ND | 39.451 | 35.310 | 5.115 | 9.665 | 29.506 | 330.577 | 0.749 | ND |
| Polyactive Carbohydrate | 85.055 | 406.050 | 0.301 | 0.178 | ND | 39.766 | 40.928 | 6.896 | 4.572 | 35.746 | 344.079 | 1.075 | ND |
| 1X Genelight Extract + Chitosan | 1.817 | 33.112 | 0.050 | 0.352 | 0.598 | 0.987 | ND | 1.706 | ND | 5.668 | 8.385 | 0.283 | 1.018 |
| 1X Genelight Extract + Chitosan + Fertilizer | 61.213 | 184.349 | 0.162 | 0.100 | ND | 28.684 | 33.537 | 6.282 | ND | 29.909 | 96.527 | 0.749 | ND |
| Polyactive Carbohydrate + Chitosan + Fertilizer | 47.455 | 202.524 | 0.182 | 0.202 | ND | 21.862 | 29.511 | 5.157 | ND | 30.244 | 76.893 | 0.452 | ND |
| No Treatment | 69.007 | 121.804 | 0.217 | 0.160 | ND | 24.916 | 38.246 | 4.338 | 5.815 | 29.860 | 32.888 | 0.291 | ND |
| 1X Genelight Extract | 60.067 | 125.501 | 0.126 | 0.111 | ND | 18.436 | 18.518 | 3.173 | 2.699 | 19.036 | 118.216 | 0.248 | ND |
| 10X Genelight Extract | 120.354 | 644.789 | 0.366 | 0.374 | ND | 57.394 | 30.603 | 6.039 | 18.698 | 45.071 | 632.977 | 0.496 | ND |
| 50X Genelight Extract | 12.628 | 20.616 | 0.054 | 0.271 | 0.113 | 10.381 | 6.566 | 1.773 | 1.968 | 7.333 | 15.234 | 0.230 | 4.476 |
| 100X Genelight Extract | 172.878 | 1440.829 | 0.411 | 0.328 | ND | 48.494 | 20.796 | 5.523 | 7.323 | 13.656 | 410.832 | 0.816 | ND |
| 1000X Genelight Extract | 91.438 | 318.869 | 0.260 | 0.304 | ND | 34.344 | 24.863 | 4.980 | 6.895 | 11.291 | 289.535 | 0.401 | ND |

TABLE 17B

Plant Hormone Production in Bermuda Grass for *E. coli* Devices

| Treatment | IAA-Trp[e] | JA[f] | JA-ILE[f] | OPDA[g] | Strigoi[h] |
|---|---|---|---|---|---|
| Chitosan 0.02% | ND | 17.804 | ND | 45.422 | ND |
| Polyactive Carbohydrate | ND | 15.020 | ND | 16.942 | ND |
| 1X Genelight Extract + Chitosan | ND | 1.645 | 0.094 | 3.447 | ND |
| 1X Genelight Extract + Chitosan + Fertilizer | ND | 6.944 | ND | 5.142 | ND |
| Polyactive Carbohydrate + Chitosan + Fertilizer | ND | 8.982 | ND | 15.776 | ND |
| No Treatment | ND | 5.926 | ND | 5.437 | 275.530 |
| 1X Genelight Extract | ND | 4.403 | ND | 2.743 | ND |
| 10X Genelight Extract | ND | 33.824 | ND | 96.835 | ND |
| 50X Genelight Extract | ND | 12.865 | 0.893 | 73.048 | ND |
| 100X Genelight Extract | ND | 27.209 | ND | 83.050 | ND |
| 1000X Genelight Extract | 0.509 | 8.859 | ND | 24.891 | ND |

[a]ABA = abscisic acid
[b]SA = salicylic acid
[c]cZ = cis-zeatin; cZr = cis-zeatin riboside; tZr = trans-zeatin riboside
[d]GA8 = gibberellin A(8); GA12 = gibberellin A(12); GA19 = gibberellin A(19); GA24 = gibberellin A(24); GA53 = gibberellin A(53)
[e]IAA = indole-3-acetic acid; MethylIAA = methyl-IAA; IAA-Asp = IAA conjugated with aspartic acid; IAA-Trp = IAA conjugated with tryptophan
[f]JA = jasmonic acid; JA-Ile = jasmonic acid conjugated with isoleucine
[g]OPDA = 12-oxo-phytodienoic acid
[h]Strigol = (+)-strigol These results indicate that higher induction of hormones related to root growth and stimulation of disease resistance in plants, as well as longer root lengths, occur with treatment using the disclosed extracts compared to a fertilizer control. Higher levels of chlorophyll b and magnesium are also found in grass treated with the disclosed extracts, indicating the disclosed extracts are better able to stimulate photosynthesis compared to a control.

Higher induction of other pigments and higher uptake of minerals including phosphorus, potassium, and calcium also occurred in grass treated with the disclosed compounds and extracts, compared to a fertilizer control.

Example 12. Characterization of Extract

Samples for Raman Spectroscopy:
1. Biolight E.Coli Device Extract, prepared through fermentation of E.Coli device in LB Broth at 37° C.
2. Culture was allowed to ferment for 48 hours then centrifuged, pellets were retained and media removed.
3. Pellets were then redissolved in sterile deionized water and sonicated to lyze cells.
4. The lysate was centrifuged and filtered through a 0.20 um filter and filtrate was retained and labeled as Biol E.Coli Device Extract.
5. The extract was purified and concentrated through Millipore Tangential Flow Filtration with a Pall filtration cartridge with a 5K molecular weight cut off.
6. The retentate was collected and 10 mL were lyophilized in a Harvest Right Scientific Freeze Drier at −40° C.
7. Approximately 20 mg of lyophilized sample was analyzed with a Renishaw Invia Confocal Raman Spectrometer.
8. The sample was placed on a glass slide directly in the confocal laser path.
9. The laser selected was 785 nm excitation laser, with 10 sec exposure and 4 acquisitions at 25° C.
10. Spectra was processed and analyzed using Wiley KnowitAll informatics systems 2020.

Figure 13:
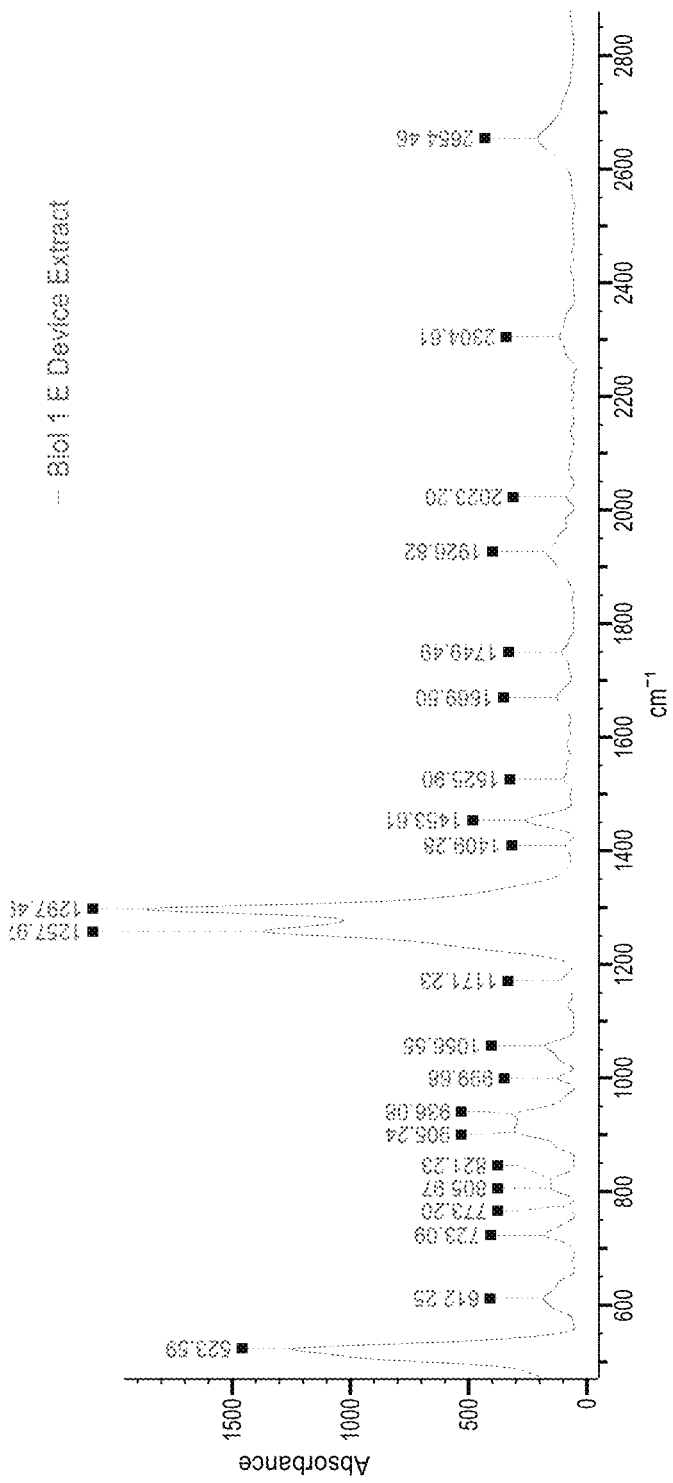
FIG. 13 shows the Raman spectrum of an extract of a genelight *E. coli* device.

As seen on FIG. 13, genelight $E.$ $coli$ extract is a mixture of proteins. Strong markers for proteins are the Amide I, II and III peaks at 1660, 1525, and 1297 cm', which are present in our Raman spectra. In addition, the presence of the monomeric protein thioredoxin is detected, since this protein has very specific peaks at 2300 & 2500 to 2600 cm' region.

The aromatic amino acids Phenylalanine and Tyrosine were detected. The respective peaks at 1000 $cm^{-1}$, 1050 $cm^{-1}$ and 620 $cm^{-1}$ for the Phenylalanine and the 1170 $cm^{-1}$, the fermi doublet at 830, 850 $cm^{-1}$ and the 650 $cm^{-1}$ peaks for Tyrosine are all present in the sample's spectra.

In addition Biolight 1 $E.$ $Coli$ Device Extract seems to have a mixture of unodered secondary protein structures and alpha helix structures noted by the strong peaks at 1257 $cm^{-1}$ (unordered) and 1297 $cm^{-1}$ (alpha helix).

Based on the ELISA assay determination, the Biolight 1 $E.$ $Coli$ Device Extract includes Rubisco and HSP70.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A method for improving a physiological property of a plant, the method comprising:
   applying to the plant a composition comprising an extract prepared from host cells cultured in a culture medium, said host cells transformed with a DNA construct comprising the following genetic components:
   (1) a gene that expresses a heat shock protein having at least 90% sequence identity to SEQ ID NO: 1,
   (2) a gene that expresses RuBisCO large subunit 1 having at least 90% sequence identity to SEQ ID NO: 2,
   (3) a gene that expresses tonB having at least 90% sequence identity to SEQ ID NO: 3,
   (4) a gene that expresses hydrogenase having at least 90% sequence identity to SEQ ID NO: 4, and
   (5) a gene that expresses p-type ATPase having at least 90% sequence identity to SEQ ID NO: 5,
   wherein the property is improved compared to the property of the same plant that has not been applied the composition, and wherein the physiological property comprises increased root tension, root length, hormone production, drought tolerance, disease resistance, photosynthesis, or any combination thereof.

2. The method of claim 1, wherein the property comprises increased root tension, root length, hormone production, drought tolerance, disease resistance, photosynthesis, or any combination thereof.

3. The method of claim 1, wherein the plant is grass, trees, bushes, shrubs, flower, vines, coffee, soybean, or cotton.

4. The method of claim 3, wherein the grass is growing on a golf course, a lawn, or an athletic playing field.

5. The method of claim 1, wherein the heat shock protein is HSP70.

6. The method of claim 1, wherein the construct further comprises a gene that expresses a reporter protein.

7. The method of claim 1, wherein the DNA construct comprises from 5' to 3' the following genetic components in the following order:
   (1) a gene that expresses a heat shock protein having at least 90% sequence identity to SEQ ID NO: 1,
   (2) a gene that expresses RuBisCO large subunit 1 having at least 90% sequence identity to SEQ ID NO: 2,
   (3) a gene that expresses tonB having at least 90% sequence identity to SEQ ID NO: 3,
   (4) a gene that expresses hydrogenase having at least 90% sequence identity to SEQ ID NO: 4, and
   (5) a gene that expresses p-type ATPase having at least 90% sequence identity to SEQ ID NO: 5.

8. The method of claim 1, wherein the DNA construct comprises from 5' to 3' the following genetic components in the following order:
   (1) a gene that expresses a heat shock protein having at least 90% sequence identity to SEQ ID NO: 1,
   (2) a gene that expresses RuBisCO large subunit 1 having at least 90% sequence identity to SEQ ID NO: 2, (3) a gene that expresses tonB having at least 90% sequence identity to SEQ ID NO: 3,
(4) an rrnB terminator,
(5) an araBAD promoter,
(6) a gene that expresses hydrogenase having at least 90% sequence identity to SEQ ID NO: 4, and
(7) a gene that expresses p-type ATPase having at least 90% sequence identity to SEQ ID NO: 5.

9. The method of claim 1, wherein the DNA construct comprises from 5' to 3' the following genetic components in the following order:
   (1) a gene that expresses hydrogenase having at least 90% sequence identity to SEQ ID NO: 4,
   (2) a gene that expresses p-type ATPase having at least 90% sequence identity to SEQ ID NO: 5,
   (3) a gene that expresses tonB having at least 90% sequence identity to SEQ ID NO: 3,
   (4) a gene that expresses a heat shock protein having at least 90% sequence identity to SEQ ID NO: 1, and
   (5) a gene that expresses RuBisCO large subunit 1 having at least 90% sequence identity to SEQ ID NO: 2.

10. The method of claim 1, wherein the construct further comprises a gene that expresses a dehydrogenase.

11. The method of claim 1, wherein the DNA construct comprises from 5' to 3' the following genetic components in the following order:
   (1) a gene that expresses a heat shock protein having at least 90% sequence identity to SEQ ID NO: 1,
   (2) a gene that expresses dehydrogenase having at least 90% sequence identity to SEQ ID NO: 9,
   (3) a gene that expresses RuBisCO large subunit 1 having at least 90% sequence identity to SEQ ID NO: 2,
   (4) a gene that expresses tonB having at least 90% sequence identity to SEQ ID NO: 3,
   (5) a gene that expresses hydrogenase having at least 90% sequence identity to SEQ ID NO: 4, and
   (6) a gene that expresses p-type ATPase having at least 90% sequence identity to SEQ ID NO: 5.

12. The method of claim 1, wherein the DNA construct comprises from 5' to 3' the following genetic components in the following order:
   (1) a gene that expresses hydrogenase having at least 90% sequence identity to SEQ ID NO: 4,
   (2) a gene that expresses p-type ATPase having at least 90% sequence identity to SEQ ID NO: 5,
   (3) a gene that expresses tonB having at least 90% sequence identity to SEQ ID NO: 3,
   (4) a gene that expresses a heat shock protein having at least 90% sequence identity to SEQ ID NO: 1,
   (5) a gene that expresses dehydrogenase having at least 90% sequence identity to SEQ ID NO: 9, and
   (6) a gene that expresses RuBisCO large subunit 1 having at least 90% sequence identity to SEQ ID NO: 2.

13. The method of claim 1, wherein the DNA construct has at least 90% sequence identity to SEQ ID NOs: 7, 8, 10 or 11.

14. The method of claim 1, wherein the DNA construct is incorporated in a vector.

15. The method of claim 14, wherein the vector is a plasmid selected from the group consisting of pWLNEO, pSV2CAT, pOG44, pXTI, pSG, pSVK3, pBSK, pBR322, pYES, pYES2, pBSKII, pUC, or pBAD.

16. The method of claim 1, wherein the host cells comprise bacteria or fungi.

17. The method of claim 1, wherein the composition further comprises chitosan, a polyactive carbohydrate, or a combination thereof.

18. The method of claim 17, wherein chitosan is less than 1% by weight of the composition.

19. The method of claim 17, wherein the polyactive carbohydrate is less than 1% by weight of the composition.

\* \* \* \* \*

SEQUENCE LISTING

<160> NUMBER OF SEQ ID NOS: 11

<210> SEQ ID NO 1
<211> LENGTH: 1854
<212> TYPE: DNA
<213> ORGANISM: Saccharomyces cerevisiae

<400> SEQUENCE: 1

```
ggtaccatgg ctgaaggtgt tttccaaggt gctatcggta tcgatttagg tacaacctac      60
tcttgtgttg ctacttacga atcctccgtt gaaattattg ccaacgaaca aggtaacaga     120
gtcaccccat ctttcgttgc tttcactcca gaagaaagat tgattggtga tgctgccaag     180
aaccaagctg ctttgaaccc aagaaacact gtcttcgatg ctaagcgttt gattggtaga     240
agattcgacg acgaatctgt tcaaaaggac atgaagacct ggcctttcaa ggttatcgac     300
gtcgatggta acccagtcat cgaagtccaa tacttggaag aaaccaagac tttctcccca     360
caagaaattt ccgctatggt tttgaccaag atgaaggaaa ttgctgaagc taagattggt     420
aagaaggttg aaaaggccgt cattactgtc ccagcttact taacgacgc tcaaagacaa      480 gctaccaagg atgccggtgc catttctggt ttgaacgttt tgcgtatcat caacgaacct     540
actgccgctg ctattgctta cggtctaggt gctggtaagt ccgaaaagga aagacatgtt     600 ttgatttcg atttgggtgg tggtactttc gatgtttcct tgttgcacat tgctggtggt      660
gtttacactg ttaaatctac ttccggtaac actcacttgg gtggtcaaga tttcgacacc     720
```

```
aacttgttgg aacacttcaa ggctgaattc aagaagaaga ctggtttgga catctccgac    780
gatgccagag ctttgagaag attgagaact gctgctgaaa gagctaagag aaccttatct    840
tctgtcactc aaactaccgt tgaagttgac tctttgtttg acggtgaaga tttcgaatcc    900
tctttgacta gagctagatt tgaagacttg aacgccgcat tgttcaagtc tactttggaa    960
cctgttgaac aagttttgaa ggatgctaag atctctaagt ctcaaatcga cgaagttgtc   1020
ttggttggtg gttccaccag aattccaaag tccaaaagt tgttgtctga cttctttgac   1080
ggtaagcaat tggaaaaatc tattaaccca gatgaagctg ttgcttacgg tgctgctgtt   1140
caaggtgcta tcttgaccgg ccaatccaca tctgacgaaa ccaaggactt gttgttgtta   1200
gatgttgctc cattatctct aggtgttggt atgcaaggtg acatgttcgg tatcgttgtt   1260
ccaagaaaca ctactgttcc aaccatcaag agaagaacct ttactacatg tgctgacaac   1320
caaaccaccg ttcaattccc agtctaccaa ggtgaacgtg ttaactgtaa agaaaacact   1380
ttgttgggtg aattcgactt gaagaacatc ccaatgatgc cagctggtga accagtcttg   1440
gaagctatct tcgaagttga tgctaacggt atcttgaagg ttactgccgt cgaaaagtct   1500
accggtaagt cttctaacat cactatctct aacgctgttg gtagattgtc ttctgaagaa   1560
attgaaaaga tggttaacca agctgaagag ttcaaggctg ccgatgaagc ttttgccaag   1620
aagcacgaag ctagacaaag attggaatcc tacgttgcct ccatcgaaca aactgtcact   1680
gacccagtct tgtcttctaa attgaagaga ggttccaagt ccaagattga agctgctttg   1740
tccgatgctt tggctgcttt gcaaatcgaa gacccatctg ctgatgaatt gagaaaggct   1800
gaagttggtt tgaagagagt tgtcaccaag gccatgtctt ctcgttaact cgag         1854

<210> SEQ ID NO 2
<211> LENGTH: 1491
<212> TYPE: DNA
<213> ORGANISM: Guillardia theta

<400> SEQUENCE: 2
aagcttggta ccatgtctca atccgtagaa tcacggactc gaatcaaaaa cgaacgttac     60
gaatcaggtg ttatccctta cgcaaaaatg ggatactggg atgctgatta cgttatcaaa    120
gatactgacg tacttgcaat gttccgtatg cacctcaaa aaggtgttga cccagttgaa     180
tgtgcagccg caatcgcagg tgaatcttca acagcaactt ggacagttgt atggacagac    240
cttctaacag catgtgatct ttaccgtgca aaagcatacc gtgttgaccc agttcctggt    300
gcaactgatc aatactttgc ttacatcgca tacgaattag acctatttga agaaggttct    360
ttagctaact aacagcatc aattattggt aacgtattcg gattcaaagc ggtaaatgct    420
ttaagattag aagatatgcg tcttccaatt gcatacctaa aaactttcca aggtccagca    480
actggtgtaa ttgtagaacg tgaaagatta gacaaatatg gtcgtccttt attaggtgca    540
acagttaaac caaaattagg tctatctggt aaaaactatg gtcgtgtagt ttacgaaggt    600
cttaaaggtg gtctagattt ccttaaagat gatgaaaaca ttaactctca accattcatg    660
agatggaaag agcgtttctt attcggtatc gaaggtgtaa accgtgctgc tgctgctgct    720
ggtgaagtaa aaggtcacta cttcaacgtt actgctggta caatggaaga tatgtatgaa    780
cgtgctgaat tctgtaaaga aatcggtagt gtaatctgta tgatcgacct tgtaatcgga    840
tatactgcta ttcaaagtat ggcgatctgg cacgtaaaaa acagtatgat tcttcactta    900
caccgtgctg gtaactctac atactcacgt caaaaaacac atggtatgaa cttccgtgta    960
```

| | |
|---|---|
| atttgtaagt ggatgcgtat ggcaggtgtt gaccacatac acgcaggtac agttgtaggt | 1020 |
| aaactagaag gggatccttt aatggttaaa ggtttctata acacattatt agaaacacaa | 1080 |
| acagatgtaa atcttgtaca aggtcttttc tttgctcaag attgggcagc acttaacaaa | 1140 |
| tgtatgccag ttgcttcagg tggtattcac tgtggtcaaa tgcaccaact tattaactac | 1200 |
| ttaggtgacg acgtagtatt acaatttggt ggtggtacta ttggtcaccc agatggtatc | 1260 |
| caagctggtg ctactgcaaa ccgtgtagca cttgaatgta tggttgtagc acgtaacgaa | 1320 |
| ggtcgtgact atgtaacaga gggtcctcaa attcttcgta atgcagctaa gagctgtgga | 1380 |
| cctcttcaaa cagcattaga tttatggaaa gacattactt tcaactatgc ttctactgat | 1440 |
| acagctgact tcgtagaaac tgcaacagct aacaagtaaa gatctctcga g | 1491 |

<210> SEQ ID NO 3
<211> LENGTH: 741
<212> TYPE: DNA
<213> ORGANISM: Pseudomonas entomophila

<400> SEQUENCE: 3

| | |
|---|---|
| gaattcatga cgaaaacgcg ctcgaacatg gcgcgctacg gcaccagcct ggccatcgtg | 60 |
| ctgggcgtgc acgtggtcgc cgtggtgctg acgctcaact ggtcggtgcc ccaggccatc | 120 |
| gagctgccgc cggcagcgat gatggtcgag ttggcgccgt tgccggagcc cgcgccaccg | 180 |
| ccaccgccca aggccgcgcc caagccaccg gcagaggtcg aggagccgcc gctgcccaag | 240 |
| ctggtggagg cccccaagcc gaagatcgcc atcgccaagc cgcccaagcc caaggccaag | 300 |
| ccgcagccgc ccaagcctga aaaaagcct gagccgccga aggacgaacc accggccaag | 360 |
| gacgatgtgg cggatacccc gccaagcaac gcgcagccgc agaaatcggc cgcaccggca | 420 |
| ccgagcatcg cctccaacag caatgccctg cccagctggc agagcgacct gctgcgccac | 480 |
| ctggccaagt acaagaagta cccggaagac gctcgccgtc gcggcctgca gggcatcaac | 540 |
| cgcctgcgct tcgtggtcga cgccgagggc aaggtagtct cgtactcgct ggccggaggc | 600 |
| tcgggcagcg cggcgctgga ccgggcgacc ctggaaatga tccgtcgcgc aggctccgta | 660 |
| ccgaagccgc cagcggagct gttgaacaat ggcacgatcg aagtcgtggc gccgttcgtc | 720 |
| tattccctgg accgacgcta a | 741 |

<210> SEQ ID NO 4
<211> LENGTH: 1580
<212> TYPE: DNA
<213> ORGANISM: Acidithiobacillus ferridurans

<400> SEQUENCE: 4

| | |
|---|---|
| cctagggcca ccatgactga acttggttct gatactttgc cctctgtggg ccagtggcaa | 60 |
| caaattctga ctgcgccacc cgtctggcag gtcaaggtgc agactgcatc ctggacaagt | 120 |
| gccgcgctgg cgctgcgcga tcagggcggg cgtttgctgg gattgtgggg agaggcgggc | 180 |
| catgaaaatg catttttta catacatgcg ctgggccttg gttcaaccgg atatttgtgg | 240 |
| atcactctga cggtgcaatc cagcgaggga caatttccct cgctggccga cattttttccc | 300 |
| gctgcctcgc ggatggagcg ggccctgtac gatcttacgg gaatcagggc ggcggggaat | 360 |
| gccgataccc ggccatggct ccgccatcag tgctggccag cggggatttt tccactgcgg | 420 |
| gagggacaac tggatggcag ttccttcggc gtggatggtg atgccgatta tccttttcaa | 480 |
| ttaatcgata gcgtggatgt ccaccagatt ccagtgggac cggtacacgc gggcaccatt | 540 |
| gagcccggac actttcgttt tcgtgtgtc ggtgaacaaa ttctgcgtct ggaagaacga | 600 |

```
ttgggataca cccacaaggg cgtcgaacgc cttttccaag atcgggatgt gtttgcgggt      660
gcgcgtctgg caggacgcat cagtggtgac actacagcgg gttatgcctg ggcctacagc      720
atggcggtgg aatccattgc ccgatgcgaa atcccgcctc gtgcagccgc tttgcgtgct      780
gtttgcctgg aacgggagcg catggccaac catctgggtg atcttgccgc tctggggaat      840
gacgctggct tcgccttctg tcagtcacaa ttcctgttca tcaaggaaag cctgctgcgc      900
gaaaaccagg aaattttcgg acaccgctat tgatggact gcattattcc cggtggtgta       960
gcttttgatc tgaactccgc gcaaacagcc gcgattcagc gtaacagtga atcctggcag     1020
cgcaccgtgc agcgtttgga cctcctcttg caggagcact ccgtctgcg ggatcgtctg      1080 gtgggtacag gaaaaattgt gccaccccgt gctgcagcac tcggtatggc ggggcttgcc     1140
ggccgcgcca gtggtcaggc ctgggatttg cgggtccagt ttccccatgc accttatcag     1200
aatctggatg tttccatgca gctttccccg gaaggtgacg tggccgcacg ctggcaattg     1260
cgctttcggg aattctatga gtctctgcgt ctgcagaccc agttgctgtt ggatctaccc     1320
agtggagatg tcagcgcaac cattccggaa agcatccccg atggcgaagg cttgggcatt     1380
gtcgaagcat ggcgcggcga ggtctttgtc gccctatctg tggaaaacgc ccgtattaaa     1440
cgctgccatc cccacgatcc ctcgtggacc ctctggccgg tccttgagga ggccgtgctg     1500
aacgatattg ttgccgactt tccgctgatc aataaatcgt tcaatttgag ttacagcgga     1560
catgatttat aattaattaa                                                1580

<210> SEQ ID NO 5
<211> LENGTH: 2219
<212> TYPE: DNA
<213> ORGANISM: Escherichia coli

<400> SEQUENCE: 5
ggcgcgccac catgtcgact cctgacaatc acggcaagaa agcccctcaa tttgctgcgt       60
tcaaaccgct aaccacggta cagaacgcca acgactgttg ctgcgacggc gcatgttcca      120
gcacgccaac tctctctgaa aacgtctccg gcacccgcta tagctggaaa gtcagcggca      180
tggactgcgc cgcctgtgcg cgcaaggtag aaaatgccgt gcgccagctt gcaggcgtga      240
atcaggtgca ggtgttgttc gccaccgaaa aactggtggt cgatgccgac aatgacattc      300
gtgcacaagt tgaatctgcg ctgcaaaaag caggctattc cctgcgcgat gaacaggccg      360
ccgaagaacc gcaagcatca cgcctgaaag agaatctgcc gctgattacg ctaatcgtga      420
tgatggcaat cagctggggt ctggagcagt tcaatcatcc gttcgggcaa ctggcgttta      480
tcgcgaccac gctggttggg ctgtacccga ttgctcgtca ggcattacgg ttgatcaaat      540
ccggcagcta cttcgccatt gaaaccttaa tgagcgtagc cgctattggt gcactgttta      600
ttggcgcaac ggctgaagct gcgatggtgt tgctgctgtt tttgattggt gaacgactgg      660
aaggctgggc cgccagccgc gcgcgtcagg gcgttagcgc gttaatggcg ctgaaaccag      720
aaaccgccac gcgcctgcgt aagggtgagc gggaagaggt ggcgattaac agcctgcgcc      780
ctggcgatgt gattgaagtc gccgcaggtg ggcgtttgcc tgccgacggt aaactgctct      840
caccgtttgc cagttttgat gaaagcgccc tgaccggcga atccattccg gtggagcgcg      900
caacgggcga taaagtccct gctggtgcca ccagcgtaga ccgtctggtg acgttggaag      960
tgctgtcaga accgggagcc agcgccattg accggattct gaaactgatc gaagaagcca     1020
aagagcgtcg cgctcccatt gagcggttta tcgaccgttt cagccgtatc tatacgcccg     1080
```

| | | | | |
|---|---|---|---|---|
| cgattatggc | cgtcgctctg | ctggtgacgc | tggtgccacc | gctgctgttt gccgccagct | 1140 |
| ggcaggagtg | gatttataaa | gggctgacgc | tgctgctgat | tggctgcccg tgtgcgttag | 1200 |
| ttatctcaac | gcctgcggcg | attacctccg | ggctggcggc | ggcagcgcgt cgtggggcgt | 1260 |
| tgattaaagg | cggagcggcg | ctggaacagc | tgggtcgtgt | tactcaggtg gcgtttgata | 1320 |
| aaaccggtac | gctgaccgtc | ggtaaaccgc | gcgttaccgc | gattcatccg gcaacgggta | 1380 |
| ttagtgaatc | tgaactgctg | acactggcgg | cggcggtcga | gcaaggcgcg acgcatccac | 1440 |
| tggcgcaagc | catcgtacgc | gaagcacagg | ttgctgaact | cgccattccc accgccgaat | 1500 |
| cacagcgggc | gctggtcggg | tctggcattg | aagcgcaggt | taacggtgag cgcgtattga | 1560 |
| tttgcgctgc | cgggaaacat | cccgctgatg | catttactgg | tttaattaac gaactggaaa | 1620 |
| gcgccgggca | acggtagtg | ctggtagtac | gtaacgatga | cgtgcttggt gtcattgcgt | 1680 |
| tacaggatac | cctgcgcgcc | gatgctgcaa | ctgccatcag | tgaactgaac gcgctgggcg | 1740 |
| tcaaaggggt | gatcctcacc | ggcgataatc | cacgcgcagc | ggcggcaatt gccggggagc | 1800 |
| tggggctgga | gtttaaagcg | ggcctgttgc | cggaagataa | agtcaaagcg gtgaccgagc | 1860 |
| tgaatcaaca | tgcgccgctg | gcgatggtcg | gtgacggtat | taacgacgcg ccagcgatga | 1920 |
| aagctgccgc | catcggggatt | gcaatgggta | gcggcacaga | cgtggcgctg gaaaccgccg | 1980 |
| acgcagcatt | aacccataac | cacctgcgcg | gcctggtgca | aatgattgaa ctggcacgcg | 2040 |
| ccactcacgc | caatatccgc | cagaacatca | ctattgcgct | ggggctgaaa gggatcttcc | 2100 |
| tcgtcaccac | gctgttaggg | atgaccgggt | tgtggctggc | agtgctggca gatacggggg | 2160 |
| cgacggtgct | ggtgacagcg | aatgcgttaa | gattgttgcg | caggagataa taacttaag | 2219 |

<210> SEQ ID NO 6
<211> LENGTH: 717
<212> TYPE: DNA
<213> ORGANISM: Artificial Sequence
<220> FEATURE:
<223> OTHER INFORMATION: Synthetic Construct

<400> SEQUENCE: 6

| | | | | |
|---|---|---|---|---|
| atgtctaaag | gtgaagaatt | attcactggt | gttgtcccaa | ttttggttga attagatggt | 60 |
| gatgttaatg | gtcacaaatt | ttctgtctcc | ggtgaaggtg | aaggtgatgc tacttacggt | 120 |
| aaattgacct | taaaatttat | ttgtactact | ggtaaattgc | cagttccatg gccaacctta | 180 |
| gtcactactt | tcggttatgg | tgttcaatgt | tttgctagat | acccagatca tatgaaacaa | 240 |
| catgactttt | tcaagtctgc | catgccagaa | ggttatgttc | aagaaagaac tatttttttc | 300 |
| aaagatgacg | gtaactacaa | gaccagagct | gaagtcaagt | ttgaaggtga taccttagtt | 360 |
| aatagaatcg | aattaaaagg | tattgatttt | aagaagatg | gtaacatttt aggtcacaaa | 420 |
| ttggaataca | actataactc | tcacaatgtt | tacatcatgg | ctgacaaaca aaagaatggt | 480 |
| atcaaagtta | acttcaaaat | tagacacaac | attgaagatg | gttctgttca attagctgac | 540 |
| cattatcaac | aaaatactcc | aattggtgat | ggtccagtct | tgttaccaga caaccattac | 600 |
| ttatccactc | aatctgcctt | atccaaagat | ccaaacgaaa | agagagacca catggtcttg | 660 |
| ttagaatttg | ttactgctgc | tggtattacc | catggtatgg | atgaattgta caaataa | 717 |

<210> SEQ ID NO 7
<211> LENGTH: 13165
<212> TYPE: DNA
<213> ORGANISM: Artificial Sequence
<220> FEATURE:
<223> OTHER INFORMATION: Synthetic Construct

<400> SEQUENCE: 7

```
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcctacctg acgcttttta tcgcaactct ctactgtttc tccatacccg ttttttgggc     300
taacaggagg aattaaccat ggctgaaggt gttttccaag gtgctatcgg tatcgattta     360
ggtacaacct actcttgtgt tgctacttac gaatcctccg ttgaaattat tgccaacgaa     420
caaggtaaca gagtcacccc atctttcgtt gctttcactc cagaagaaag attgattggt     480
gatgctgcca agaaccaagc tgctttgaac ccaagaaaca ctgtcttcga tgctaagcgt     540
ttgattggta agagattcga cgacgaatct gttcaaaagg acatgaagac ctggcctttc     600
aaggttatcg acgtcgatgg taacccagtc atcgaagtcc aatacttgga agaaaccaag     660
actttctccc cacaagaaat tccgctatgt gttttgacca agatgaagga aattgctgaa     720
gctaagattg gtaagaaggt tgaaaaggcc gtcattactg tcccagctta ctttaacgac     780
gctcaaagac aagctaccaa ggatgccggt gccatttctg gtttgaacgt tttgcgtatc     840
atcaacgaac ctactgccgc tgctattgct tacggtctag gtgctggtaa gtccgaaaag     900
gaaagacatg ttttgatttt cgatttgggt ggtggtactt tcgatgtttc cttgttgcac     960
attgctggtg gtgtttacac tgttaaatct acttccggta acactcactt gggtggtcaa    1020
gatttcgaca ccaacttgtt ggaacacttc aaggctgaat caagaagaa gactggtttg    1080
gacatctccg acgatgccag agcttttgaga agattgagaa ctgctgctga aagagctaag    1140
agaaccttat cttctgtcac tcaaactacc gttgaagttg actctttgtt tgacggtgaa    1200
gatttcgaat cctcttttgac tagagctaga tttgaagact gaacgccgc attgttcaag    1260
tctactttgg aacctgttga acaagttttg aaggatgcta agatctctaa gtctcaaatc    1320
gacgaagttg tcttggttgg tggttccacc agaattccaa aggtccaaaa gttgttgtct    1380
gacttctttg acggtaagca attggaaaaa tctattaacc cagatgaagc tgttgcttac    1440
ggtgctgctg ttcaaggtgc tatcttgacc ggccaatcca catctgacga accaaggac    1500
ttgttgttgt tagatgttgc tccattatct ctaggtgttg gtatgcaagg tgacatgttc    1560
ggtatcgttg ttccaagaaa cactactgtt ccaaccatca agagaagaac ctttactaca    1620
tgtgctgaca accaaaccac cgttcaattc ccagtctacc aaggtgaacg tgttaactgt    1680
aaagaaaaca ctttgttggg tgaattcgac ttgaagaaca tcccaatgat gccagctggt    1740
gaaccagtct tggaagctat cttcgaagtt gatgctaacg gtatcttgaa ggttactgcc    1800
gtcgaaaagt ctaccggtaa gtcttctaac atcactatct ctaacgctgt tggtagattg    1860
tcttctgaag aaattgaaaa gatggttaac caagctgaag agttcaaggc tgccgatgaa    1920
gcttttgcca agaagcacga agctagacaa agattggaat cctacgttgc ctccatcgaa    1980
caaactgtca ctgacccagt cttgtcttct aaattgaaga gaggttccaa gtccaagatt    2040
gaagctgctt tgtccgatgc tttggctgct ttgcaaatcg aagacccatc tgctgatgaa    2100
ttgagaaagg ctgaagttgg tttgaagaga gttgtcacca aggccatgtc ttctcgttaa    2160
ggcgcgcctt tgtttaactt taagaaggag agctcaatat gtctcaatcc gtagaatcac    2220
ggactcgaat caaaaacgaa cgttacgaat caggtgttat cccttacgca aaaatgggat    2280
```

```
actgggatgc tgattacgtt atcaaagata ctgacgtact tgcaatgttc cgtatgacac    2340
ctcaaaaagg tgttgaccca gttgaatgtg cagccgcaat cgcaggtgaa tcttcaacag    2400
caacttggac agttgtatgg acagaccttc taacagcatg tgatctttac cgtgcaaaag    2460
cataccgtgt tgacccagtt cctggtgcaa ctgatcaata cttttgcttac atcgcatacg   2520 aattagacct atttgaagaa ggttctttag ctaacttaac agcatcaatt attggtaacg    2580
tattcggatt caaagcggta aatgctttaa gattagaaga tatgcgtctt ccaattgcat    2640
acctaaaaac tttccaaggt ccagcaactg gtgtaattgt agaacgtgaa agattagaca    2700
aatatggtcg tcctttatta ggtgcaacag ttaaaccaaa attaggtcta tctggtaaaa    2760
actatggtcg tgtagtttac gaaggtctta aaggtggtct agatttcctt aaagatgatg    2820
aaaacattaa ctctcaacca ttcatgagat ggaaagagcg tttcttattc ggtatcgaag    2880
gtgtaaaccg tgctgctgct gctgctggtg aagtaaaagg tcactacttc aacgttactg    2940
ctggtacaat ggaagatatg tatgaacgtg ctgaattctg taaagaaatc ggtagtgtaa    3000
tctgtatgat cgaccttgta atcggatata ctgctattca aagtatggcg atctgggcac    3060
gtaaaaacag tatgattctt cacttacacc gtgctggtaa ctctacatac tcacgtcaaa    3120
aaacacatgg tatgaacttc cgtgtaattt gtaagtggat gcgtatggca ggtgttgacc    3180
acatacacgc aggtacagtt gtaggtaaac tagaagggga tccttttaatg gttaaaggtt    3240 tctataacac attattagaa acacaaacag atgtaaatct tgtacaaggt cttttctttg    3300
ctcaagattg ggcagcactt aacaaatgta tgccagttgc ttcaggtggt attcactgtg    3360
gtcaaatgca ccaacttatt aactacttag gtgacgacgt agtattacaa tttggtggtg    3420
gtactattgg tcacccagat ggtatccaag ctggtgctac tgcaaaccgt gtagcacttg    3480
aatgtatggt tgtagcacgt aacgaaggtc gtgactatgt aacagagggt cctcaaattc    3540
ttcgtaatgc agctaagagc tgtggacctc ttcaaacagc attagattta tggaaagaca    3600
ttactttcaa ctatgcttct actgatacag ctgacttcgt agaaactgca acagctaaca    3660
agtaatttgt ttaactttaa gaaggagatg ctagcatgac gaaaacgcgc tcgaacatgg    3720
cgcgctacgg caccagcctg gccatcgtgc tgggcgtgca cgtggtcgcc gtggtgctga    3780
cgctcaactg gtcggtgccc caggccatcg agctgccgcc ggcagcgatg atggtcgagt    3840
tggcgccgtt gccggagccc gcgccaccgc caccgcccaa ggccgcgccc aagccaccgg    3900
cagaggtcga ggagccgccg ctgcccaagc tggtggaggc ccccaagccg aagatcgcca    3960
tcgccaagcc gcccaagccc aaggccaagc cgcagccgcc caagcctgag aaaaagcctg    4020
agccgccgaa ggacgaacca ccggccaagg acgatgtggc ggataccccg ccaagcaacg    4080
cgcagccgca gaaatcggcc gcaccggcac cgagcatcgc ctccaacagc aatgccctgc    4140
ccagctggca gagcgacctg ctgcgccacc tggccaagta caagaagtac ccggaagacg    4200
ctcgccgtcg cggcctgcag ggcatcaacc gcctgcgctt cgtggtcgac gccgagggca    4260
aggtagtctc gtactcgctg gccggaggct cgggcagcgc ggcgctggac cgggcgaccc    4320
tggaaatgat ccgtcgcgca ggctccgtac cgaagccgcc agcggagctg ttgaacaatg    4380
gcacgatcga agtcgtggcg ccgttcgtct attccctgga ccgacgctaa gcggccgcca    4440
tcaaataaaa cgaaaggctc agtcgaaaga ctgggccttt cgttttatct gttgtttgtc    4500
ggtgaacgct ctcctgagta ggacaaatcc gccgggagcg gatttgaacg ttgcgaagca    4560
acggcccgga gggtggcggg caggacgccc gccataaact gccaggcatc aaattaagca    4620
gaaggccatc ctgacggatg gcctttttgc gtttctacaa actctaagaa accaattgtc    4680
```

```
catattgcat cagacattgc cgtcactgcg tcttttactg gctcttctcg ctaaccaaac      4740 cggtaaccccc gcttattaaa agcattctgt aacaaagcgg gaccaaagcc atgacaaaaa      4800
cgcgtaacaa aagtgtctat aatcacggca gaaaagtcca cattgattat ttgcacggcg      4860
tcacactttg ctatgccata gcattttat ccataagatt agcggatcct acctgacgct      4920
ttttatcgca actctctact gtttctccat tttgtttaac tttaagaagg agatggtacc      4980
atgactgaac ttggttctga tactttgccc tctgtgggcc agtggcaaca aattctgact      5040
gcgccacccg tctggcaggt caaggtgcag actgcatcct ggacaagtgc cgcgctggcg      5100
ctgcgcgatc agggcgggcg tttgctggga ttgtggggag aggcgggcca tgaaaatgca      5160
tttttttaca tacatgcgct gggccttggt tcaaccggat atttgtggat cactctgacg      5220
gtgcaatcca gcgagggaca atttccctcg ctggccgaca ttttcccgc tgcctcgcgg      5280 atggagcggg ccctgtacga tcttacggga atcagggcgg cggggaatgc cgatacccgg      5340
ccatggctcc gccatcagtg ctggccagcg gggattttc cactgcggga gggacaactg      5400
gatggcagtt ccttcggcgt ggatggtgat gccgattatc cttttcaatt aatcgatagc      5460
gtggatgtcc accagattcc agtgggaccg gtacacgcgg gcaccattga gcccggacac      5520
tttcgttttt cgtgtgtcgg tgaacaaatt ctgcgtctgg aagaacgatt gggatacacc      5580
cacaagggcg tcgaacgcct tttccaagat cgggatgtgt ttgcgggtgc gcgtctggca      5640
ggacgcatca gtggtgacac tacagcgggt tatgcctggg cctacagcat ggcggtggaa      5700
tccattgccc gatgcgaaat cccgcctcgt gcagccgctt tgcgtgctgt ttgcctggaa      5760
cgggagcgca tggccaacca tctgggtgat cttgccgctc tggggaatga cgctggcttc      5820
gccttctgtc agtcacaatt cctgttcatc aaggaaagcc tgctgcgcga aaaccaggaa      5880
attttcggac accgctattt gatggactgc attattcccg gtggtgtagc ttttgatctg      5940
aactccgcgc aaacagccgc gattcagcgt aacagtgaat cctggcagcg caccgtgcag      6000
cgtttggacc tcctcttgca ggagcactcc ggtctgcggg atcgtctggt gggtacagga      6060
aaaattgtgc caccccgtgc tgcagcactc ggtatggcgg ggcttgccgg ccgcgccagt      6120
ggtcaggcct gggatttgcg ggtccagttt ccccatgcac cttatcagaa tctggatgtt      6180
tccatgcagc tttccccgga aggtgacgtg gccgcacgct ggcaattgcg ctttcgggaa      6240
ttctatgagt ctctgcgtct gcagacccag ttgctgttgg atctacccag tggagatgtc      6300
agcgcaacca ttccggaaag catccccgat ggcgaaggct gggcattgt cgaagcatgg      6360 cgcggcgagg tctttgtcgc cctatctgtg gaaaacgccc gtattaaacg ctgccatccc      6420
cacgatccct cgtggaccct ctggccggtc cttgaggagg ccgtgctgaa cgatattgtt      6480
gccgactttc cgctgatcaa taaatcgttc aatttgagtt acagcggaca tgatttatga      6540
tttgtttaac tttaagaagg agatctcgag atgtcgactc ctgacaatca cggcaagaaa      6600 gccccctcaat ttgctgcgtt caaaccgcta accacggtac agaacgccaa cgactgttgc      6660
tgcgacggcg catgttccag cacgccaact ctctctgaaa acgtctccgg caccgctat      6720 agctggaaag tcagcggcat ggactgcgcc gcctgtgcgc gcaaggtaga aaatgccgtg      6780
cgccagcttg caggcgtgaa tcaggtcag gtgttgttcg ccaccgaaaa actggtggtc      6840
gatgccgaca atgacattcg tgcacaagtt gaatctgcgc tgcaaaaagc aggctattcc      6900
ctgcgcgatg aacaggccgc cgaagaaccg caagcatcac gcctgaaaga gaatctgccg      6960
ctgattacgc taatcgtgat gatggcaatc agctggggtc tggagcagtt caatcatccg      7020
```

```
ttcgggcaac tggcgtttat cgcgaccacg ctggttgggc tgtacccgat tgctcgtcag    7080
gcattacggt tgatcaaatc cggcagctac ttcgccattg aaaccttaat gagcgtagcc    7140
gctattggtg cactgtttat tggcgcaacg gctgaagctg cgatggtgtt gctgctgttt    7200
ttgattggtg aacgactgga aggctgggcc gccagccgcg cgcgtcaggg cgttagcgcg    7260
ttaatggcgc tgaaaccaga aaccgccacg cgcctgcgta agggtgagcg ggaagaggtg    7320
gcgattaaca gcctgcgccc tggcgatgtg attgaagtcg ccgcaggtgg gcgtttgcct    7380
gccgacggta aactgctctc accgtttgcc agttttgatg aaagcgccct gaccggcgaa    7440
tccattccgg tggagcgcgc aacgggcgat aaagtccctg ctggtgccac cagcgtagac    7500
cgtctggtga cgttggaagt gctgtcagaa ccgggagcca gcgccattga ccggattctg    7560
aaactgatcg aagaagccga gagcgtcgc gctcccattg agcggtttat cgaccgtttc    7620
agccgtatct atacgcccgc gattatggcc gtcgctctgc tggtgacgct ggtgccaccg    7680
ctgctgtttg ccgccagctg gcaggagtgg atttataaag ggctgacgct gctgctgatt    7740
ggctgcccgt gtgcgttagt tatctcaacg cctgcgcgca ttacctccgg gctggcggcg    7800
gcagcgcgtc gtggggcgtt gattaaaggc ggagcggcgc tggaacagct gggtcgtgtt    7860
actcaggtgg cgtttgataa aaccggtacg ctgaccgtcg gtaaaccgcg cgttaccgcg    7920
attcatccgg caacgggtat tagtgaatct gaactgctga cactggcggc ggcggtcgag    7980
caaggcgcga cgcatccact ggcgcaagcc atcgtacgcg aagcacaggt tgctgaactc    8040
gccattccca ccgccgaatc acagcgggcg ctggtcgggt ctggcattga agcgcaggtt    8100
aacggtgagc gcgtattgat ttgcgctgcc gggaaacatc ccgctgatgc atttactggt    8160
ttaattaacg aactggaaag cgccgggcaa acggtagtgc tggtagtacg taacgatgac    8220
gtgcttggtg tcattgcgtt acaggatacc ctgcgcgccg atgctgcaac tgccatcagt    8280
gaactgaacg cgctgggcgt caaaggggtg atcctcaccg gcgataatcc acgcgcagcg    8340
gcggcaattg ccggggagct ggggctggag tttaaagcgg gcctgttgcc ggaagataaa    8400
gtcaaagcgg tgaccgagct gaatcaacat gcgccgctgg cgatggtcgg tgacggtatt    8460
aacgacgcgc cagcgatgaa agctgccgcc atcgggattg caatgggtag cggcacagac    8520
gtggcgctgg aaaccgccga cgcagcatta acccataacc acctgcgcgg cctggtgcaa    8580
atgattgaac tggcacgcgc cactcacgcc aatatccgcc agaacatcac tattgcgctg    8640
gggctgaaag ggatcttcct cgtcaccacg ctgttaggga tgaccgggtt gtggctggca    8700
gtgctggcag atacggggc gacggtgctg gtgacagcga atgcgttaag attgttgcgc    8760
aggagataat ttgtttaact ttaagaagga gatactagta tggtgagcaa gggcgaggag    8820
ctgttcaccg gggtggtgcc catcctggtc gagctggacg gcgacgtaaa cggccacaag    8880
ttcagcgtgt ccggcgaggg cgagggcgat gccacctacg gcaagctgac cctgaagttc    8940
atctgcacca ccggcaagct gcccgtgccc tggcccaccc tcgtgaccac cctgacctac    9000
ggcgtgcagt gcttcagccg ctaccccgac cacatgaagc agcacgactt cttcaagtcc    9060
gccatgcccg aaggctacgt ccaggagcgc accatcttct tcaaggacga cggcaactac    9120
aagacccgcg ccgaggtgaa gttcgagggc gacaccctgg tgaaccgcat cgagctgaag    9180
ggcatcgact tcaaggagga cggcaacatc ctggggcaca gctggagta caactacaac    9240 agccacaacg tctatatcat ggccgacaag cagaagaacg gcatcaaggt gaacttcaag    9300
atccgccaca acatcgagga cggcagcgtg cagctcgccg accactacca gcagaacacc    9360
cccatcggcg acggccccgt gctgctgccc gacaaccact acctgagcac ccagtccgcc    9420
```

```
ctgagcaaag accccaacga gaagcgcgat cacatggtcc tgctggagtt cgtgaccgcc   9480
gccgggatca ctctcggcat ggacgagctg tacaagtaag tttaaacaag cttggctgtt   9540
ttggcggatg agagaagatt ttcagcctga tacagattaa atcagaacgc agaagcggtc   9600
tgataaaaca gaatttgcct ggcggcagta gcgcggtggt cccacctgac cccatgccga   9660
actcagaagt gaaacgccgt agcgccgatg gtagtgtggg gtctccccat gcgagagtag   9720
ggaactgcca ggcatcaaat aaaacgaaag gctcagtcga agactgggcc tttcgttttt   9780
atctgttgtt tgtcggtgaa cgctctcctg agtaggacaa atccgccggg agcggatttg   9840
aacgttgcga agcaacggcc cggagggtgg cgggcaggac gcccgccata aactgccagg   9900
catcaaatta agcagaaggc catcctgacg gatggccttt ttgcgtttct acaaactctt   9960
ttgtttattt ttctaaatac attcaaatat gtatccgctc atgagacaat aaccctgata  10020
aatgcttcaa taatattgaa aaaggaagag tatgagtatt caacatttcc gtgtcgccct  10080
tattcccttt tttgcggcat tttgccttcc tgttttttgct cacccagaaa cgctggtgaa  10140
agtaaaagat gctgaagatc agttgggtgc acagtgggt tacatcgaac tggatctcaa  10200
cagcggtaag atccttgaga gttttcgccc cgaagaacgt tttccaatga tgagcacttt  10260
taaagttctg ctatgtggcg cggtattatc ccgtgttgac gccgggcaag agcaactcgg  10320
tcgccgcata cactattctc agaatgactt ggttgagtac tcaccagtca cagaaaagca  10380
tcttacggat ggcatgacag taagagaatt atgcagtgct gccataacca tgagtgataa  10440
cactgcggcc aacttacttc tgacaacgat cggaggaccg aaggagctaa ccgcttttt   10500 gcacaacatg gggatcatg taactcgcct tgatcgttgg gaaccggagc tgaatgaagc   10560
cataccaaac gacgagcgtg acaccacgat gcctgtagca atggcaacaa cgttgcgcaa   10620
actattaact ggcgaactac ttactctagc ttcccggcaa caattaatag actggatgga   10680
ggcggataaa gttgcaggac cacttctgcg ctcggccctt ccggctggct ggtttattgc   10740
tgataaatct ggagccggtg agcgtgggtc tcgcggtatc attgcagcac tggggccaga   10800
tggtaagccc tcccgtatcg tagttatcta cacgacgggg agtcaggcaa ctatggatga   10860
acgaaataga cagatcgctg agataggtgc ctcactgatt aagcattggt aactgtcaga   10920
ccaagtttac tcatatatac tttagattga tttaaaactt catttttaat ttaaaaggat   10980
ctaggtgaag atccttttg ataatctcat gaccaaaatc ccttaacgtg agttttcgtt   11040
ccactgagcg tcagaccccg tagaaaagat caaaggatct tcttgagatc ctttttttct   11100
gcgcgtaatc tgctgcttgc aaacaaaaaa accaccgcta ccagcggtgg tttgtttgcc   11160
ggatcaagag ctaccaactc tttttccgaa ggtaactggc ttcagcagag cgcagatacc   11220
aaatactgtc cttctagtgt agccgtagtt aggccaccac ttcaagaact ctgtagcacc   11280
gcctacatac ctcgctctgc taatcctgtt accagtggct gctgccagtg gcgataagtc   11340
gtgtcttacc gggttggact caagacgata gttaccggat aaggcgcagc ggtcgggctg   11400
aacggggggt tcgtgcacac agcccagctt ggagcgaacg acctacaccg aactgagata   11460
cctacagcgt gagctatgag aaagcgccac gcttcccgaa gggagaaagg cggacaggta   11520
tccggtaagc ggcagggtcg aacaggaga gcgcacgagg gagcttccag ggggaaacgc   11580
ctggtatctt tatagtcctg tcgggtttcg ccacctctga cttgagcgtc gatttttgtg   11640
atgctcgtca gggggggcgga gcctatggaa aaacgccagc aacgcggcct ttttacggtt   11700
cctggccttt tgctggcctt ttgctcacat gttctttcct gcgttatccc ctgattctgt   11760
```

| | | | |
|---|---|---|---|
| ggataaccgt | attaccgcct | tgagtgagc tgataccgct | cgccgcagcc gaacgaccga | 11820 |
| gcgcagcgag | tcagtgagcg | aggaagcgga agagcgcctg | atgcggtatt ttctccttac | 11880 |
| gcatctgtgc | ggtatttcac | accgcatatg gtgcactctc | agtacaatct gctctgatgc | 11940 |
| cgcatagtta | agccagtata | cactccgcta tcgctacgtg | actgggtcat ggctgcgccc | 12000 |
| cgacacccgc | caacacccgc | tgacgcgccc tgacgggctt | gtctgctccc ggcatccgct | 12060 |
| tacagacaag | ctgtgaccgt | ctccgggagc tgcatgtgtc | agaggttttc accgtcatca | 12120 |
| ccgaaacgcg | cgaggcagca | gatcaattcg cgcgcgaagg | cgaagcggca tgcataatgt | 12180 |
| gcctgtcaaa | tggacgaagc | agggattctg caaaccctat | gctactccgt caagccgtca | 12240 |
| attgtctgat | tcgttaccaa | ttatgacaac ttgacggcta | catcattcac tttttcttca | 12300 |
| caaccggcac | ggaactcgct | cgggctggcc ccggtgcatt | ttttaaatac ccgcgagaaa | 12360 |
| tagagttgat | cgtcaaaacc | aacattgcga ccgacggtgg | cgataggcat ccgggtggtg | 12420 |
| ctcaaaagca | gcttcgcctg | gctgatacgt tggtcctcgc | gccagcttaa gacgctaatc | 12480 |
| cctaactgct | ggcggaaaag | atgtgacaga cgcgacggcg | acaagcaaac atgctgtgcg | 12540 |
| acgctggcga | tatcaaaatt | gctgtctgcc aggtgatcgc | tgatgtactg acaagcctcg | 12600 |
| cgtacccgat | tatccatcgg | tggatggagc gactcgttaa | tcgcttccat gcgccgcagt | 12660 |
| aacaattgct | caagcagatt | tatcgccagc agctccgaat | agcgcccttc cccttgcccg | 12720 |
| gcgttaatga | tttgcccaaa | caggtcgctg aaatgcggct | ggtgcgcttc atccgggcga | 12780 |
| aagaaccccg | tattggcaaa | tattgacggc cagttaagcc | attcatgcca gtaggcgcgc | 12840 |
| ggacgaaagt | aaacccactg | gtgataccat tcgcgagcct | ccggatgacg accgtagtga | 12900 |
| tgaatctctc | ctggcgggaa | cagcaaaata tcacccggtc | ggcaaacaaa ttctcgtccc | 12960 |
| tgattttttca | ccaccccctg | accgcgaatg gtgagattga | gaatataacc tttcattccc | 13020 |
| agcggtcggt | cgataaaaaa | atcgagataa ccgttggcct | caatcggcgt taaacccgcc | 13080 |
| accagatggg | cattaaacga | gtatcccggc agcaggggat | cattttgcgc ttcagccata | 13140 |
| cttttcatac | tcccgccatt | cagag | | 13165 |

<210> SEQ ID NO 8
<211> LENGTH: 17840
<212> TYPE: DNA
<213> ORGANISM: Artificial Sequence
<220> FEATURE:
<223> OTHER INFORMATION: Synthetic Construct

<400> SEQUENCE: 8

| | | | |
|---|---|---|---|
| acggattaga | agccgccgag | cgggtgacag ccctccgaag | gaagactctc ctccgtgcgt | 60 |
| cctcgtcttc | accggtcgcg | ttcctgaaac gcagatgtgc | ctcgcgccgc actgctccga | 120 |
| acaataaaga | ttctacaata | ctagctttta tggttatgaa | gaggaaaaat tggcagtaac | 180 |
| ctggccccac | aaaccttcaa | atgaacgaat caaattaaca | accataggat gataatgcga | 240 |
| ttagtttttt | agccttattt | ctggggtaat taatcagcga | agcgatgatt tttgatctat | 300 |
| taacagatat | ataaatgcaa | aaactgcata accactttaa | ctaatacttt caacattttc | 360 |
| ggtttgtatt | acttcttatt | caaatgtaat aaaagtatca | acaaaaaatt gttaatatac | 420 |
| ctctatactt | taacgtcaag | gagaaaaaac cccggatcgg | actactagca gctgtaatac | 480 |
| gactcactat | agggaatatt | aagcttccta gggccaccat | gactgaactt ggttctgata | 540 |
| cttttgccctc | tgtgggccag | tgcaacaaa ttctgactgc | gccacccgtc tggcaggtca | 600 |
| aggtgcagac | tgcatcctgg | acaagtgccg cgctggcgct | gcgcgatcag ggcgggcgtt | 660 |

```
tgctgggatt gtggggagag gcgggccatg aaaatgcatt tttttacata catgcgctgg    720
gccttggttc aaccggatat ttgtggatca ctctgacggt gcaatccagc gagggacaat    780
ttccctcgct ggccgacatt tttcccgctg cctcgcggat ggagcgggcc ctgtacgatc    840
ttacgggaat cagggcggcg gggaatgccg atacccggcc atggctccgc catcagtgct    900
ggccagcggg gattttttcca ctgcgggagg acaactgga tggcagttcc ttcggcgtgg   960
atggtgatgc cgattatcct tttcaattaa tcgatagcgt ggatgtccac cagattccag    1020
tgggaccggt acacgcgggc accattgagc ccggacactt tcgttttttcg tgtgtcggtg   1080 aacaaattct gcgtctggaa gaacgattgg gatacaccca caagggcgtc gaacgccttt    1140
tccaagatcg ggatgtgttt gcgggtgcgc gtctggcagg acgcatcagt ggtgacacta    1200
cagcgggtta tgcctgggcc tacagcatgg cggtggaatc cattgcccga tgcgaaatcc    1260
cgcctcgtgc agccgcttttg cgtgctgttt gcctggaacg ggagcgcatg gccaaccatc    1320
tgggtgatct tgccgctctg gggaatgacg ctggcttcgc cttctgtcag tcacaattcc    1380
tgttcatcaa ggaaagcctg ctgcgcgaaa accaggaaat tttcggacac cgctatttga   1440
tggactgcat tattcccggt ggtgtagctt ttgatctgaa ctccgcgcaa acagccgcga    1500
ttcagcgtaa cagtgaatcc tggcagcgca ccgtgcagcg tttggacctc ctcttgcagg    1560
agcactccgg tctgcgggat cgtctggtgg gtacaggaaa aattgtgcca ccccgtgctg    1620
cagcactcgg tatggcgggg cttgccggcc gcgccagtgg tcaggcctgg gatttgcggg    1680
tccagtttcc ccatgcacct tatcagaatc tggatgtttc catgcagctt tccccggaag    1740
gtgacgtggc cgcacgctgg caattgcgct tcgggaatt ctatgagtct ctgcgtctgc     1800
agacccagtt gctgttggat ctacccagtg gagatgtcag cgcaaccatt ccggaaagca    1860
tccccgatgg cgaaggcttg ggcattgtcg aagcatggcg cggcgaggtc tttgtcgccc    1920
tatctgtgga aaacgcccgt attaaacgct gccatcccca cgatccctcg tggaccctct    1980
ggccggtcct tgaggaggcc gtgctgaacg atattgttgc cgactttccg ctgatcaata    2040
aatcgttcaa tttgagttac agcggacatg atttataatt aattaatcat gtaattagtt    2100
atgtcacgct tacattcacg ccctcccccc acatccgctc taaccgaaaa ggaaggagtt    2160
agacaacctg aagtctaggt ccctatttat ttttttatag ttatgttagt attaagaacg    2220
ttatttatat ttcaaatttt tctttttttt ctgtacagac gcgtgtacgc atgtaacatt    2280
atactgaaaa ccttgcttga gaaggttttg ggacgctcga aggctttaat ttgccggatt    2340
agaagccgcc gagcgggtga cagccctccg aaggaagact ctcctccgtg cgtcctcgtc    2400
ttcaccggtc gcgttcctga aacgcagatg tgcctcgcgc cgcactgctc cgaacaataa    2460
agattctaca atactagctt ttatggttat gaagaggaaa aattggcagt aacctggccc    2520
cacaaacctt caaatgaacg aatcaaatta caaccatag gatgataatg cgattagttt     2580
tttagcctta tttctgggt aattaatcag cgaagcgatg attttttgatc tattaacaga    2640 tatataaatg caaaaactgc ataaccactt taactaatac tttcaacatt tcggtttgt     2700 attacttctt attcaaatgt aataaaagta tcaacaaaaa attgttaata tacctctata    2760
ctttaacgtc aaggagggcg cgccaccatg tcgactcctg acaatcacgg caagaaagcc    2820
cctcaatttg ctgcgttcaa accgctaacc acggtacaga acgccaacga ctgttgctgc    2880
gacggcgcat gttccagcac gccaactctc tctgaaaacg tctccggcac ccgctatagc    2940
tggaaagtca gcggcatgga ctgcgccgcc tgtgcgcgca aggtagaaaa tgccgtgcgc    3000
```

```
cagcttgcag gcgtgaatca ggtgcaggtg ttgttcgcca ccgaaaaact ggtggtcgat      3060
gccgacaatg acattcgtgc acaagttgaa tctgcgctgc aaaaagcagg ctattccctg      3120
cgcgatgaac aggccgccga agaaccgcaa gcatcacgcc tgaaagagaa tctgccgctg      3180
attacgctaa tcgtgatgat ggcaatcagc tggggtctgg agcagttcaa tcatccgttc      3240
gggcaactgg cgtttatcgc gaccacgctg gttgggctgt acccgattgc tcgtcaggca      3300
ttacggttga tcaaatccgg cagctacttc gccattgaaa ccttaatgag cgtagccgct      3360
attggtgcac tgtttattgg cgcaacggct gaagctgcga tggtgttgct gctgtttttg      3420
attggtgaac gactggaagg ctgggccgcc agccgcgcgc gtcagggcgt tagcgcgtta      3480
atggcgctga aaccagaaac cgccacgcgc ctgcgtaagg gtgagcggga agaggtggcg      3540
attaacagcc tgcgccctgg cgatgtgatt gaagtcgccg caggtgggcg tttgcctgcc      3600
gacggtaaac tgctctcacc gtttgccagt tttgatgaaa gcgccctgac cggcgaatcc      3660
attccggtgg agcgcgcaac gggcgataaa gtccctgctg gtgccaccag cgtagaccgt      3720
ctggtgacgt tggaagtgct gtcagaaccg ggagccagcg ccattgaccg gattctgaaa      3780
ctgatcgaag aagccgaaga gcgtcgcgct cccattgagc ggtttatcga ccgtttcagc      3840
cgtatctata cgcccgcgat tatggccgtc gctctgctgg tgacgctggt gccaccgctg      3900
ctgtttgccg ccagctggca ggagtggatt tataaagggc tgacgctgct gctgattggc      3960
tgcccgtgtg cgttagttat ctcaacgcct gcggcgatta cctccgggct ggcggcggca      4020
gcgcgtcgtg gggcgttgat taaaggcgga gcggcgctgg aacagctggg tcgtgttact      4080
caggtggcgt ttgataaaac cggtacgctg accgtcggta accgcgcgt taccgcgatt      4140 catccggcaa cgggtattag tgaatctgaa ctgctgacac tggcggcggc ggtcgagcaa      4200
ggcgcgacgc atccactggc gcaagccatc gtacgcgaag cacaggttgc tgaactcgcc      4260
attcccaccg ccgaatcaca gcgggcgctg gtcgggtctg gcattgaagc gcaggttaac      4320
ggtgagcgcg tattgatttg cgctgccggg aaacatcccg ctgatgcatt tactggttta      4380
attaacgaac tggaaagcgc cgggcaaacg gtagtgctgg tagtacgtaa cgatgacgtg      4440
cttggtgtca ttgcgttaca ggataccctg cgcgccgatg ctgcaactgc catcagtgaa      4500
ctgaacgcgc tgggcgtcaa aggggtgatc ctcaccggcg ataatccacg cgcagcggcg      4560
gcaattgccg gggagctggg gctggagttt aaagcgggcc tgttgccgga agataaagtc      4620
aaagcggtga ccgagctgaa tcaacatgcg ccgctggcga tggtcggtga cggtattaac      4680
gacgcgccag cgatgaaagc tgccgccatc gggattgcaa tgggtagcgg cacagacgtg      4740
gcgctggaaa ccgccgacgc agcattaacc cataaccacc tgcgcggcct ggtgcaaatg      4800
attgaactgg cacgcgccac tcacgccaat atccgccaga acatcactat tgcgctgggg      4860
ctgaaaggga tcttcctcgt caccacgctg ttagggatga ccgggttgtg gctggcagtg      4920
ctggcagata cgggggcgac ggtgctggtg acagcgaatg cgttaagatt gttgcgcagg      4980
agataataac ttaagtcatg taattagtta tgtcacgctt acattcacgc cctcccccca      5040
catccgctct aaccgaaaag gaaggagtta gacaacctga agtctaggtc cctatttatt      5100
tttttatagt tatgttagta ttaagaacgt tatttatatt tcaaattttt ctttttttc      5160 tgtacagacg cgtgtacgca tgtaacatta tactgaaaac cttgcttgag aaggttttgg      5220
gacgctcgaa ggctttaatt tgccggatta gaagccgccg agcgggtgac agccctccga      5280
aggaagactc tcctccgtgc gtcctcgtct tcaccggtcg cgttcctgaa acgcagatgt      5340
gcctcgcgcc gcactgctcc gaacaataaa gattctacaa tactagcttt tatggttatg      5400
```

```
aagaggaaaa attggcagta acctggcccc acaaaccttc aaatgaacga atcaaattaa    5460
caaccatagg atgataatgc gattagtttt ttagccttat ttctggggta attaatcagc    5520
gaagcgatga ttttgatct attaacagat atataaatgc aaaaactgca taaccacttt    5580
aactaatact ttcaacattt tcggtttgta ttacttctta ttcaaatgta ataaaagtat    5640
caacaaaaaa ttgttaatat acctctatac tttaacgtca aggaggaatt catgacgaaa    5700
acgcgctcga acatggcgcg ctacggcacc agcctggcca tcgtgctggg cgtgcacgtg    5760
gtcgccgtgg tgctgacgct caactggtcg gtgccccagg ccatcgagct gccgccggca    5820
gcgatgatga tcgagttggc gccgttgccg agcccgcgc caccgccacc gcccaaggcc    5880
gcgcccaagc caccggcaga ggtcgaggag ccgccgctgc ccaagctggt ggaggccccc    5940
aagccgaaga tcgccatcgc caagccgccc aagcccaagg ccaagccgca gccgcccaag    6000
cctgagaaaa agcctgagcc gccgaaggac gaaccaccgg ccaaggacga tgtggcggat    6060
accccgccaa gcaacgcgca gccgcagaaa tcggccgcac cggcaccgag catcgcctcc    6120
aacagcaatg ccctgcccag ctggcagagc gacctgctgc gccacctggc caagtacaag    6180
aagtacccgg aagacgctcg ccgtcgcggc ctgcagggca tcaaccgcct gcgcttcgtg    6240
gtcgacgccg agggcaaggt agtctcgtac tcgctggccg gaggctcggg cagcgcggcg    6300
ctggaccggg cgaccctgga aatgatccgt cgcgcaggct ccgtaccgaa gccgccagcg    6360
gagctgttga acaatggcac gatcgaagtc gtggcgccgt tcgtctattc cctggaccga    6420
cgctaagttt aaactcatgt aattagttat gtcacgctta cattcacgcc ctccccccac    6480
atccgctcta accgaaaagg aaggagttag acaacctgaa gtctaggtcc ctatttattt    6540
ttttatagtt atgttagtat taagaacgtt atttatattt caaattttc tttttttct    6600
gtacagacgc gtgtacgcat gtaacattat actgaaaacc ttgcttgaga aggttttggg    6660
acgctcgaag gctttaattt gccggattag aagccgccga gcgggtgaca gccctccgaa    6720
ggaagactct cctccgtgcg tcctcgtctt caccggtcgc gttcctgaaa cgcagatgtg    6780
cctcgcgccg cactgctccg aacaataaag attctacaat actagctttt atggttatga    6840
agaggaaaaa ttggcagtaa cctggcccca caaaccttca aatgaacgaa tcaaattaac    6900
aaccatagga tgataatgcg attagttttt tagccttatt tctggggtaa ttaatcagcg    6960
aagcgatgat ttttgatcta ttaacagata tataaatgca aaaactgcat aaccactttta    7020
actaatactt tcaacatttt cggtttgtat tacttcttat tcaaatgtaa taaaagtatc    7080
aacaaaaaat tgttaatata cctctatact ttaacgtcaa ggaggagctc accatggctg    7140
aaggtgtttt ccaaggtgct atcggtatcg atttaggtac aacctactct tgtgttgcta    7200
cttacgaatc ctccgttgaa attattgcca acgaacaagg taacagagtc accccatctt    7260
tcgttgcttt cactccagaa gaaagattga ttggtgatgc tgccaagaac caagctgctt    7320
tgaacccaag aaacactgtc ttcgatgcta agcgtttgat tggtagaaga ttcgacgacg    7380
aatctgttca aaaggacatg aagacctggc cttttcaaggt tatcgacgtc gatggtaacc    7440
cagtcatcga agtccaatac ttggaagaaa ccaagacttt ctccccacaa gaaatttccg    7500
ctatggtttt gaccaagatg aaggaaattg ctgaagctaa gattggtaag aaggttgaaa    7560
aggccgtcat tactgtccca gcttacttta acgacgctca agacaagct accaaggatg    7620
ccggtgccat ttctgttttg aacgttttgc gtatcatcaa cgaacctact gccgctgcta    7680
ttgcttacgg tctaggtgct ggtaagtccg aaaaggaaag acatgttttg attttcgatt    7740
```

```
tgggtggtgg tactttcgat gtttccttgt tgcacattgc tggtggtgtt tacactgtta    7800
aatctacttc cggtaacact cacttgggtg gtcaagattt cgacaccaac ttgttggaac    7860
acttcaaggc tgaattcaag aagaagactg gtttggacat ctccgacgat gccagagctt    7920
tgagaagatt gagaactgct gctgaaagag ctaagagaac cttatcttct gtcactcaaa    7980
ctaccgttga agttgactct ttgtttgacg gtgaagattt cgaatcctct ttgactagag    8040
ctagatttga agacttgaac gccgcattgt tcaagtctac tttggaacct gttgaacaag    8100
ttttgaagga tgctaagatc tctaagtctc aaatcgacga agttgtcttg gttggtggtt    8160
ccaccagaat tccaaaggtc caaaagttgt tgtctgactt ctttgacggt aagcaattgg    8220
aaaaatctat taacccagat gaagctgttg cttacggtgc tgctgttcaa ggtgctatct    8280
tgaccggcca atccacatct gacgaaacca aggacttgtt gttgttagat gttgctccat    8340
tatctctagg tgttggtatg caaggtgaca tgttcggtat cgttgttcca agaaacacta    8400
ctgttccaac catcaagaga agaacccttta ctacatgtgc tgacaaccaa accaccgttc    8460
aattcccagt ctaccaaggt gaacgtgtta actgtaaaga aaaacactttg ttgggtgaat    8520 tcgacttgaa gaacatccca atgatgccag ctggtgaacc agtcttggaa gctatcttcg    8580
aagttgatgc taacggtatc ttgaaggtta ctgccgtcga aaagtctacc ggtaagtctt    8640
ctaacatcac tatctctaac gctgttggta gattgtcttc tgaagaaatt gaaaagatgg    8700
ttaaccaagc tgaagagttc aaggctgccg atgaagcttt tgccaagaag cacgaagcta    8760
gacaaagatt ggaatcctac gttgcctcca tcgaacaaac tgtcactgac ccagtcttgt    8820
cttctaaatt gaagagaggt tccaagtcca agattgaagc tgctttgtcc gatgctttgg    8880
ctgctttgca aatcgaagac ccatctgctg atgaattgag aaaggctgaa gttggtttga    8940
agagagttgt caccaaggcc atgtcttctc gttaaggtac ctcatgtaat tagttatgtc    9000
acgcttacat tcacgccctc cccccacatc cgctctaacc gaaaaggaag gagttagaca    9060
acctgaagtc taggtcccta tttatttttt tatagttatg ttagtattaa gaacgttatt    9120
tatatttcaa atttttcttt tttttctgta cagacgcgtg tacgcatgta acattatact    9180
gaaaaccttg cttgagaagg ttttgggacg ctcgaaggct ttaatttgcc ggattagaag    9240
ccgccgagcg ggtgacagcc ctccgaagga agactctcct ccgtgcgtcc tcgtcttcac    9300
cggtcgcgtt cctgaaacgc agatgtgcct cgcgccgcac tgctccgaac aataaagatt    9360
ctacaatact agcttttatg gttatgaaga ggaaaaattg gcagtaacct ggccccacaa    9420
accttcaaat gaacgaatca aattaacaac cataggatga taatgcgatt agttttttag    9480
ccttatttct ggggtaatta atcagcgaag cgatgatttt tgatctatta acagatatat    9540
aaatgcaaaa actgcataac cactttaact aatactttca acattttcgg tttgtattac    9600
ttcttattca aatgtaataa aagtatcaac aaaaaattgt taatatacct ctatactttta   9660 acgtcaagga gggatccgcc accatgtctc aatccgtaga atcacggact cgaatcaaaa    9720
acgaacgtta cgaatcaggt gttatcccctt acgcaaaaat gggatactgg gatgctgatt    9780
acgttatcaa agatactgac gtacttgcaa tgttccgtat gacacctcaa aaaggtgttg    9840
acccagttga atgtgcagcc gcaatcgcag gtgaatcttc aacagcaact tggacagttg    9900
tatggacaga ccttctaaca gcatgtgatc tttaccgtgc aaaagcatac cgtgttgacc    9960
cagttcctgg tgcaactgat caatactttg cttacatcgc atacgaatta gacctatttg    10020
aagaaggttc tttagctaac ttaacagcat caattattgg taacgtattc ggattcaaag    10080
cggtaaatgc tttaagatta gaagatatgc gtcttccaat tgcatacctt aaaactttcc    10140
```

```
aaggtccagc aactggtgta attgtagaac gtgaaagatt agacaaatat ggtcgtcctt    10200
tattaggtgc aacagttaaa ccaaaattag gtctatctgg taaaaactat ggtcgtgtag    10260
tttacgaagg tcttaaaggt ggtctagatt tccttaaaga tgatgaaaac attaactctc    10320
aaccattcat gagatggaaa gagcgtttct tattcggtat cgaaggtgta aaccgtgctg    10380
ctgctgctgc tggtgaagta aaaggtcact acttcaacgt tactgctggt acaatggaag    10440
atatgtatga acgtgctgaa ttctgtaaag aaatcggtag tgtaatctgt atgatcgacc    10500
ttgtaatcgg atatactgct attcaaagta tggcgatctg ggcacgtaaa aacagtatga    10560 ttcttcacttacaccgtgct ggtaactcta catactcacg tcaaaaaaca catggtatga    10620
acttccgtgt aatttgtaag tggatgcgta tggcaggtgt tgaccacata cacgcaggta    10680
cagttgtagg taaactagaa ggggatcctt taatggttaa aggtttctat aacacattat    10740
tagaaacaca aacagatgta aatcttgtac aaggtctttt ctttgctcaa gattgggcag    10800
cacttaacaa atgtatgcca gttgcttcag gtggtattca ctgtggtcaa atgcaccaac    10860
ttattaacta cttaggtgac gacgtagtat tacaatttgg tggtggtact attggtcacc    10920
cagatggtat ccaagctggt gctactgcaa accgtgtagc acttgaatgt atggttgtag    10980
cacgtaacga aggtcgtgac tatgtaacag agggtcctca aattcttcgt aatgcagcta    11040
agagctgtgg aacctcttca acagcattag atttatggaa agacattact ttcaactatg    11100
cttctactga tacagctgac ttcgtagaaa ctgcaacagc taacaagtaa gaattctcat    11160
gtaattagtt atgtcacgct tacattcacg ccctccccccacatccgctc taaccgaaaa    11220 ggaaggagtt agacaacctg aagtctaggt ccctatttat tttttttatag ttatgttagt    11280 attaagaacg ttatttatat ttcaaatttt tcttttttttt ctgtacagac gcgtgtacgc    11340
atgtaacatt atactgaaaa ccttgcttga gaaggttttg ggacgctcga aggctttaat    11400
ttgccggatt agaagccgcc gagcgggtga cagccctccg aaggaagact ctcctccgtg    11460
cgtcctcgtc ttcaccggtc gcgttcctga acgcagatg tgcctcgcgc cgcactgctc    11520
cgaacaataa agattctaca atactagctt ttatggttat gaagaggaaa aattggcagt    11580
aacctggccc cacaaacctt caaatgaacg aatcaaatta acaaccatag gatgataatg    11640
cgattagttt tttagcctta tttctggggt aattaatcag cgaagcgatg attttttgatc    11700 tattaacaga tatataaatg caaaaactgc ataaccactt taactaatac tttcaacatt    11760 ttcggttttgt attacttctt attcaaatgt aataaaagta tcaacaaaaa attgttaata    11820
tacctctata ctttaacgtc aaggaggcgg ccgccaccat ggtgagcaag ggcgaggagc    11880
tgttcaccgg ggtggtgccc atcctggtcg agctggacgg cgacgtaaac ggccacaagt    11940
tcagcgtgtc cggcgagggc gagggcgatg ccacctacgg caagctgacc ctgaagttca    12000
tctgcaccac cggcaagctg cccgtgccct ggcccaccct cgtgaccacc ctgacctacg    12060
gcgtgcagtg cttcagccgc taccccgacc acatgaagca gcacgacttc ttcaagtccg    12120
ccatgcccga aggctacgtc caggagcgca ccatcttctt caaggacgac ggcaactaca    12180
agacccgcgc cgaggtgaag ttcgagggcg acaccctggt gaaccgcatc gagctgaagg    12240
gcatcgactt caaggaggac ggcaacatcc tggggcacaa gctggagtac aactacaaca    12300
gccacaacgt ctatatcatg gccgacaagc agaagaacgg catcaaggtg aacttcaaga    12360
tccgccacaa catcgaggac ggcagcgtgc agctcgccga ccactaccag cagaacaccc    12420
ccatcggcga cggccccgtg ctgctgcccg acaaccacta cctgagcacc cagtccgccc    12480
```

```
tgagcaaaga ccccaacgag aagcgcgatc acatggtcct gctggagttc gtgaccgccg   12540
ccgggatcac tctcggcatg gacgagctgt acaagtaatc tagagggccg catcatgtaa   12600
ttagttatgt cacgcttaca ttcacgccct cccccacat  ccgctctaac cgaaaaggaa   12660
ggagttagac aacctgaagt ctaggtccct atttatttttt ttatagttat gttagtatta   12720
agaacgttat ttatatttca aattttttctt tttttctgt  acagacgcgt gtacgcatgt   12780
aacattatac tgaaaacctt gcttgagaag gttttgggac gctcgaaggc tttaatttgc   12840
ggccctgcat taatgaatcg gccaacgcgc ggggagaggc ggtttgcgta ttgggcgctc   12900
ttccgcttcc tcgctcactg actcgctgcg ctcggtcgtt cggctgcggc gagcggtatc   12960
agctcactca aaggcggtaa tacggttatc cacagaatca ggggataacg caggaaagaa   13020
catgtgagca aaaggccagc aaaagcccag gaaccgtaaa aaggccgcgt tgctggcgtt   13080
tttccatagg ctccgccccc ctgacgagca tcacaaaaat cgacgctcaa gtcagaggtg   13140
gcgaaacccg acaggactat aaagatacca ggcgtttccc cctggaagct ccctcgtgcg   13200
ctctcctgtt ccgaccctgc cgcttaccgg atacctgtcc gcctttctcc cttcgggaag   13260
cgtggcgctt tctcatagct cacgctgtag gtatctcagt tcggtgtagg tcgttcgctc   13320
caagctgggc tgtgtgcacg aaccccccgt tcagcccgac cgctgcgcct tatccggtaa   13380
ctatcgtctt gagtccaacc cggtaagaca cgacttatcg ccactggcag cagccactgg   13440
taacaggatt agcagagcga ggtatgtagg cggtgctaca gagttcttga agtggtggcc   13500
taactacggc tacactagaa ggacagtatt tggtatctgc gctctgctga agccagttac   13560
cttcggaaaa agagttggta gctcttgatc cggcaaacaa accaccgctg gtagcggtgg   13620
tttttttgtt tgcaagcagc agattacgcg cagaaaaaaa ggatctcaag aagatccttt   13680
gatcttttct acggggtctg acgctcagtg gaacgaaaac tcacgttaag ggattttggt   13740
catgagatta tcaaaaagga tcttcaccta gatcctttta aattaaaaat gaagttttaa   13800
atcaatctaa agtatatatg agtaaacttg gtctgacagt taccaatgct taatcagtga   13860
ggcacctatc tcagcgatct gtctatttcg ttcatccata gttgcctgac tccccgtcgt   13920
gtagataact acgatacggg agcgcttacc atctggcccc agtgctgcaa tgataccgcg   13980
agacccacgc tcaccggctc cagatttatc agcaataaac cagccagccg aagggccga   14040 gcgcagaagt ggtcctgcaa ctttatccgc ctccatccag tctattaatt gttgccggga   14100
agctagagta agtagttcgc cagttaatag tttgcgcaac gttgttggca ttgctacagg   14160
catcgtggtg tcactctcgt cgtttggtat ggcttcattc agctccggtt cccaacgatc   14220
aaggcgagtt acatgatccc ccatgttgtg caaaaaagcg gttagctcct tcggtcctcc   14280
gatcgttgtc agaagtaagt tggccgcagt gttatcactc atggttatgg cagcactgca   14340
taattctctt actgtcatgc catccgtaag atgcttttct gtgactggtg agtactcaac   14400
caagtcattc tgagaatagt gtatgcggcg accgagttgc tcttgcccgg cgtcaatacg   14460
ggataatagt gtatcacata gcagaacttt aaaagtgctc atcattggaa acgttcttc   14520 ggggcgaaaa ctctcaagga tcttaccgct gttgagatcc agttcgatgt aacccactcg   14580
tgcacccaac tgatcttcag catcttttac tttcaccagc gtttctgggt gagcaaaaac   14640
aggaaggcaa aatgccgcaa aaaagggaat aagggcgaca cggaaatgtt gaatactcat   14700
actcttcctt tttcaatggg taataactga tataattaaa ttgaagctct aatttgtgag   14760
tttagtatac atgcatttac ttataataca gttttttagt tttgctggcc gcatcttctc   14820
aaatatgctt cccagcctgc ttttctgtaa cgttcaccct ctaccttagc atcccttccc   14880
```

```
tttgcaaata gtcctcttcc aacaataata atgtcagatc ctgtagagac cacatcatcc   14940
acggttctat actgttgacc caatgcgtct cccttgtcat ctaaacccac accgggtgtc   15000
ataatcaacc aatcgtaacc ttcatctctt ccacccatgt ctctttgagc aataaagccg   15060
ataacaaaat ctttgtcgct cttcgcaatg tcaacagtac ccttagtata ttctccagta   15120
gatagggagc ccttgcatga caattctgct aacatcaaaa ggcctctagg ttcctttgtt   15180
acttcttctg ccgcctgctt caaaccgcta acaatacctg gcccaccac accgtgtgca    15240 ttcgtaatgt ctgcccattc tgctattctg tatacacccg cagagtactg caatttgact   15300
gtattaccaa tgtcagcaaa ttttctgtct tcgaagagta aaaaattgta cttggcggat   15360
aatgccttta gcggcttaac tgtgccctcc atggaaaaat cagtcaagat atccacatgt   15420 gttttagta aacaaatttt gggacctaat gcttcaacta actccagtaa ttccttggtg    15480
gtacgaacat ccaatgaagc acacaagttt gtttgctttt cgtgcatgat attaaatagc   15540
ttggcagcaa caggactagg atgagtagca gcacgttcct tatatgtagc tttcgacatg   15600
atttatcttc gtttcctgca ggttttttgtt ctgtgcagtt gggttaagaa tactgggcaa   15660
tttcatgttt cttcaacact acatatgcgt atatatacca atctaagtct gtgctccttc   15720
cttcgttctt ccttctgttc ggagattacc gaatcaaaaa aatttcaaag aaaccgaaat   15780 caaaaaaag aataaaaaaa aaatgatgaa ttgaattgaa aagctagctt atcgatgata    15840
agctgtcaaa gatgagaatt aattccacgg actatagact atactagata ctccgtctac   15900
tgtacgatac acttccgctc aggtccttgt cctttaacga ggccttacca ctcttttgtt   15960
actctattga tccagctcag caaaggcagt gtgatctaag attctatctt cgcgatgtag   16020
taaaactagc tagaccgaga aagagactag aaatgcaaaa ggcacttcta caatggctgc   16080
catcattatt atccgatgtg acgctgcagc ttctcaatga tattcgaata cgctttgagg   16140
agatacagcc taatatccga caaactgttt tacagattta cgatcgtact tgttacccat   16200
cattgaattt tgaacatccg aacctgggag ttttccctga aacagatagt atatttgaac   16260
ctgtataata atatatagtc tagcgcttta cggaagacaa tgtatgtatt tcggttcctg   16320
gagaaactat tgcatctatt gcataggtaa tcttgcacgt cgcatccccg gttcattttc   16380
tgcgtttcca tcttgcactt caatagcata tctttgttaa cgaagcatct gtgcttcatt   16440
ttgtagaaca aaaatgcaac gcgagagcgc taatttttca aacaaagaat ctgagctgca   16500
tttttacaga acagaaatgc aacgcgaaag cgctatttta ccaacgaaga atctgtgctt   16560 cattttgta aaacaaaaat gcaacgcgac gagagcgcta attttttcaaa caagaatct    16620 gagctgcatt tttacagaac agaaatgcaa cgcgagagcg ctattttacc aacaaagaat   16680
ctatacttct tttttgttct acaaaaatgc atcccgagag cgctattttt ctaacaaagc   16740
atcttagatt actttttttc cctttgtgc gctctataat gcagtctctt gataactttt    16800
tgcactgtag gtccgttaag gttagaagaa ggctactttg gtgtctattt tctcttccat    16860
aaaaaaagcc tgactccact tcccgcgttt actgattact agcgaagctg cgggtgcatt   16920
ttttcaagat aaaggcatcc ccgattatat tctataccga tgtggattgc gcatactttg    16980
tgaacagaaa gtgatagcgt tgatgattct tcattggtca gaaaattatg aacggtttct    17040 tctatttttgt ctctatatac tacgtatagg aaatgtttac attttcgtat tgttttcgat   17100
tcactctatg aatagttctt actacaattt ttttgtctaa agagtaatac tagagataaa   17160
cataaaaaat gtagaggtcg agtttagatg caagttcaag gagcgaaagg tggatgggta   17220
```

| ggttatatag ggatatagca cagagatata tagcaaagag atactttga gcaatgtttg | 17280 |
| tggaagcggt attcgcaatg ggaagctcca ccccggttga taatcagaaa agccccaaaa | 17340 |
| acaggaagat tgtataagca aatatttaaa ttgtaaacgt taatattttg ttaaaattcg | 17400 |
| cgttaaattt ttgttaaatc agctcatttt ttaacgaata gcccgaaatc ggcaaaatcc | 17460 |
| cttataaatc aaaagaatag accgagatag ggttgagtgt tgttccagtt ccaacaaga | 17520 |
| gtccactatt aaagaacgtg gactccaacg tcaagggcg aaaagggtc tatcagggcg | 17580 |
| atggcccact acgtgaacca tcaccctaat caagtttttt ggggtcgagg tgccgtaaag | 17640 |
| cagtaaatcg gaagggtaaa cggatgcccc catttagagc ttgacgggga aagccggcga | 17700 |
| acgtggcgag aaaggaaggg aagaaagcga aaggagcggg ggctagggcg gtgggaagtg | 17760 |
| taggggtcac gctgggcgta accaccacac ccgccgcgct taatggggcg ctacagggcg | 17820 |
| cgtggggatg atccactagt | 17840 |

<210> SEQ ID NO 9
<211> LENGTH: 1188
<212> TYPE: DNA
<213> ORGANISM: Acidithiobacillus ferrooxidans

<400> SEQUENCE: 9

| atgcgtttcc gtctgaacat cgtactggct accatgatct tctcttctct ggctgtttct | 60 |
| accgctatgg caggcgtgcc tgtgcagtgg tccgttgacg tgcacgcacc gatctacaat | 120 |
| cctcctcgcg ttgcggacgg tgtagcatac ttcgatactg cccagtccaa aggtccaaac | 180 |
| gtgttctctg cgaagaacgg caagatcctg tggcgtttca ccacgggtgg caccatcctg | 240 |
| atgccactga ccgtaggcca cggtcaggtg tgggtagcgt ctgacgtggg ctctacccat | 300 |
| tacctgcgtg cgatcgaagc taagactggt aaaactgatct gggactacac ccgtcacgaa | 360 |
| ccaccggaat gcatgtgttc ccacctgacc cattacgaac atcacctgct gtttgcgcag | 420 |
| accgatggcc actctctgta tgcgttctat cctgtcggca acatcccgaa ccgtcgcctg | 480 |
| tgggctttca ctggtgatgg tgctaaactg actgcaccag ttgtggtgga tcacaccgta | 540 |
| atcttcggtt ctgctgatca cggtgtttac ggtctgttcg acaagactgg caagatccgt | 600 |
| tggcagcaga agacgggtta tggtttcatg gcacagcctg cggtgtggaa acacgaagtg | 660 |
| atcatcggca accgtggtgg tactgttcac gcgtactcta ccaccactgg cacctctctg | 720 |
| tggaacttca cgaccaatgg tcctatcaac acgactgccc tgatctggca tgattctgcc | 780 |
| ttcatcgctt ccggtgcagg tgatcgtggc gtttacgctc tgtccgctaa gactggcaaa | 840 |
| caactgtggt acactcgcat ggcagattac actgcgtatg ctccggttat ggcgaaacag | 900 |
| attgtagtgg ttgcttctca ggacggtaac atgctgggtc tgtctgcgac cactggcaaa | 960 |
| gttctgtggc gttccgaact gcacggtatc cctaagtctc aacctgctct gtggaagggt | 1020 |
| gatgcggtcc tgaaagttaa cgatcacaag atcatggctt tcaatgctca gtctggtggc | 1080 |
| ctggtttgga cttatcactc caagaacgtt gttacctctc cggtgccgaa aggtgatagc | 1140 |
| gtctatgttg gcaccagcgg tggcactctg gtggcgatcg gtcagtaa | 1188 |

<210> SEQ ID NO 10
<211> LENGTH: 19736
<212> TYPE: DNA
<213> ORGANISM: Artificial Sequence
<220> FEATURE:
<223> OTHER INFORMATION: Synthetic Construct

<400> SEQUENCE: 10

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttccta gggccaccat gactgaactt ggttctgata     540 cttttgccctc tgtgggccag tgcaacaaa ttctgactgc gccacccgtc tggcaggtca     600
aggtgcagac tgcatcctgg acaagtgccg cgctggcgct gcgcgatcag ggcgggcgtt     660
tgctgggatt gtggggagag gcgggccatg aaaatgcatt ttttacata catgcgctgg     720 gccttggttc aaccggatat ttgtggatca ctctgacggt gcaatccagc gagggacaat     780
ttccctcgct ggccgacatt tttccgctg cctcgcggat ggagcgggcc ctgtacgatc     840
ttacgggaat cagggcggcg gggaatgccg atacccggcc atggctccgc catcagtgct     900
ggccagcggg gattttttcca ctgcggggagg acaactgga tggcagttcc ttcggcgtgg     960
atggtgatgc cgattatcct tttcaattaa tcgatagcgt ggatgtccac cagattccag    1020
tgggaccggt acacgcgggc accattgagc ccggacactt tcgttttttcg tgtgtcggtg    1080 aacaaattct gcgtctggaa gaacgattgg gatacaccca caagggcgtc gaacgccttt    1140
tccaagatcg ggatgtgttt gcgggtcgcg gtctggcagg acgcatcagt ggtgacacta    1200
cagcgggtta tgcctgggcc tacagcatgg cggtggaatc cattgcccga tgcgaaatcc    1260
cgcctcgtgc agccgctttg cgtgctgttt gcctggaacg ggagcgcatg gccaaccatc    1320
tgggtgatct tgccgctctg gggaatgacg ctggcttcgc cttctgtcag tcacaattcc    1380
tgttcatcaa ggaaagcctg ctgcgcgaaa accaggaaat tttcggacac cgctatttga    1440
tggactgcat tattcccggt ggtgtagctt ttgatctgaa ctccgcgcaa acagccgcga    1500
ttcagcgtaa cagtgaatcc tggcagcgca ccgtgcagcg tttggacctc ctcttgcagg    1560
agcactccgg tctgcgggat cgtctggtgg gtacaggaaa aattgtgcca ccccgtgctg    1620
cagcactcgg tatggcgggg cttgccggcc gcgccagtgg tcaggcctgg gatttgcggg    1680
tccagtttcc ccatgcacct tatcagaatc tggatgtttc catgcagctt tccccggaag    1740
gtgacgtggc cgcacgctgg caattgcgct tcgggaatt ctatgagtct ctgcgtctgc    1800
agacccagtt gctgttggat ctaccagtg gagatgtcag cgcaaccatt ccggaaagca    1860
tccccgatgg cgaaggcttg gcattgtcg aagcatggcg cggcgaggtc tttgtcgccc    1920
tatctgtgga aaacgcccgt attaaacgct gccatcccca cgatccctcg tggaccctct    1980
ggccggtcct tgaggaggcc gtgctgaacg atattgttgc cgactttccg ctgatcaata    2040
aatcgttcaa tttgagttac agcggacatg atttataatt aattaatcat gtaattagtt    2100
atgtcacgct tacattcacg ccctcccccc acatccgctc taaccgaaaa ggaaggagtt    2160
agacaacctg aagtctaggt ccctatttat tttttatag ttatgttagt attaagaacg    2220
ttatttatat ttcaaatttt tcttttttttt ctgtacagac gcgtgtacgc atgtaacatt    2280
atactgaaaa ccttgcttga aaggttttg ggacgctcga aggctttaat ttgccggatt    2340
```

```
agaagccgcc gagcgggtga cagccctccg aaggaagact ctcctccgtg cgtcctcgtc    2400
ttcaccggtc gcgttcctga aacgcagatg tgcctcgcgc cgcactgctc cgaacaataa    2460
agattctaca atactagctt ttatggttat gaagaggaaa aattggcagt aacctggccc    2520
cacaaacctt caaatgaacg aatcaaatta acaaccatag gatgataatg cgattagttt    2580
tttagcctta tttctggggt aattaatcag cgaagcgatg atttttgatc tattaacaga    2640
tatataaatg caaaaactgc ataaccactt taactaatac tttcaacatt ttcggtttgt    2700
attacttctt attcaaatgt aataaaagta tcaacaaaaa attgttaata tacctctata    2760
ctttaacgtc aaggagggcg cgccaccatg tcgactcctg acaatcacgg caagaaagcc    2820
cctcaatttg ctgcgttcaa accgctaacc acggtacaga acgccaacga ctgttgctgc    2880
gacggcgcat gttccagcac gccaactctc tctgaaaacg tctccggcac ccgctatagc    2940
tggaaagtca gcggcatgga ctgcgccgcc tgtgcgcgca aggtagaaaa tgccgtgcgc    3000
cagcttgcag gcgtgaatca ggtgcaggtg ttgttcgcca ccgaaaaact ggtggtcgat    3060
gccgacaatg acattcgtgc acaagttgaa tctgcgctgc aaaaagcagg ctattccctg    3120
cgcgatgaac aggccgccga agaaccgcaa gcatcacgcc tgaaagagaa tctgccgctg    3180
attacgctaa tcgtgatgat ggcaatcagc tggggtctgg agcagttcaa tcatccgttc    3240
gggcaactgg cgtttatcgc gaccacgctg gttgggctgt acccgattgc tcgtcaggca    3300
ttacggttga tcaaatccgg cagctacttc gccattgaaa ccttaatgag cgtagccgct    3360
attggtgcac tgtttattgg cgcaacggct gaagctgcga tggtgttgct gctgttttg    3420
attggtgaac gactggaagg ctgggccgcc agccgcgcgc gtcagggcgt tagcgcgtta    3480
atggcgctga aaccagaaac cgccacgcgc ctgcgtaagg gtgagcggga agaggtggcg    3540
attaacagcc tgcgccctgg cgatgtgatt gaagtcgccg caggtgggcg tttgcctgcc    3600
gacggtaaac tgctctcacc gtttgccagt tttgatgaaa gcgccctgac cggcgaatcc    3660
attccggtgg agcgcgcaac gggcgataaa gtccctgctg gtgccaccag cgtagaccgt    3720
ctggtgacgt tggaagtgct gtcagaaccg ggagccagcg ccattgaccg gattctgaaa    3780
ctgatcgaag aagccgaaga gcgtcgcgct cccattgagc ggtttatcga ccgttttcagc    3840
cgtatctata cgcccgcgat tatggccgtc gctctgctgg tgacgctggt gccaccgctg    3900
ctgtttgccg ccagctggca ggagtggatt tataaagggc tgacgctgct gctgattggc    3960
tgcccgtgtg cgttagttat ctcaacgcct gcggcgatta cctccgggct ggcggcggca    4020
gcgcgtcgtg gggcgttgat taaaggcgga cggcgctgg aacagctggg tcgtgttact    4080
caggtggcgt ttgataaaac cggtacgctg accgtcggta aaccgcgcgt taccgcgatt    4140
catccggcaa cgggtattag tgaatctgaa ctgctgacac tggcggcggc ggtcgagcaa    4200
ggcgcgacgc atccactggc gcaagccatc gtacgcgaag cacaggttgc tgaactcgcc    4260
attcccaccg ccgaatcaca gcgggcgctg gtcgggtctg gcattgaagc gcaggttaac    4320
ggtgagcgcg tattgatttg cgctgccggg aaacatcccg ctgatgcatt tactggttta    4380
attaacgaac tggaaagcgc cgggcaaacg gtagtgctgg tagtacgtaa cgatgacgtg    4440
cttggtgtca ttgcgttaca ggataccctg cgcgccgatg ctgcaactgc catcagtgaa    4500
ctgaacgcgc tgggcgtcaa aggggtgatc ctcaccggcg ataatccacg cgcagcggcg    4560
gcaattgccg gggagctggg gctggagttt aaagcgggcc tgttgccgga agataaagtc    4620
aaagcggtga ccgagctgaa tcaacatgcg ccgctgcgca tggtcggtga cggtattaac    4680
gacgcgccag cgatgaaagc tgccgccatc gggattgcaa tgggtagcgg cacagacgtg    4740
```

-continued

```
gcgctggaaa ccgccgacgc agcattaacc cataaccacc tgcgcggcct ggtgcaaatg    4800
attgaactgg cacgcgccac tcacgccaat atccgccaga acatcactat tgcgctgggg    4860
ctgaaaggga tcttcctcgt caccacgctg ttagggatga ccgggttgtg gctggcagtg    4920
ctggcagata cgggggcgac ggtgctggtg acagcgaatg cgttaagatt gttgcgcagg    4980
agataataac ttaagtcatg taattagtta tgtcacgctt acattcacgc cctcccccca    5040
catccgctct aaccgaaaag gaaggagtta gacaacctga agtctaggtc cctatttatt    5100
tttttatagt tatgttagta ttaagaacgt tatttatatt tcaaattttt ctttttttc    5160 tgtacagacg cgtgtacgca tgtaacatta tactgaaaac cttgcttgag aaggttttgg    5220
gacgctcgaa ggctttaatt tgccggatta gaagccgccg agcgggtgac agccctccga    5280
aggaagactc tcctccgtgc gtcctcgtct caccggtcg cgttcctgaa acgcagatgt    5340
gcctcgcgcc gcactgctcc gaacaataaa gattctacaa tactagcttt tatggttatg    5400
aagaggaaaa attggcagta acctggcccc acaaaccttc aaatgaacga atcaaattaa    5460
caaccatagg atgataatgc gattagtttt ttagccttat ttctggggta attaatcagc    5520
gaagcgatga ttttttgatct attaacagat atataaatgc aaaaactgca taaccacttt    5580
aactaatact ttcaacatt tcggtttgta ttacttctta ttcaaatgta ataaagtat    5640 caacaaaaaa ttgttaatat acctctatac tttaacgtca aggaggaatt catgacgaaa    5700
acgcgctcga acatggcgcg ctacggcacc agcctggcca tcgtgctggg cgtgcacgtg    5760
gtcgccgtgg tgctgacgct caactggtcg gtgcccagg ccatcgagct gccgccggca    5820
gcgatgatgg tcgagttggc gccgttgccg gagcccgcgc caccgccacc gcccaaggcc    5880
gcgcccaagc caccggcaga ggtcgaggag ccgccgctgc ccaagctggt ggaggccccc    5940
aagccgaaga tcgccatcgc caagccgccc aagcccaagg ccaagccgca gccgcccaag    6000
cctgagaaaa agcctgagcc gccgaaggac gaaccaccgg ccaaggacga tgtggcggat    6060
accccgccaa gcaacgcgca gccgcagaaa tcggccgcac cggcaccgag catcgcctcc    6120
aacagcaatg ccctgcccag ctggcagagc gacctgctgc gccacctggc caagtacaag    6180
aagtacccgg aagacgctcg ccgtcgcggc ctgcagggca tcaaccgcct gcgcttcgtg    6240
gtcgacgccg agggcaaggt agtctcgtac tcgctggccg gaggctcggg cagcgcggcg    6300
ctggaccggg cgaccctgga aatgatccgt cgcgcaggct ccgtaccgaa gccgccagcg    6360
gagctgttga caatggcac gatcgaagtc gtggcgccgt tcgtctattc cctggaccga    6420
cgctaagttt aaactcatgt aattagttat gtcacgctta cattcacgcc ctccccccac    6480
atccgctcta accgaaaagg aaggagttag acaacctgaa gtctaggtcc ctatttattt    6540
ttttatagtt atgttagtat taagaacgtt atttatattt caaattttc ttttttttct    6600 gtacagacgc gtgtacgcat gtaacattat actgaaaacc ttgcttgaga aggttttggg    6660
acgctcgaag ctttaatttt gccggattag aagccgccga gcgggtgaca gccctccgaa    6720
ggaagactct cctccgtgcg tcctcgtctt caccggtcgc gttcctgaaa cgcagatgtg    6780
cctcgcgccg cactgctccg aacaataaag attctacaat actagctttt atggttatga    6840
agaggaaaaa ttggcagtaa cctggcccca caaaccttca aatgaacgaa tcaaattaac    6900
aaccatagga tgataatgcg attagttttt tagccttatt tctggggtaa ttaatcagcg    6960
aagcgatgat ttttgatcta ttaacagata tataaatgca aaaactgcat aaccacttta    7020
actaatactt tcaacatttt cggtttgtat tacttcttat tcaaatgtaa taaagtatc    7080
```

```
aacaaaaaat tgttaatata cctctatact ttaacgtcaa ggaggagctc accatggctg    7140
aaggtgtttt ccaaggtgct atcggtatcg atttaggtac aacctactct tgtgttgcta    7200
cttacgaatc ctccgttgaa attattgcca acgaacaagg taacagagtc accccatctt    7260
tcgttgcttt cactccagaa gaaagattga ttggtgatgc tgccaagaac caagctgctt    7320
tgaacccaag aaacactgtc ttcgatgcta agcgtttgat tggtagaaga ttcgacgacg    7380
aatctgttca aaaggacatg aagacctggc ctttcaaggt tatcgacgtc gatggtaacc    7440
cagtcatcga agtccaatac ttggaagaaa ccaagacttt ctccccacaa gaaatttccg    7500
ctatggtttt gaccaagatg aaggaaattg ctgaagctaa gattggtaag aaggttgaaa    7560
aggccgtcat tactgtccca gcttacttta acgacgctca aagacaagct accaaggatg    7620
ccggtgccat ttctggtttg aacgttttgc gtatcatcaa cgaacctact gccgctgcta    7680
ttgcttacgg tctaggtgct ggtaagtccg aaaaggaaag acatgttttg attttcgatt    7740
tgggtggtgg tactttcgat gtttccttgt tgcacattgc tggtggtgtt tacactgtta    7800
aatctacttc cggtaacact cacttgggtg gtcaagattt cgacaccaac ttgttggaac    7860
acttcaaggc tgaattcaag aagaagactg gtttggacat ctccgacgat gccagagctt    7920
tgagaagatt gagaactgct gctgaaagag ctaagagaac cttatcttct gtcactcaaa    7980
ctaccgttga agttgactct ttgtttgacg gtgaagattt cgaatcctct ttgactagag    8040
ctagatttga agacttgaac gccgcattgt tcaagtctac tttggaacct gttgaacaag    8100
ttttgaagga tgctaagatc tctaagtctc aaatcgacga agttgtcttg gttggtggtt    8160
ccaccagaat tccaaaggtc caaaagttgt tgtctgactt ctttgacggt aagcaattgg    8220
aaaaatctat taacccagat gaagctgttg cttacggtgc tgctgttcaa ggtgctatct    8280
tgaccggcca atccacatct gacgaaacca aggacttgtt gttgttagat gttgctccat    8340
tatctctagg tgttggtatg caaggtgaca tgttcggtat cgttgttcca agaaacacta    8400
ctgttccaac catcaagaga gaaccttta ctacatgtgc tgacaaccaa accaccgttc    8460
aattcccagt ctaccaaggt gaacgtgtta actgtaaaga aaacactttg ttgggtgaat    8520
tcgacttgaa gaacatccca atgatgccag ctggtgaacc agtcttggaa gctatcttcg    8580
aagttgatgc taacggtatc ttgaaggtta ctgccgtcga aaagtctacc ggtaagtctt    8640
ctaacatcac tatctctaac gctgttggta gattgtcttc tgaagaaatt gaaaagatgg    8700
ttaaccaagc tgaagagttc aaggctgccg atgaagcttt tgccaagaag cacgaagcta    8760
gacaaagatt ggaatcctac gttgcctcca tcgaacaaac tgtcactgac ccagtcttgt    8820
cttctaaatt gaagagaggt tccaagtcca agattgaagc tgctttgtcc gatgctttgg    8880
ctgctttgca aatcgaagac ccatctgctg atgaattgag aaaggctgaa gttggtttga    8940
agagagttgt caccaaggcc atgtcttctc gttaactcga gtcatgtaat tagttatgtc    9000
acgcttacat tcacgccctc cccccacatc cgctctaacc gaaaggaag gagttagaca    9060 acctgaagtc taggtcccta tttatttttt tatagttatg ttagtattaa gaacgttatt    9120
tatatttcaa attttcttt ttttctgta cagacgcgtg tacgcatgta acattatact    9180 gaaaccttg cttgagaagg ttttgggacg ctcgaaggct taatttgcc ggattagaag    9240 ccgccgagcg ggtgacagcc ctccgaagga agactctcct ccgtgcgtcc tcgtcttcac    9300
cggtcgcgtt cctgaaacgc agatgtgcct cgcgccgcac tgctccgaac aataaagatt    9360
ctacaatact agcttttatg gttatgaaga ggaaaaattg gcagtaacct ggccccacaa    9420
accttcaaat gaacgaatca aattaacaac cataggatga taatgcgatt agttttttag    9480
```

```
ccttatttct ggggtaatta atcagcgaag cgatgatttt tgatctatta acagatatat   9540
aaatgcaaaa actgcataac cactttaact aatactttca acattttcgg tttgtattac   9600
ttcttattca aatgtaataa aagtatcaac aaaaaattgt taatatacct ctatacttta   9660
acgtcaagga gcccggggcc accatgcgtt tccgtctgaa catcgtactg gctaccatga   9720
tcttctcttc tctggctgtt tctaccgcta tggcaggcgt gcctgtgcag tggtccgttg   9780
acgtgcacgc accgatctac aatcctcctc gcgttgcgga cggtgtagca tacttcgata   9840
ctgcccagtc caaaggtcca aacgtgttct ctgcgaagaa cggcaagatc ctgtggcgtt   9900
tcaccacggg tggcaccatc ctgatgccac tgaccgtagg ccacggtcag gtgtgggtag   9960
cgtctgacgt gggctctacc cattacctgc gtgcgatcga agctaagact ggtaaactga  10020
tctgggacta cacccgtcac gaaccaccgg aatgcatgtg ttcccacctg acccattacg  10080
aacatcacct gctgtttgcg cagaccgatg ccactctct gtatgcgttc tatcctgtcg  10140
gcaacatccc gaaccgtcgc ctgtgggctt tcactggtga tggtgctaaa ctgactgcac  10200
cagttgtggt ggatcacacc gtaatcttcg ttctgctga tcacggtgtt tacggtctgt  10260
tcgacaagac tggcaagatc cgttggcagc agaagacggg ttatggtttc atggcacagc  10320
ctgcggtgtg gaaacacgaa gtgatcatcg gcaaccgtgg tggtactgtt cacgcgtact  10380
ctaccaccac tggcacctct ctgtggaact tcacgaccaa tggtcctatc aacacgactg  10440
ccctgatctg gcatgattct gccttcatcg cttccggtgc aggtgatcgt ggcgtttacg  10500
ctctgtccgc taagactggc aaacaactgt ggtacactcg catggcagat tacactgcgt  10560
atgctccggt tatggcgaaa cagattgtag tggttgcttc tcaggacggt aacatgctgg  10620
gtctgtctgc gaccactggc aaagttctgt ggcgttccga actgcacggt atccctaagt  10680
ctcaacctgc tctgtggaag ggtgatgcgg tcctgaaagt taacgatcac aagatcatgg  10740
ctttcaatgc tcagtctggt ggcctggttt ggacttatca ctccaagaac gttgttacct  10800
ctccggtgcc gaaaggtgat agcgtctatg ttggcaccag cggtggcact ctggtggcga  10860
tcggtcagta aggtacctca tgtaattagt tatgtcacgc ttacattcac gccctccccc  10920
cacatccgct ctaaccgaaa aggaaggagt tagacaacct gaagtctagg tccctattta  10980
ttttttata gttatgttag tattaagaac gttatttata tttcaaattt tcttttttt  11040
tctgtacaga cgcgtgtacg catgtaacat tatactgaaa accttgcttg agaaggtttt  11100
gggacgctcg aaggctttaa tttgccggat tagaagccgc cgagcgggtg acagccctcc  11160
gaaggaagac tctcctccgt gcgtcctcgt cttcaccggt cgcgttcctg aaacgcagat  11220
gtgcctcgcg ccgcactgct ccgaacaata aagattctac aatactagct tttatggtta  11280
tgaagaggaa aaattggcag taacctggcc ccacaaacct tcaaatgaac gaatcaaatt  11340
aacaaccata ggatgataat gcgattagtt ttttagcctt atttctgggg taattaatca  11400
gcgaagcgat gatttttgat ctattaacag atatataaat gcaaaaactg cataaccact  11460
ttaactaata cttttcaacat tttcggtttg tattacttct tattcaaatg taataaagt  11520
atcaacaaaa aattgttaat atacctctat actttaacgt caaggaggga tccgccacca  11580
tgtctcaatc cgtagaatca cggactcgaa tcaaaaacga acgttacgaa tcaggtgtta  11640
tcccttacgc aaaaatggga tactgggatg ctgattacgt tatcaaagat actgacgtac  11700
ttgcaatgtt ccgtatgaca cctcaaaaag gtgttgaccc agttgaatgt gcagccgcaa  11760
tcgcaggtga atcttcaaca gcaacttgga cagttgtatg gacagacctt ctaacagcat  11820
```

-continued

```
gtgatcttta ccgtgcaaaa gcataccgtg ttgacccagt tcctggtgca actgatcaat   11880
actttgctta catcgcatac gaattagacc tatttgaaga aggttcttta gctaacttaa   11940
cagcatcaat tattggtaac gtattcggat tcaaagcggt aaatgcttta agattagaag   12000
atatgcgtct tccaattgca tacctaaaaa ctttccaagg tccagcaact ggtgtaattg   12060
tagaacgtga agattagac aaatatggtc gtcctttatt aggtgcaaca gttaaaccaa    12120
aattaggtct atctggtaaa aactatggtc gtgtagttta cgaaggtctt aaaggtggtc   12180
tagatttcct taaagatgat gaaaacatta actctcaacc attcatgaga tggaaagagc   12240
gtttcttatt cggtatcgaa ggtgtaaacc gtgctgctgc tgctgctggt gaagtaaaag   12300
gtcactactt caacgttact gctggtacaa tggaagatat gtatgaacgt gctgaattct   12360
gtaaagaaat cggtagtgta atctgtatga tcgaccttgt aatcggatat actgctattc   12420
aaagtatggc gatctgggca cgtaaaaaca gtatgattct tcacttacac cgtgctggta   12480
actctacata ctcacgtcaa aaaacacatg gtatgaactt ccgtgtaatt tgtaagtgga   12540
tgcgtatggc aggtgttgac cacatacacg caggtacagt tgtaggtaaa ctagaagggg   12600 atccttaat ggttaaaggt ttctataaca cattattaga aacacaaaca gatgtaaatc    12660
ttgtacaagg tcttttcttt gctcaagatt gggcagcact taacaaatgt atgccagttg   12720
cttcaggtgg tattcactgt ggtcaaatgc accaacttat taactactta ggtgacgacg   12780
tagtattaca atttggtggt ggtactattg gtcacccaga tggtatccaa gctggtgcta   12840
ctgcaaaccg tgtagcactt gaatgtatgg ttgtagcacg taacgaaggt cgtgactatg   12900
taacagaggg tcctcaaatt cttcgtaatg cagctaagag ctgtggacct cttcaaacag   12960
cattagattt atggaaagac attactttca actatgcttc tactgataca gctgacttcg   13020
tagaaactgc aacagctaac aagtaagaat tctcatgtaa ttagttatgt cacgcttaca   13080
ttcacgccct cccccacat ccgctctaac cgaaaaggaa ggagttagac aacctgaagt    13140
ctaggtccct atttattttt ttatagttat gttagtatta agaacgttat ttatatttca   13200 aattttttctt ttttttctgt acagacgcgt gtacgcatgt aacattatac tgaaaacctt   13260
gcttgagaag gttttgggac gctcgaaggc tttaatttgc cggattagaa gccgccgagc   13320
gggtgacagc cctccgaagg aagactctcc tccgtgcgtc ctcgtcttca ccggtcgcgt   13380
tcctgaaacg cagatgtgcc tcgcgccgca ctgctccgaa caataaagat tctacaatac   13440
tagcttttat ggttatgaag aggaaaaatt ggcagtaacc tggccccaca aaccttcaaa   13500
tgaacgaatc aaattaacaa ccataggatg ataatgcgat tagttttta gccttatttc    13560 tggggtaatt aatcagcgaa gcgatgattt ttgatctatt aacagatata taaatgcaaa   13620
aactgcataa ccactttaac taatactttc aacattttcg gtttgtatta cttcttattc   13680
aaatgtaata aaagtatcaa caaaaaattg ttaatatacc tctatacttt aacgtcaagg   13740
aggcggccgc caccatggtg agcaagggcg aggagctgtt caccggggtg gtgcccatcc   13800
tggtcgagct ggacggcgac gtaaacggcc acaagttcag cgtgtccggc gagggcgagg   13860
gcgatgccac ctacggcaag ctgaccctga agttcatctg caccaccggc aagctgcccg   13920
tgccctggcc caccctcgtg accacccctga cctacggcgt gcagtgcttc agccgctacc   13980
ccgaccacat gaagcagcac gacttcttca gtccgccat gcccgaaggc tacgtccagg    14040
agcgcaccat cttcttcaag gacgacggca actacaagac ccgcgccgag gtgaagttcg   14100
agggcgacac cctggtgaac cgcatcgagc tgaagggcat cgacttcaag gaggacggca   14160
acatcctggg gcacaagctg gagtacaact acaacagcca caacgtctat atcatggccg   14220
```

```
acaagcagaa gaacggcatc aaggtgaact tcaagatccg ccacaacatc gaggacggca   14280
gcgtgcagct cgccgaccac taccagcaga acaccccat cggcgacggc cccgtgctgc   14340
tgcccgacaa ccactacctg agcacccagt ccgccctgag caaagacccc aacgagaagc   14400
gcgatcacat ggtcctgctg gagttcgtga ccgccgccgg gatcactctc ggcatggacg   14460
agctgtacaa gtaatctaga gggccgcatc atgtaattag ttatgtcacg cttacattca   14520
cgccctcccc ccacatccgc tctaaccgaa aggaaggag ttagacaacc tgaagtctag   14580
gtccctattt atttttttat agttatgtta gtattaagaa cgttatttat atttcaaatt   14640
tttctttttt ttctgtacag acgcgtgtac gcatgtaaca ttatactgaa aaccttgctt   14700
gagaaggttt tgggacgctc gaaggcttta atttgcggcc ctgcattaat gaatcggcca   14760
acgcgcgggg agaggcggtt tgcgtattgg gcgctcttcc gcttcctcgc tcactgactc   14820
gctgcgctcg gtcgttcggc tgcggcgagc ggtatcagct cactcaaagg cggtaatacg   14880
gttatccaca gaatcagggg ataacgcagg aaagaacatg tgagcaaaag gccagcaaaa   14940
gcccaggaac cgtaaaaagg ccgcgttgct ggcgtttttc cataggctcc gccccctga   15000 cgagcatcac aaaatcgac gctcaagtca gaggtggcga acccgacag gactataaag   15060 ataccaggcg tttccccctg aagctccct cgtgcgctct cctgttccga ccctgccgct   15120
taccggatac ctgtccgcct ttctcccttc gggaagcgtg gcgctttctc atagctcacg   15180
ctgtaggtat ctcagttcgg tgtaggtcgt tcgctccaag ctgggctgtg tgcacgaacc   15240
ccccgttcag cccgaccgct gcgccttatc cggtaactat cgtcttgagt ccaacccggt   15300
aagacacgac ttatcgccac tggcagcagc cactggtaac aggattagca gagcgaggta   15360
tgtaggcggt gctacagagt tcttgaagtg gtggcctaac tacggctaca ctagaaggac   15420
agtatttggt atctgcgctc tgctgaagcc agttaccttc ggaaaaagag ttggtagctc   15480
ttgatccggc aaacaaacca ccgctggtag cggtggtttt tttgtttgca agcagcagat   15540
tacgcgcaga aaaaaaggat ctcaagaaga tcctttgatc ttttctacgg ggtctgacgc   15600
tcagtggaac gaaaactcac gttaagggat tttggtcatg agattatcaa aaaggatctt   15660
cacctagatc cttttaaatt aaaaatgaag ttttaaatca atctaaagta tatatgagta   15720
aacttggtct gacagttacc aatgcttaat cagtgaggca cctatctcag cgatctgtct   15780
atttcgttca tccatagttg cctgactccc cgtcgtgtag ataactacga tacgggagcg   15840
cttaccatct ggccccagtg ctgcaatgat accgcgagac ccacgctcac cggctccaga   15900
tttatcagca ataaaccagc cagccggaag ggccgagcgc agaagtggtc ctgcaacttt   15960
atccgcctcc atccagtcta ttaattgttg ccgggaagct agagtaagta gttcgccagt   16020
taatagtttg cgcaacgttg ttggcattgc tacaggcatc gtggtgtcac tctcgtcgtt   16080
tggtatggct tcattcagct ccggttccca acgatcaagg cgagttacat gatcccccat   16140
gttgtgcaaa aaagcggtta gctccttcgg tcctccgatc gttgtcagaa gtaagttggc   16200
cgcagtgtta tcactcatgg ttatggcagc actgcataat tctcttactg tcatgccatc   16260
cgtaagatgc ttttctgtga ctggtgagta ctcaaccaag tcattctgag aatagtgtat   16320
gcggcgaccg agttgctctt gcccggcgtc aatacgggat aatagtgtat cacatagcag   16380
aactttaaaa gtgctcatca ttggaaaacg ttcttcgggg cgaaaactct caaggatctt   16440
accgctgttg agatccagtt cgatgtaacc cactcgtgca cccaactgat cttcagcatc   16500
ttttactttc accagcgttt ctgggtgagc aaaaacagga aggcaaaatg ccgcaaaaaa   16560
```

```
gggaataagg gcgacacgga aatgttgaat actcatactc ttccttttc aatgggtaat      16620 aactgatata attaaattga agctctaatt tgtgagttta gtatacatgc atttacttat      16680
aatacagttt tttagttttg ctggccgcat cttctcaaat atgcttccca gcctgctttt      16740
ctgtaacgtt caccctctac cttagcatcc cttcccttg caaatagtcc tcttccaaca       16800
ataataatgt cagatcctgt agagaccaca tcatccacgg ttctatactg ttgacccaat      16860
gcgtctccct tgtcatctaa acccacaccg ggtgtcataa tcaaccaatc gtaaccttca      16920
tctcttccac ccatgtctct ttgagcaata aagccgataa caaaatcttt gtcgctcttc      16980
gcaatgtcaa cagtacccctt agtatattct ccagtagata gggagcccctt gcatgacaat    17040 tctgctaaca tcaaaaggcc tctaggttcc tttgttactt cttctgccgc ctgcttcaaa      17100
ccgctaacaa tacctgggcc caccacaccg tgtgcattcg taatgtctgc ccattctgct      17160
attctgtata cacccgcaga gtactgcaat ttgactgtat taccaatgtc agcaaatttt      17220
ctgtcttcga agagtaaaaa attgtacttg gcggataatg cctttagcgg cttaactgtg      17280
ccctccatgg aaaatcagt caagatatcc acatgtgttt ttagtaaaca aattttggga       17340
cctaatgctt caactaactc cagtaattcc ttggtggtac gaacatccaa tgaagcacac      17400
aagtttgttt gcttttcgtg catgatatta aatagcttgg cagcaacagg actaggatga     17460
gtagcagcac gttccttata tgtagctttc gacatgattt atcttcgttt cctgcaggtt      17520
tttgttctgt gcagttgggt taagaatact gggcaatttc atgtttcttc aacactacat      17580
atgcgtatat ataccaatct aagtctgtgc tccttccttc gttcttcctt ctgttcggag      17640
attaccgaat caaaaaaatt tcaaagaaac cgaaatcaaa aaaagaata aaaaaaat         17700 gatgaattga attgaaaagc tagcttatcg atgataagct gtcaaagatg agaattaatt      17760
ccacggacta tagactatac tagatactcc gtctactgta cgatacactt ccgctcaggt      17820
ccttgtcctt taacgaggcc ttaccactct tttgttactc tattgatcca gctcagcaaa      17880
ggcagtgtga tctaagattc tatcttcgcg atgtagtaaa actagctaga ccgagaaaga     17940
gactagaaat gcaaaaggca cttctacaat ggctgccatc attattatcc gatgtgacgc      18000
tgcagcttct caatgatatt cgaatacgct ttgaggagat acagcctaat atccgacaaa      18060
ctgttttaca gatttacgat cgtacttgtt acccatcatt gaattttgaa catccgaacc      18120
tgggagtttt ccctgaaaca gatagtatat ttgaacctgt ataataatat atagtctagc      18180
gctttacgga agacaatgta tgtatttcgg ttcctggaga aactattgca tctattgcat      18240
aggtaatctt gcacgtcgca tccccggttc attttctgcg tttccatctt gcacttcaat     18300
agcatatctt tgttaacgaa gcatctgtgc ttcattttgt agaacaaaaa tgcaacgcga      18360
gagcgctaat ttttcaaaca aagaatctga gctgcatttt tacagaacag aaatgcaacg     18420
cgaaagcgct atttttaccaa cgaagaatct gtgcttcatt tttgtaaaac aaaaatgcaa    18480
cgcgacgaga gcgctaattt ttcaaacaaa gaatctgagc tgcattttta cagaacagaa     18540
atgcaacgcg agagcgctat tttaccaaca aagaatctat acttcttttt tgttctacaa      18600
aaatgcatcc cgagagcgct attttttctaa caaagcatct tagattactt ttttctcct     18660 ttgtgcgctc tataatgcag tctcttgata acttttgca ctgtaggtcc gttaaggtta      18720
gaagaaggct actttggtgt ctattttctc ttccataaaa aaagcctgac tccacttccc      18780
gcgtttactg attactagcg aagctgcggg tgcatttttt caagataaag gcatccccga      18840
ttatattcta taccgatgtg gattgcgcat actttgtgaa cagaaagtga tagcgttgat      18900
gattcttcat tggtcagaaa attatgaacg gtttcttcta ttttgtctct atatactacg      18960
```

| | | | | |
|---|---|---|---|---|
| tataggaaat | gtttacattt | tcgtattgtt | ttcgattcac | tctatgaata gttcttacta | 19020 |
| caatttttt | gtctaaagag | taatactaga | gataaacata | aaaaatgtag aggtcgagtt | 19080 |
| tagatgcaag | ttcaaggagc | gaaaggtgga | tgggtaggtt | atatagggat atagcacaga | 19140 |
| gatatatagc | aaagagatac | ttttgagcaa | tgtttgtgga | agcggtattc gcaatgggaa | 19200 |
| gctccacccc | ggttgataat | cagaaaagcc | ccaaaaacag | gaagattgta taagcaaata | 19260 |
| tttaaattgt | aaacgttaat | attttgttaa | aattcgcgtt | aaattttgt taaatcagct | 19320 |
| catttttta | cgaatagccc | gaaatcggca | aaatccctta | taaatcaaaa gaatagaccg | 19380 |
| agatagggtt | gagtgttgtt | ccagtttcca | acaagagtcc | actattaaag aacgtggact | 19440 |
| ccaacgtcaa | agggcgaaaa | agggtctatc | agggcgatgg | cccactacgt gaaccatcac | 19500 |
| cctaatcaag | tttttgggg | tcgaggtgcc | gtaaagcagt | aaatcggaag ggtaaacgga | 19560 |
| tgcccccatt | tagagcttga | cggggaaagc | cggcgaacgt | ggcgagaaag gaagggaaga | 19620 |
| aagcgaaagg | agcgggggct | agggcggtgg | gaagtgtagg | ggtcacgctg ggcgtaacca | 19680 |
| ccacacccgc | cgcgcttaat | ggggcgctac | agggcgcgtg | gggatgatcc actagt | 19736 |

<210> SEQ ID NO 11
<211> LENGTH: 14382
<212> TYPE: DNA
<213> ORGANISM: Artificial Sequence
<220> FEATURE:
<223> OTHER INFORMATION: Synthetic Construct

<400> SEQUENCE: 11

| | | | | |
|---|---|---|---|---|
| aagaaaccaa | ttgtccatat | tgcatcagac | attgccgtca | ctgcgtcttt tactggctct | 60 |
| tctcgctaac | caaaccggta | accccgctta | ttaaaagcat | tctgtaacaa agcgggacca | 120 |
| aagccatgac | aaaaacgcgt | aacaaaagtg | tctataatca | cggcagaaaa gtccacattg | 180 |
| attatttgca | cggcgtcaca | ctttgctatg | ccatagcatt | tttatccata agattagcgg | 240 |
| atcctacctg | acgcttttta | tcgcaactct | ctactgtttc | tccatacccg ttttttgggc | 300 |
| taacaggagg | aattaaccat | ggctgaaggt | gttttccaag | gtgctatcgg tatcgattta | 360 |
| ggtacaacct | actcttgtgt | tgctacttac | gaatcctccg | ttgaaattat tgccaacgaa | 420 |
| caaggtaaca | gagtcacccc | atctttcgtt | gctttcactc | cagaagaaag attgattggt | 480 |
| gatgctgcca | gaaccaagc | tgctttgaac | ccaagaaaca | ctgtcttcga tgctaagcgt | 540 |
| ttgattggta | gaagattcga | cgacgaatct | gttcaaaagg | acatgaagac ctggccttc | 600 |
| aaggttatcg | acgtcgatgg | taacccagtc | atcgaagtcc | aatacttgga agaaaccaag | 660 |
| actttctccc | cacaagaaat | tccgctatg | gttttgacca | agatgaagga aattgctgaa | 720 |
| gctaagattg | gtaagaaggt | tgaaaaggcc | gtcattactg | tcccagctta ctttaacgac | 780 |
| gctcaaagac | aagctaccaa | ggatgccggt | gccatttctg | gtttgaacgt tttgcgtatc | 840 |
| atcaacgaac | ctactgccgc | tgctattgct | tacggtctag | gtgctggtaa gtccgaaaag | 900 |
| gaaagacatg | ttttgatttt | cgatttgggt | ggtggtactt | tcgatgtttc cttgttgcac | 960 |
| attgctggtg | gtgtttacac | tgttaaatct | acttccggta | acactcactt gggtggtcaa | 1020 |
| gatttcgaca | ccaacttgtt | ggaacacttc | aaggctgaat | tcaagaagaa gactggtttg | 1080 |
| gacatctccg | acgatgccag | agcttttgaga | agattgagaa | ctgctgctga aagagctaag | 1140 |
| agaaccttat | cttctgtcac | tcaaactacc | gttgaagttg | actctttgtt tgacggtgaa | 1200 |
| gatttcgaat | cctctttgac | tagagctaga | tttgaagact | gaacgccgc attgttcaag | 1260 |

-continued

| | |
|---|---|
| tctactttgg aacctgttga acaagttttg aaggatgcta agatctctaa gtctcaaatc | 1320 |
| gacgaagttg tcttggttgg tggttccacc agaattccaa aggtccaaaa gttgttgtct | 1380 |
| gacttctttg acggtaagca attggaaaaa tctattaacc cagatgaagc tgttgcttac | 1440 |
| ggtgctgctg ttcaaggtgc tatcttgacc ggccaatcca catctgacga aaccaaggac | 1500 |
| ttgttgttgt tagatgttgc tccattatct ctaggtgttg gtatgcaagg tgacatgttc | 1560 |
| ggtatcgttg ttccaagaaa cactactgtt ccaaccatca agagaagaac ctttactaca | 1620 |
| tgtgctgaca accaaaccac cgttcaattc ccagtctacc aaggtgaacg tgttaactgt | 1680 |
| aaagaaaaca ctttgttggg tgaattcgac ttgaagaaca tcccaatgat gccagctggt | 1740 |
| gaaccagtct tggaagctat cttcgaagtt gatgctaacg gtatcttgaa ggttactgcc | 1800 |
| gtcgaaaagt ctaccggtaa gtcttctaac atcactatct ctaacgctgt tggtagattg | 1860 |
| tcttctgaag aaattgaaaa gatggttaac caagctgaag agttcaaggc tgccgatgaa | 1920 |
| gcttttgcca agaagcacga agctagacaa agattggaat cctacgttgc ctccatcgaa | 1980 |
| caaactgtca ctgacccagt cttgtcttct aaattgaaga gaggttccaa gtccaagatt | 2040 |
| gaagctgctt tgtccgatgc tttggctgct ttgcaaatcg aagacccatc tgctgatgaa | 2100 |
| ttgagaaagg ctgaagttgg tttgaagaga gttgtcacca aggccatgtc ttctcgttaa | 2160 |
| ggcgcgcctt tgtttaactt taagaaggag atataccatg cgtttccgtc tgaacatcgt | 2220 |
| actggctacc atgatcttct cttctctggc tgttttctacc gctatggcag gcgtgcctgt | 2280 |
| gcagtggtcc gttgacgtgc acgcaccgat ctacaatcct cctcgcgttg cggacggtgt | 2340 |
| agcatacttc gatactgccc agtccaaagg tccaaacgtg ttctctgcga agaacggcaa | 2400 |
| gatcctgtgg cgtttcacca cgggtggcac catcctgatg ccactgaccg taggccacgg | 2460 |
| tcaggtgtgg gtagcgtctg acgtgggctc tacccattac ctgcgtgcga tcgaagctaa | 2520 |
| gactggtaaa ctgatctggg actacacccg tcacgaacca ccggaatgca tgtgttccca | 2580 |
| cctgacccat tacgaacatc acctgctgtt tgcgcagacc gatggccact ctctgtatgc | 2640 |
| gttctatcct gtcggcaaca tcccgaaccg tcgcctgtgg gctttcactg gtgatggtgc | 2700 |
| taaactgact gcaccagttg tggtggatca caccgtaatc ttcggttctg ctgatcacgg | 2760 |
| tgtttacggt ctgttcgaca agactggcaa gatccgttgg cagcagaaga cgggttatgg | 2820 |
| tttcatggca cagcctgcgg tgtggaaaca cgaagtgatc atcggcaacc gtggtggtac | 2880 |
| tgttcacgcg tactctacca ccactggcac ctctctgtgg aacttcacga ccaatggtcc | 2940 |
| tatcaacacg actgccctga tctggcatga ttctgccttc atcgcttccg gtgcaggtga | 3000 |
| tcgtggcgtt tacgctctgt ccgctaagac tggcaaacaa ctgtggtaca ctcgcatggc | 3060 |
| agattacact gcgtatgctc cggttatggc gaaacagatt gtagtggttg cttctcagga | 3120 |
| cggtaacatg ctgggtctgt ctgcgaccac tggcaaagtt ctgtggcgtt ccgaactgca | 3180 |
| cggtatccct aagtctcaac ctgctctgtg gaagggtgat gcggtcctga agttaacga | 3240 |
| tcacaagatc atggctttca atgctcagtc tggtggcctg gtttggactt atcactccaa | 3300 |
| gaacgttgtt acctctccgg tgccgaaagg tgatagcgtc tatgttggca ccagcggtgg | 3360 |
| cactctggtg gcgatcggtc agtaaatttgt ttaactttaa gaaggagagc tcaatatgtc | 3420 |
| tcaatccgta gaatcacgga ctcgaatcaa aaacgaacgt acgaatcag gtgttatccc | 3480 |
| ttacgcaaaa atgggatact gggatgctga ttacgttatc aaagatactg acgtacttgc | 3540 |
| aatgttccgt atgacacctc aaaaaggtgt tgacccagtt gaatgtgcag ccgcaatcgc | 3600 |
| aggtgaatct tcaacagcaa cttggacagt tgtatggaca gaccttctaa cagcatgtga | 3660 |

```
tctttaccgt gcaaaagcat accgtgttga cccagttcct ggtgcaactg atcaatactt    3720
tgcttacatc gcatacgaat tagacctatt tgaagaaggt tctttagcta acttaacagc    3780
atcaattatt ggtaacgtat tcggattcaa agcggtaaat gctttaagat tagaagatat    3840
gcgtcttcca attgcatacc taaaaacttt ccaaggtcca gcaactggtg taattgtaga    3900
acgtgaaaga ttagacaaat atggtcgtcc tttattaggt gcaacagtta aaccaaaatt    3960
aggtctatct ggtaaaaact atggtcgtgt agtttacgaa ggtcttaaag gtggtctaga    4020
tttccttaaa gatgatgaaa acattaactc tcaaccattc atgagatgga agagcgttt    4080 cttattcggt atcgaaggtg taaaccgtgc tgctgctgct gctggtgaag taaaaggtca    4140
ctacttcaac gttactgctg gtacaatgga agatatgtat gaacgtgctg aattctgtaa    4200
agaaatcggt agtgtaatct gtatgatcga ccttgtaatc ggatatactg ctattcaaag    4260
tatggcgatc tgggcacgta aaaacagtat gattcttcac ttacaccgtg ctggtaactc    4320
tacatactca cgtcaaaaaa cacatggtat gaacttccgt gtaatttgta agtggatgcg    4380
tatggcaggt gttgaccaca tacacgcagg tacagttgta ggtaaactag aagggatcc    4440 tttaatggtt aaaggtttct ataacacatt attagaaaca caaacagatg taaatcttgt    4500
acaaggtctt ttctttgctc aagattgggc agcacttaac aaatgtatgc cagttgcttc    4560
aggtggtatt cactgtggtc aaatgcacca acttattaac tacttaggtg acgacgtagt    4620
attacaattt ggtggtggta ctattggtca cccagatggt atccaagctg gtgctactgc    4680
aaaccgtgta gcacttgaat gtatggttgt agcacgtaac gaaggtcgtg actatgtaac    4740
agagggtcct caaattcttc gtaatgcagc taagagctgt ggacctcttc aaacagcatt    4800
agatttatgg aaagacatta ctttcaacta tgcttctact gatacagctg acttcgtaga    4860
aactgcaaca gctaacaagt aatttgttta actttaagaa ggagatgcta gcatgacgaa    4920
aacgcgctcg aacatggcgc gctacggcac cagcctggcc atcgtgctgg gcgtgcacgt    4980
ggtcgccgtg gtgctgacgc tcaactggtc ggtgccccag gccatcgagc tgccgccggc    5040
agcgatgatg gtcgagttgg cgccgttgcc ggagcccgcg ccaccgccac cgcccaaggc    5100
cgcgcccaag ccaccggcag aggtcgagga gccgccgctg cccaagctgg tggaggcccc    5160
caagccgaag atcgccatcg ccaagccgcc caagcccaag gccaagccgc agccgcccaa    5220
gcctgagaaa aagcctgagc cgccgaagga cgaaccaccg gccaaggacg atgtggcgga    5280 tacccccgcca agcaacgcgc agccgcagaa atcggccgca ccggcaccga gcatcgcctc    5340
caacagcaat gccctgccca gctggcagag cgacctgctg cgccacctgg ccaagtacaa    5400
gaagtacccg gaagacgctc gccgtcgcgg cctgcagggc atcaaccgcc tgcgcttcgt    5460
ggtcgacgcc gagggcaagg tagtctcgta ctcgctggcc ggaggctcgg gcagcgcggc    5520
gctggaccgg gcgaccctgg aaatgatccg tcgcgcaggc tccgtaccga agccgccagc    5580
ggagctgttg aacaatggca cgatcgaagt cgtggcgccg ttcgtctatt ccctggaccg    5640
acgctaagcg gccgccatca aataaaacga aaggctcagt cgaaagactg gcctttcgt    5700 tttatctgtt gtttgtcggt gaacgctctc ctgagtagga caaatccgcc gggagcggat    5760
ttgaacgttg cgaagcaacg gcccggaggg tggcgggcag gacgcccgcc ataaactgcc    5820
aggcatcaaa ttaagcagaa ggccatcctg acggatggcc ttttttgcgtt tctacaaact    5880 ctaagaaacc aattgtccat attgcatcag acattgccgt cactgcgtct tttactggct    5940
cttctcgcta accaaaccgg taaccccgct tattaaaagc attctgtaac aaagcgggac    6000
```

```
caaagccatg acaaaaacgc gtaacaaaag tgtctataat cacggcagaa aagtccacat    6060
tgattatttg cacggcgtca cactttgcta tgccatagca ttttttatcca taagattagc    6120
ggatcctacc tgacgctttt tatcgcaact ctctactgtt tctccatttt gtttaacttt    6180
aagaaggaga tggtaccatg actgaacttg gttctgatac tttgccctct gtgggccagt    6240
ggcaacaaat tctgactgcg ccacccgtct ggcaggtcaa ggtgcagact gcatcctgga    6300
caagtgccgc gctggcgctg cgcgatcagg cgggcgttt gctgggattg tgggagagg     6360
cgggccatga aaatgcattt ttttacatac atgcgctggg ccttggttca accggatatt    6420
tgtggatcac tctgacggtg caatccagcg agggacaatt tccctcgctg ccgacatt t   6480
ttcccgctgc ctcgcggatg gagcgggccc tgtacgatct tacgggaatc agggcggcgg    6540
ggaatgccga tacccggcca tggctccgcc atcagtgctg gccagcgggg attttttccac   6600
tgcgggaggg acaactggat ggcagttcct tcggcgtgga tggtgatgcc gattatcctt    6660
ttcaattaat cgatagcgtg gatgtccacc agattccagt gggaccggta cacgcgggca    6720
ccattgagcc cggacacttt cgttttttcgt gtgtcggtga acaaattctg cgtctggaag    6780
aacgattggg atacacccac aagggcgtcg aacgcctttt ccaagatcgg gatgtgtttg    6840
cgggtgcgcg tctggcagga cgcatcagtg gtgacactac agcgggttat gcctgggcct    6900
acagcatggc ggtggaatcc attgcccgat gcgaaatccc gcctcgtgca ccgctttgc     6960
gtgctgtttg cctggaacgg gagcgcatgg ccaaccatct gggtgatctt gccgctctgg    7020
ggaatgacgc tggcttcgcc ttctgtcagt cacaattcct gttcatcaag gaaagcctgc    7080
tgcgcgaaaa ccaggaaatt ttcggacacc gctatttgat ggactgcatt attcccggtg    7140
gtgtagcttt tgatctgaac tccgcgcaaa cagccgcgat tcagcgtaac agtgaatcct    7200
ggcagcgcac cgtgcagcgt ttggacctcc tcttgcagga gcactccggt ctgcgggatc    7260
gtctggtggg tacaggaaaa attgtgccac cccgtgctgc agcactcggt atggcggggc    7320
ttgccggccg cgccagtggt caggcctggg atttgcgggt ccagtttccc catgcacctt    7380
atcagaatct ggatgtttcc atgcagcttt ccccggaagg tgacgtggcc gcacgctggc    7440
aattgcgctt tcgggaattc tatgagtctc tgcgtctgca gacccagttg ctgttggatc    7500
tacccagtgg agatgtcagc gcaaccattc cggaaagcat cccgatggc gaaggcttgg     7560
gcattgtcga agcatggcgc ggcgaggtct ttgtcgccct atctgtggaa acgcccgta    7620
ttaaacgctg ccatccccac gatccctcgt ggaccctctg gccggtcctt gaggaggccg    7680
tgctgaacga tattgttgcc gactttccgc tgatcaataa atcgttcaat ttgagttaca    7740
gcggacatga tttatgattt gtttaacttt aagaaggaga tctcgagatg tcgactcctg    7800
acaatcacgg caagaaagcc cctcaatttg ctgcgttcaa accgctaacc acggtacaga    7860
acgccaacga ctgttgctgc gacggcgcat gttccagcac gccaactctc tctgaaaacg    7920
tctccggcac ccgctatagc tggaaagtca gcggcatgga ctgcgccgcc tgtgcgcgca    7980
aggtagaaaa tgccgtgcgc cagcttgcag gcgtgaatca ggtgcaggtg ttgttcgcca    8040
ccgaaaaact ggtggtcgat gccgacaatg acattcgtgc acaagttgaa tctgcgctgc    8100
aaaaagcagg ctattccctg cgcgatgaac aggccgccga agaaccgcaa gcatcacgcc    8160
tgaaagagaa tctgccgctg attacgctaa tcgtgatgat ggcaatcagc tggggtctgg    8220
agcagttcaa tcatccgttc gggcaactgg cgtttatcgc gaccacgctg ttgggctgt    8280
acccgattgc tcgtcaggca ttacggttga tcaaatccgg cagctacttc gccattgaaa    8340
ccttaatgag cgtagccgct attggtgcac tgtttattgg cgcaacggct gaagctgcga    8400
```

```
tggtgttgct gctgtttttg attggtgaac gactggaagg ctgggccgcc agccgcgcgc   8460
gtcagggcgt tagcgcgtta atggcgctga aaccagaaac cgccacgcgc ctgcgtaagg   8520
gtgagcggga agaggtggcg attaacagcc tgcgccctgg cgatgtgatt gaagtcgccg   8580
caggtgggcg tttgcctgcc gacggtaaac tgctctcacc gtttgccagt tttgatgaaa   8640
gcgccctgac cggcgaatcc attccggtgg agcgcgcaac gggcgataaa gtccctgctg   8700
gtgccaccag cgtagaccgt ctggtgacgt tggaagtgct gtcagaaccg ggagccagcg   8760
ccattgaccg gattctgaaa ctgatcgaag aagccgaaga gcgtcgcgct cccattgagc   8820
ggtttatcga ccgtttcagc cgtatctata cgcccgcgat tatggccgtc gctctgctgg   8880
tgacgctggt gccaccgctg ctgtttgccg ccagctggca ggagtggatt tataaagggc   8940
tgacgctgct gctgattggc tgcccgtgtg cgttagttat ctcaacgcct gcggcgatta   9000
cctccgggct ggcggcggca gcgcgtcgtg gggcgttgat taaaggcgga gcggcgctgg   9060
aacagctggg tcgtgttact caggtggcgt ttgataaaac cggtacgctg accgtcggta   9120
aaccgcgcgt taccgcgatt catccggcaa cgggtattag tgaatctgaa ctgctgacac   9180 tggcggcgg ggtcgagcaa ggcgcgacgc atccactggc gcaagccatc gtacgcgaag   9240
cacaggttgc tgaactcgcc attcccaccg ccgaatcaca gcgggcgctg gtcgggtctg   9300
gcattgaagc gcaggttaac ggtgagcgcg tattgatttg cgctgccggg aaacatcccg   9360
ctgatgcatt tactggttta attaacgaac tggaaagcgc cgggcaaacg gtagtgctgg   9420
tagtacgtaa cgatgacgtg cttggtgtca ttgcgttaca ggataccctg cgcgccgatg   9480
ctgcaactgc catcagtgaa ctgaacgcgc tgggcgtcaa aggggtgatc ctcaccggcg   9540
ataatccacg cgcagcggcg gcaattgccg gggagctggg gctggagttt aaagcgggcc   9600
tgttgccgga agataaagtc aaagcggtga ccgagctgaa tcaacatgcg ccgctggcga   9660
tggtcggtga cggtattaac gacgcgccag cgatgaaagc tgccgccatc gggattgcaa   9720
tgggtagcgg cacagacgtg gcgctggaaa ccgccgacgc agcattaacc cataaccacc   9780
tgcgcggcct ggtgcaaatg attgaactgg cacgcgccac tcacgccaat atccgccaga   9840
acatcactat tgcgctgggg ctgaaaggga tcttcctcgt caccacgctg ttagggatga   9900
ccgggttgtg gctggcagtg ctggcagata cgggggcgac ggtgctggtg acagcgaatg   9960
cgttaagatt gttgcgcagg agataatttg tttaacttta agaaggagat actagtatgg  10020
tgagcaaggg cgaggagctg ttcaccgggg tggtgcccat cctggtcgag ctggacggcg  10080
acgtaaacgg ccacaagttc agcgtgtccg gcgagggcga gggcgatgcc acctacggca  10140
agctgaccct gaagttcatc tgcaccaccg gcaagctgcc cgtgccctgg cccaccctcg  10200
tgaccaccct gacctacggc gtgcagtgct tcagccgcta ccccgaccac atgaagcagc  10260
acgacttctt caagtccgcc atgcccgaag gctacgtcca ggagcgcacc atcttcttca  10320
aggacgacgg caactacaag acccgcgccg aggtgaagtt cgagggcgac accctggtga  10380
accgcatcga gctgaagggc atcgacttca aggaggacgg caacatcctg ggcacaagc   10440 tggagtacaa ctacaacagc cacaacgtct atatcatggc cgacaagcag aagaacggca  10500
tcaaggtgaa cttcaagatc cgccacaaca tcgaggacgg cagcgtgcag ctcgccgacc  10560
actaccagca gaacaccccc atcggcgacg gccccgtgct gctgcccgac aaccactacc  10620
tgagcaccca gtccgccctg agcaaagacc ccaacgagaa gcgcgatcac atggtcctgc  10680
tggagttcgt gaccgccgcc gggatcactc tcggcatgga cgagctgtac aagtaagttt  10740
```

```
aaacaagctt ggctgttttg gcggatgaga gaagattttc agcctgatac agattaaatc   10800
agaacgcaga agcggtctga taaaacagaa tttgcctggc ggcagtagcg cggtggtccc   10860
acctgacccc atgccgaact cagaagtgaa acgccgtagc gccgatggta gtgtggggtc   10920
tccccatgcg agagtaggga actgccaggc atcaaataaa acgaaaggct cagtcgaaag   10980
actgggcctt tcgttttatc tgttgtttgt cggtgaacgc tctcctgagt aggacaaatc   11040
cgccgggagc ggatttgaac gttgcgaagc aacggcccgg agggtggcgg caggacgcc    11100
cgccataaac tgccaggcat caaattaagc agaaggccat cctgacggat ggccttttg    11160
cgtttctaca aactcttttg tttattttc taaatacatt caaatatgta tccgctcatg    11220
agacaataac cctgataaat gcttcaataa tattgaaaaa ggaagagtat gagtattcaa   11280
catttccgtg tcgcccttat tcccttttt gcggcatttt gccttcctgt ttttgctcac    11340
ccagaaacgc tggtgaaagt aaaagatgct gaagatcagt tgggtgcacg agtgggttac   11400
atcgaactgg atctcaacag cggtaagatc cttgagagtt ttcgccccga gaacgttt     11460
ccaatgatga gcacttttaa agttctgcta tgtggcgcgg tattatcccg tgttgacgcc   11520
gggcaagagc aactcggtcg ccgcatacac tattctcaga atgacttggt tgagtactca   11580
ccagtcacag aaaagcatct tacgatggc atgacagtaa gagaattatg cagtgctgcc    11640
ataaccatga gtgataacac tgcggccaac ttacttctga caacgatcgg aggaccgaag   11700
gagctaaccg ctttttgca caacatgggg gatcatgtaa ctcgccttga tcgttgggaa    11760
ccggagctga atgaagccat accaaacgac gagcgtgaca ccacgatgcc tgtagcaatg   11820
gcaacaacgt tgcgcaaact attaactggc gaactactta ctctagcttc ccggcaacaa   11880
ttaatagact ggatggaggc ggataaagtt gcaggaccac ttctgcgctc ggcccttccg   11940
gctggctggt ttattgctga taaatctgga gccggtgagc gtgggtctcg cggtatcatt   12000
gcagcactgg ggccagatgg taagccctcc cgtatcgtag ttatctacac gacggggagt   12060
caggcaacta tggatgaacg aaatagacag atcgctgaga taggtgcctc actgattaag   12120
cattggtaac tgtcagacca agtttactca tatatacttt agattgattt aaaacttcat   12180
ttttaattta aaaggatcta ggtgaagatc ctttttgata atctcatgac caaaatccct   12240
taacgtgagt tttcgttcca ctgagcgtca gaccccgtag aaaagatcaa aggatcttct   12300
tgagatcctt ttttctgcg cgtaatctgc tgcttgcaaa caaaaaaacc accgctacca    12360
gcggtggttt gtttgccgga tcaagagcta ccaactcttt ttccgaaggt aactggcttc   12420
agcagagcgc agataccaaa tactgtcctt ctagtgtagc cgtagttagg ccaccacttc   12480
aagaactctg tagcaccgcc tacataccttc gctctgctaa tcctgttacc agtggctgct   12540
gccagtggcg ataagtcgtg tcttaccggg ttggactcaa gacgatagtt accggataag   12600
gcgcagcggt cgggctgaac ggggggttcg tgcacacagc ccagcttgga gcgaacgacc   12660
tacaccgaac tgagatacct acagcgtgag ctatgagaaa gcgccacgct tcccgaaggg   12720
agaaaggcgg acaggtatcc ggtaagcggc agggtcggaa caggagagcg cacgagggag   12780
cttccagggg gaaacgcctg gtatctttat agtcctgtcg ggtttcgcca cctctgactt   12840
gagcgtcgat ttttgtgatg ctcgtcaggg gggcggagcc tatggaaaaa cgccagcaac   12900
gcggcctttt tacggttcct ggccttttgc tggccttttg ctcacatgtt ctttcctgcg   12960
ttatcccctg attctgtgga taaccgtatt accgcctttg agtgagctga taccgctcgc   13020
cgcagccgaa cgaccgagcg cagcgagtca gtgagcgagg aagcggaaga gcgcctgatg   13080
cggtattttc tccttacgca tctgtgcggt atttcacacc gcatatggtg cactctcagt   13140
```

```
acaatctgct ctgatgccgc atagttaagc cagtatacac tccgctatcg ctacgtgact    13200
gggtcatggc tgcgcccga cacccgccaa cacccgctga cgcgccctga cgggcttgtc    13260
tgctcccggc atccgcttac agacaagctg tgaccgtctc cgggagctgc atgtgtcaga    13320
ggttttcacc gtcatcaccg aaacgcgcga ggcagcagat caattcgcgc gcgaaggcga    13380
agcggcatgc ataatgtgcc tgtcaaatgg acgaagcagg gattctgcaa accctatgct    13440
actccgtcaa gccgtcaatt gtctgattcg ttaccaatta tgacaacttg acggctacat    13500
cattcacttt ttcttcacaa ccggcacgga actcgctcgg gctggcccg gtgcattttt     13560 taaatacccg cgagaaatag agttgatcgt caaaaccaac attgcgaccg acggtggcga    13620
taggcatccg ggtggtgctc aaaagcagct tcgcctggct gatacgttgg tcctcgcgcc    13680
agcttaagac gctaatccct aactgctggc ggaaaagatg tgacagacgc gacggcgaca    13740
agcaaacatg ctgtgcgacg ctggcgatat caaaattgct gtctgccagg tgatcgctga    13800
tgtactgaca agcctcgcgt acccgattat ccatcggtgg atggagcgac tcgttaatcg    13860
cttccatgcg ccgcagtaac aattgctcaa gcagatttat cgccagcagc tccgaatagc    13920
gcccttcccc ttgcccggcg ttaatgattt gcccaaacag gtcgctgaaa tgcgctggt     13980 gcgcttcatc cgggcgaaag aacccgtat tggcaaatat tgacggccag ttaagccatt     14040
catgccagta ggcgcgcgga cgaaagtaaa cccactggtg ataccattcg cgagcctccg    14100
gatgacgacc gtagtgatga atctctcctg gcgggaacag caaaatatca cccggtcggc    14160
aaacaaattc tcgtccctga tttttcacca cccctgacc gcgaatggtg agattgagaa     14220 tataacctt cattcccagc ggtcggtcga taaaaaaatc gagataaccg ttggcctcaa     14280
tcggcgttaa acccgccacc agatgggcat taaacgagta tcccggcagc aggggatcat    14340
tttgcgcttc agccatactt ttcatactcc cgccattcag ag                       14382
```